(12) United States Patent
Ohshima et al.

(10) Patent No.: US 6,469,002 B1
(45) Date of Patent: Oct. 22, 2002

(54) IMIDAZOLIDINE COMPOUNDS

(75) Inventors: Etsuo Ohshima, Nagareyama; Hiroki Sone, Shizuoka; Osamu Kotera, Shizuoka; Rie Komatsu, Shizuoka, all of (JP); Gregory J. LaRosa, Waban; Jay R. Luly, Wellesley, both of MA (US)

(73) Assignees: Millennium Pharmaceuticals, Inc., Cambridge, MA (US); Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/838,551

(22) Filed: Apr. 19, 2001

(51) Int. Cl.[7] .................. A61K 31/454; A61K 31/4164; C07D 233/26; C07D 401/12; C07D 403/12
(52) U.S. Cl. .............................. 514/232.2; 514/254.05; 514/319; 514/326; 514/400; 544/139; 544/370; 546/205; 546/210; 548/300.1; 548/314.7
(58) Field of Search ................................. 546/210, 205; 548/300.1, 314.7; 544/139, 370; 514/232.2, 254.05, 319, 326, 400

(56) References Cited

U.S. PATENT DOCUMENTS 2,883,368 A * 4/1959 Middleton .................. 508/255

OTHER PUBLICATIONS

Foye, W.O., *Principles of Medicinal Chemistry*, 3rd. ed., Philadelphia, Lea & Febiger, pp. 416–425 (1989).

* cited by examiner

*Primary Examiner*—Laura L. Stockton
(74) *Attorney, Agent, or Firm*—Hamilton, Brook, Smith & Reynolds, P.C.

(57) ABSTRACT

Disclosed are novel compounds and a method of treating inflammatory diseases. The method comprises administering to an individual in need an effective amount of an imidazolidine compound represented by Structural Formula (I):

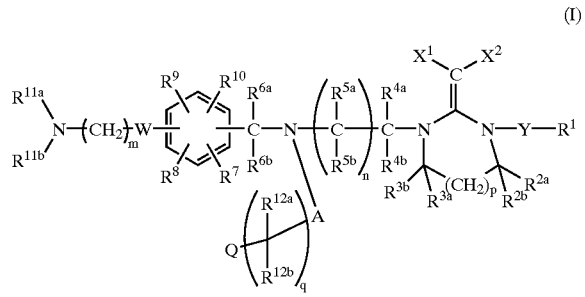

and physiologically or pharmaceutically acceptable salts thereof.

22 Claims, 13 Drawing Sheets

Step 10-1

$L^1$—Y—$R^1$ (III)

IMIDAZOLIDINE COMPOUNDS

BACKGROUND OF THE INVENTION

Chemokines constitute a family of small cytokines that are produced in inflammation and regulate leukocyte recruitment (Baggiolini, M. et al., *Adv. Immunol.*, 55: 97–179 (1994); Springer, T. A., *Annu. Rev. Physiol.*, 57: 827–872 (1995); and Schall, T. J. and K. B. Bacon, *Curr. Opin. Immunol.*, 6: 865–873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

The chemokines are related in primary structure and share four conserved cysteines, which form disulfide bonds. Based upon this conserved cysteine motif, the family can be divided into distinct branches, including the C—X—C chemokines (α-chemokines) in which the first two conserved cysteines are separated by an intervening residue (e.g., IL-8, IP-10, Mig, I-TAC, PF4, ENA-78, GCP-2, GROα, GROβ, GROγ, NAP-2, NAP-4), and the C—C chemokines (β-chemokines), in which the first two conserved cysteines are adjacent residues (e.g., MIP-1α, MIP-1β, RANTES, MCP-1, MCP-2, MCP-3, I-309)(Baggiolini, M. and Dahinden, C. A., *Immunology Today*, 15:127–133 (1994)). Most CXC-chemokines attract neutrophil leukocytes. For example, the CXC-chemokines interleukin 8 (IL-8), GRO alpha (GROα), and neutrophil-activating peptide 2 (NAP-2) are potent chemoattractants and activators of neutrophils. The CXC-chemokines designated Mig (monokine induced by gamma interferon) and IP-10 (interferon-gamma inducible 10 kDa protein) are particularly active in inducing chemotaxis of activated peripheral blood lymphocytes. CC-chemokines are generally less selective and can attract a variety of leukocyte cell types, including monocytes, eosinophils, basophils, T lymphocytes and natural killer cells. CC-chemokines such as human monocyte chemotactic proteins 1–3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

Chemokines (e.g., CC- and CXC-chemokines) act through receptors which belong to a superfamily of seven transmembrane spanning G protein-coupled receptors (Murphy, P. M., *Annu. Rev. Immunol.*, 12: 593–633 (1994); Gerard, C. and N. P. Gerard, *Curr. Opin. Immunol.*, 6: 140–145 (1994)). This family of G protein-coupled (serpentine) receptors comprises a large group of integral membrane proteins, containing seven transmembrane-spanning regions. The receptors are coupled to G proteins, which are heterotrimeric regulatory proteins capable of binding GTP and mediating signal transduction from coupled receptors, for example, by the production of intracellular mediators.

The chemokine receptors can be divided into groups, which include, CC-chemokine receptors 1 through 9 (CCR1–CCR9), which can bind certain CC-chemokines, and CXC-chemokine receptors 1 through 4 (CXCR1–CXCR4), which can bind certain CXC-chemokines. In general, the CC-chemokine receptors occur on several types of leukocytes, and are important for the migration of monocytes, eosinophils, basophils, and T cells (Qin, S. et al., *Eur. J. Immunol.*, 26: 640–647 (1996); Carr, M. W. et al., *Proc. Natl. Acad. Sci. USA*, 91(9): 3652–3656 (1994); Taub, D. D. et al., *J. Clin. Invest.*, 95(3): 1370–1376 (1995); Neote, K. et al., *Cell*, 72: 415–425 (1993); Gao, J.-L. et al., *J. Exp. Med.*, 177: 1421–1427 (1993); Charo, I. F. et al., *Proc. Natl. Acad. Sci. USA*, 91: 2752–2756 (1994); Myers, S. J. et al., *J. Biol. Chem.*, 270: 5786–5792 (1995); Combadiere, C. et al.,*J. Biol. Chem.*, 270(27): 16491–16494 (1995); Ponath, P. D. et al., *J. Exp. Med.*, 183: 2437–2448 (1996); Daugherty, B. L. et al., *J. Exp. Med.*, 183: 2349–2354 (1996); Power, C. A. et al.,*J. Biol. Chem.*, 270: 19495–19500 (1995); Hoogewerf, A. J. et al., *Biochem. Biophys. Res. Commun.*, 218: 337–343 (1996); and Samson, M. et al., *Biochemistry*, 35: 3362–3367 (1996)).

In contrast, the two IL-8 receptors, CXCR1 and CXCR2, are largely restricted to neutrophils and are important for the migration of neutrophils (Baggiolini, M. et al., *Adv. Immunol.*, 55: 97–179 (1994)). The IL-8 receptors, CXCR1 (IL-8R1, interleukin-8 receptor type 1; Holmes, W. E. et al., *Science*, 253: 1278–1280 (1991)) and CXCR2 (IL-8R2, interleukin-8 receptor type 2; Murphy, P. M. and H. L. Tiffany, *Science*, 253: 1280–1283 (1991)) both bind IL-8 and appear to recognize the $NH_2$-terminal Glu-Leu-Arg (ELR) motif as an essential binding epitope observed in CXC-chemokines that induce neutrophil chemotaxis (Clark-Lewis, I. et al., *J. Biol. Chem.*, 266: 23128–23134 (1991); Hebert, C. A. et al. *J. Biol. Chem.*, 266: 18989–18994 (1991); and Clark-Lewis, I. et al., *Proc. Natl. Acad. Sci. USA*, 90: 3574–3577 (1993)). The CXCR1 receptor of human neutrophils binds only IL-8 with high affinity, while the CXCR2 receptor binds IL-8 with similar affinity as CXCR1 but also binds other ELR-containing CXC-chemokines (Baggiolini, M. et al., *Adv. Immunol.*, 55: 97–179 (1994)). Both receptors are capable of coupling to the same G protein α-subunits, exhibiting functional coupling to $G\alpha i2$, $G\alpha i3$, $G\alpha 14$, $G\alpha 15$, and $G\alpha 16$ (Wu, et al., *Science*, 261: 101–103 (1993)). Whether these two receptor subtypes play distinct physiologic roles is not clear.

In contrast to granulocytes and monocytes, lymphocyte responses to chemokines are not well understood. Notably, none of the receptors of known specificity appear to be restricted to lymphocytes and the chemokines that recognize these receptors cannot, therefore, account for events such as the selective recruitment of T lymphocytes that is observed in T cell-mediated inflammatory conditions. Moreover, although a number of proteins with significant sequence similarity and similar tissue and leukocyte subpopulation distribution to known chemokine receptors have been identified and cloned, the ligands for these receptors remain undefined. Thus, these proteins are referred to as orphan receptors. The characterization of the ligand(s) of a receptor, is essential to an understanding of the interaction of chemokines with their target cells, the events stimulated by this interaction, including chemotaxis and cellular activation of leukocytes, and the development of therapies based upon modulation of receptor function.

A chemokine receptor that binds the CXC-chemokines IP-10 and Mig has been cloned and characterized (Loetscher, M. et al., *J. Exp. Med.*, 184: 963–969 (1996)).

The receptor mediates Ca$^{2+}$ (calcium ion) mobilization and chemotaxis in response to IP-10 and Mig. CXCR3 expressing cells show no significant response to the CXC-chemokines IL-8, GROα, NAP-2, GCP-2 (granulocyte chemotactic protein-2), ENA78 (epithelial-derived neutrophil-activating peptide 78), PF4 (platelet factor 4), or the CC-chemokines MCP-1, MCP-2, MCP-3, MCP-4, MIP-1α, MIP-1β, RANTES, I309, eotaxin or lymphotactin. Moreover, a third ligand for CXCR3, I-TAC (Interferon-inducible T cell Alpha Chemoattractant), has also been found to bind to the receptor with high affinity and mediate functional responses (Cole, K. E. et al., *J. Exp. Med.*, 187: 2009–2021 (1998)).

The restricted expression of human CXCR3 in activated T lymphocytes and the ligand selectivity of CXCR3 are noteworthy. The human receptor is highly expressed in IL-2 activated T lymphocytes, but was not detected in resting T lymphocytes, monocytes or granulocytes (Qin, S. et al., *J. Clin. Invest.*, 101: 746–754 (1998)). Additional studies of receptor distribution indicate that it is mostly CD3$^+$ cells that express CXCR3, including cells which are CD95$^+$, CD45RO$^+$, and CD45RA$^{low}$, a phenotype consistent with previous activation, although a proportion of CD20$^+$ (B) cells and CD56$^+$ (NK) cells also express this receptor. The selective expression in activated T lymphocytes is of interest, because other receptors for chemokines which have been reported to attract lymphocytes (e.g., MCP-1, MCP-2, MCP-3, MIP-1α, MIP-1β, RANTES) are also expressed by granulocytes, such as neutrophils, eosinophils, and basophils, as well as monocytes. These results suggest that the CXCR3 receptor is involved in the selective recruitment of effector T cells.

CXCR3 recognizes unusual CXC-chemokines, designated IP-10, Mig and I-TAC. Although these belong to the CXC-subfamily, in contrast to IL-8 and other CXC-chemokines which are potent chemoattractants for neutrophils, the primary targets of IP-10, Mig and I-TAC are lymphocytes, particularly effector cells such as activated or stimulated T lymphocytes and natural killer (NK) cells (Taub, D. D. et al., *J. Exp. Med.*, 177: 18090–1814 (1993); Taub, D. D. et al., *J. Immunol.*, 155: 3877–3888 (1995); Cole, K. E. et al., *J. Exp. Med.*, 187: 2009–2021 (1998)). (NK cells are large granular lymphocytes, which lack a specific T cell receptor for antigen recognition, but possess cytolytic activity against cells such as tumor cells and virally infected cells.) Consistently, IP-10, Mig and I-TAC lack the ELR motif, an essential binding epitope in those CXC-chemokines that efficiently induce neutrophil chemotaxis (Clark-Lewis, I. et al., *J. Biol. Chem.* 266: 23128–23134 (1991); Hebert, C. A. et al., *J. Biol. Chem.*, 266: 18989–18994 (1991); and Clark-Lewis, I. et al., *Proc. Natl. Acad. Sci. USA*, 90: 3574–3577 (1993)). In addition, both recombinant human Mig and recombinant human IP-10 have been reported to induce calcium flux in tumor infiltrating lymphocytes (TIL) (Liao, F. et al, *J. Exp. Med.*, 182: 1301–1314 (1995)). While IP-10 has been reported to induce chemotaxis of monocytes in vitro (Taub, D. D. et al., *J. Exp. Med.*, 177: 1809–1814 (1993), the receptor responsible has not been identified), human Mig and I-TAC appear highly selective, and do not show such an effect (Liao, F. et al., *J. Exp. Med.*, 182: 1301–1314 (1995); Cole, K. E. et al., *J. Exp. Med.*, 187: 2009–2021 (1998)). IP-10 expression is induced in a variety of tissues in inflammatory conditions such as psoriasis, fixed drug eruptions, cutaneous delayed-type hypersensitivity responses, tuberculoid leprosy, and in experimental glomerulonephritis, and experimental allergic encephalomyelitis. IP-10 has a potent in vivo antitumor effect that is T cell dependent, is reported to be an inhibitor of angiogenesis in vivo and can induce chemotaxis and degranulation of NK cells in vitro, suggesting a role as a mediator of NK cell recruitment and degranulation (in tumor cell destruction, for example) (Luster, A. D. and P. Leder, *J. Exp. Med.*, 178: 1057–1065 (1993); Luster, A. D. et al., *J. Exp. Med.* 182: 219–231 (1995); Angiolillo, A. L. et al., *J. Exp. Med.*, 182: 155–162 (1995); Taub, D. D. et al., *J. Immunol.*, 155: 3877–3888 (1995)). The expression patterns of IP-10, Mig and I-TAC are also distinct from that of other CXC chemokines in that expression of each is induced by interferon-gamma (IFNγ), while the expression of IL-8 is down-regulated by IFNγ (Luster, A. D. et al., *Nature*, 315: 672–676 (1985); Farber, J. M., *Proc. Natl. Acad. Sci. USA*, 87: 5238–5242 (1990); Farber, J. M., Biochem. *Biophys. Res. Commun.*, 192 (1): 223–230 (1993), Liao, F. et al., *J. Exp. Med.*, 182: 1301–1314 (1995); Seitz, M. et al., *J. Clin. Invest.*, 87: 463–469 (1991); Galy, A. H. M. and H. Spits, *J. Immunol.*, 147: 3823–3830 (1991); Cole, K. E. et al., *J. Exp. Med.*, 187: 2009–2021 (1998)).

Chemokines are recognized as the long-sought mediators for the recruitment of lymphocytes. Several CC-chemokines were found to elicit lymphocyte chemotaxis (Loetscher, P. et al., *FASEB J.*, 8: 1055–1060 (1994)), however, they are also active on granulocytes and monocytes (Uguccioni, M. et al., *Eur. J. Immunol.*, 25: 64–68 (1995); Baggiolini, M. and C. A. Dahinden, *Immunol. Today*, 15: 127–133 (1994)). The situation is different for IP-10, Mig and I-TAC, which are selective in their action on lymphocytes, including activated T lymphocytes and NK cells, and which bind CXCR3, a receptor which does not recognize numerous other chemokines and which displays a selective pattern of expression.

In view of these observations, it is reasonable to conclude that the formation of the characteristic infiltrates in inflammatory lesions, such as, for example, delayed-type hypersensitivity lesions, sites of viral infection and certain tumors is a process mediated via CXCR3 and regulated by CXCR3 expression. Lymphocytes, particularly T lymphocytes, bearing a CXCR3 receptor as a result of activation can be recruited into inflammatory lesions, sites of infection and/or tumors by IP-10, Mig and/or I-TAC, which can be induced locally by interferon-gamma. Thus, CXCR3 plays a role in the selective recruitment of lymphocytes, particularly effector cells such as activated or stimulated T lymphocytes.

Many existing drugs have been developed as antagonists of the receptors for biogenic amines, for example, as antagonists of the dopamine and histamine receptors. However, no antagonists of the receptors for larger proteins such as chemokines and C5a have been successfully developed and marketed. Small molecule antagonists of the interaction between CXC-chemokine receptors and their ligands, including IP-10, Mig and I-TAC, would provide compounds useful for inhibiting harmful inflammatory processes "triggered" by receptor ligand interaction, as well as valuable tools for the investigation of receptor-ligand interactions.

Diaminoethylene derivatives possessing an electron withdrawing group(s) are known as histamine H2 receptor antagonists and as drugs useful for treating peptic ulcers (*Principles of Medicinal Chemistry*, Foye, W. O., Ed. Lea & Febiger, Philadelphia, 1989, 3rd ed.).

SUMMARY OF THE INVENTION

The present invention relates to small organic compounds which modulate chemokine receptor activity and are useful in the treatment (e.g., palliative therapy, curative therapy, prophylactic therapy) of certain diseases and conditions e.g., inflammatory diseases (e.g., psoriasis), autoimmune diseases (e.g., rheumatoid arthritis, multiple sclerosis), graft rejection (e.g., allograft rejection, xenograft rejection), infectious diseases, cancers. It has now been found that a number of small organic molecules are antagonists of chemokine receptor function (e.g., CXCR3), and can inhibit leukocyte activation and/or recruitment. An antagonist of chemokine receptor function is a molecule which can inhibit the binding of one or more chemokines to one or more chemokine receptors on leukocytes and/or other cell types. As a consequence, and by virtue of the fact that antagonists lack chemokine agonist properties, processes and cellular responses mediated by chemokine receptors can be inhibited with these small organic molecules. In one aspect, the invention relates to small organic compounds which are antagonists of CXCR3. Such CXCR3 antagonists can inhibit binding of one or more chemokines (e.g., CXC-chemokines, such as IP-10, Mig and/or I-TAC) to CXCR3.

The invention also relates to a method of modulating (inhibiting or promoting) an inflammatory response in an individual in need of such therapy. The method comprises administering a therapeutically effective amount of a compound (e.g., small organic molecule) which inhibits or promotes mammalian CXCR3 function to an individual in need thereof.

The invention also relates to a method of treating an individual having a disease associated with pathogenic leukocyte recruitment and/or activation, such as the inflammatory and autoimmune diseases discussed herein. The method comprises administering to the individual a therapeutically effective amount of a compound or small organic molecule which is an antagonist of chemokine receptor function. Compounds or small organic molecules which have been identified as antagonists of chemokine receptor function are discussed in detail herein, and can be used for the manufacture of a medicament for treating or preventing a disease associated with pathogenic leukocyte recruitment and/or activation.

The invention further relates to a compound or small organic molecule described herein for use in therapy (including prophylaxis) or diagnosis, and to the use of such a compound or small organic molecule for the manufacture of a medicament for the treatment of a particular disease or condition as described herein (e.g., inflammatory disease, cancer, autoimmune disease, graft rejection, allergic disease).

The invention also includes pharmaceutical compositions comprising one or more of the compounds or small organic molecules described herein and a suitable pharmaceutical carrier. The invention further relates to novel compounds which can be used to treat an individual with a disease associated with inflammation and/or pathogenic leukocyte recruitment and/or activation.

DETAILED DESCRIPTION OF THE INVENTION

Figure 1:
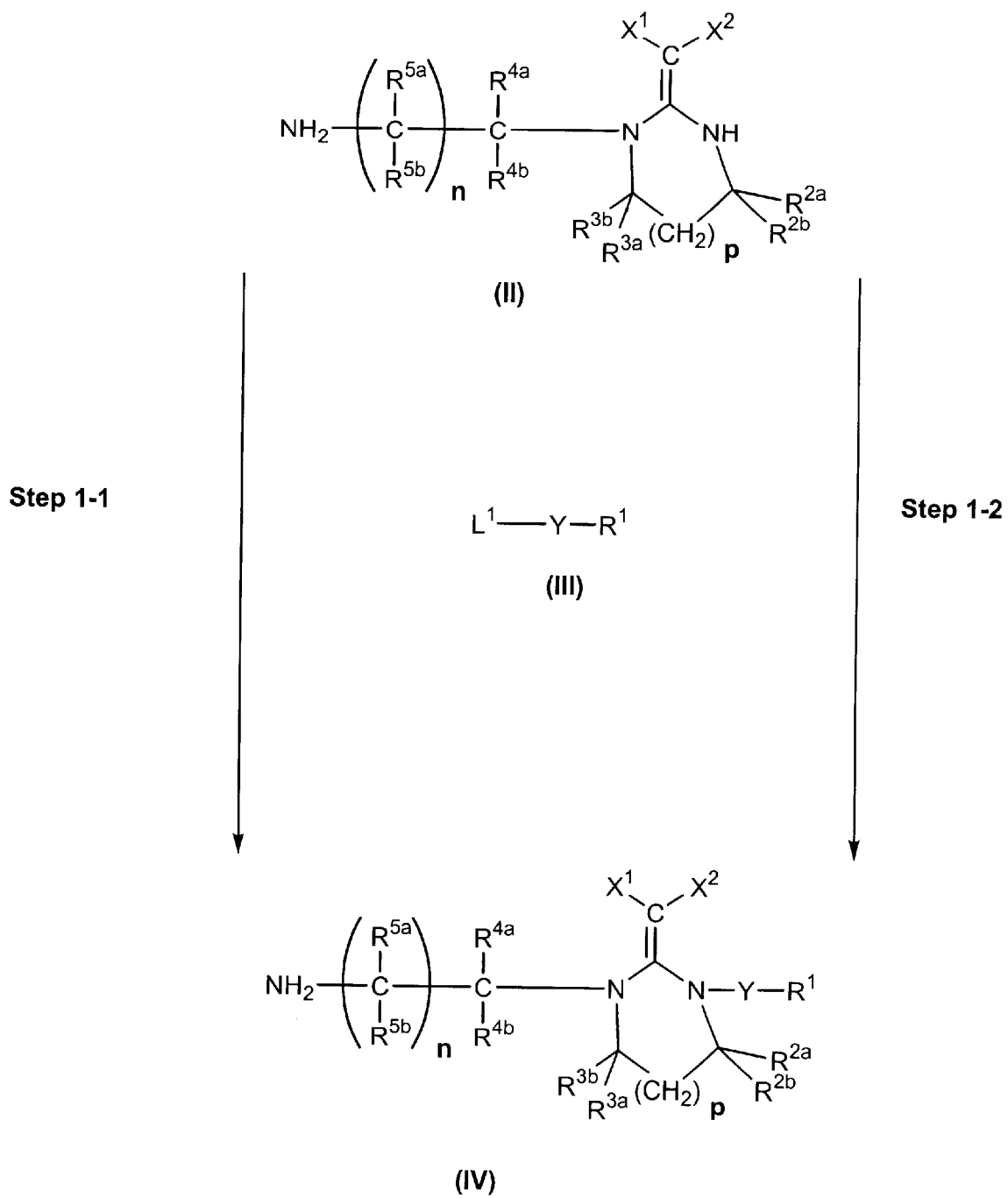
FIG. 1 is schematic diagram showing the preparation of compounds represented by Structural Formula (IV).

The present invention relates to small organic compounds which modulate chemokine receptor activity and are useful in the prevention or treatment of certain autoimmune and inflammatory diseases and conditions, including rheumatoid arthritis, psoriasis, and multiple sclerosis.

Specifically, the present invention relates to imidazolidine derivatives represented by Structural Formula (I):

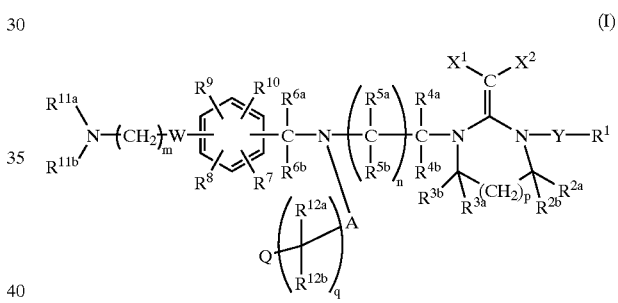

and physiologically or pharmaceutically acceptable salts thereof, wherein:

A is
   a bond,
   —C(=O)—, or
   —SO$_2$—;

Q is
   hydrogen,
   —COOH,
   substituted or unsubstituted cycloalkyl,
   substituted or unsubstituted polycycloalkyl,
   substituted or unsubstituted lower alkenyl,
   substituted or unsubstituted cycloalkenyl,
   substituted or unsubstituted aryl,
   substituted or unsubstituted heteroaryl; or Q and R$^7$ taken together form a bond;

W is
   a bond,
   —O—,
   —S—, or
   —NR$^{13}$—, wherein
      R$^{13}$ is
         hydrogen,
         substituted or unsubstituted lower alkyl,
         substituted or unsubstituted cycloalkyl, substituted or unsubstituted aryl,
substituted or unsubstituted aralkyl, or
substituted or unsubstituted heteroarylalkyl;

$X^1$ and $X^2$ are each, independently,
hydrogen,
—CN,
—NO$_2$,
—SO$_2R^{14a}$,
—SO$_2$NR$^{14a}R^{14b}$,
—C(=O)—R$^{14a}$,
—C(=O)—OR$^{14a}$, or
—C(=O)—NR$^{14a}R^{14b}$, wherein
  $R^{14a}$ and $R^{14b}$ are each, independently,
    hydrogen,
    substituted or unsubstituted lower alkyl,
    substituted or unsubstituted cycloalkyl,
    substituted or unsubstituted aryl, or
    substituted or unsubstituted aralkyl;

Y is
a bond,
—SO$_2$—,
—(C=O)—, or
—(CR$^{15a}R^{15b}$)—, wherein
  $R^{15a}$ and $R^{15b}$ are each, independently,
    hydrogen,
    substituted or unsubstituted lower alkyl,
    substituted or unsubstituted cycloalkyl,
    substituted or unsubstituted aryl, or
    substituted or unsubstituted aralkyl;

$R^1$ is
substituted or unsubstituted lower alkyl,
substituted or unsubstituted cycloalkyl,
substituted or unsubstituted polycycloalkyl,
substituted or unsubstituted lower alkenyl,
substituted or unsubstituted cycloalkenyl,
substituted or unsubstituted aryl,
substituted or unsubstituted heteroaryl,
substituted or unsubstituted aralkyl,
substituted or unsubstituted heteroarylalkyl,
substituted or unsubstituted lower alkoxy,
substituted or unsubstituted lower alkanoyloxy,
a substituted or unsubstituted non-aromatic heterocyclic group;

$R^{2a}$, $R^{2b}$, $R^{3a}$, $R^{3b}$, $R^{4a}$, $R^{4b}$, $R^{1a}$, $R^{5b}$, $R^{6a}$, and $R^{6b}$ are each, independently,
hydrogen,
substituted or unsubstituted lower alkyl,
substituted or unsubstituted cycloalkyl,
substituted or unsubstituted aryl,
substituted or unsubstituted aralkyl,
substituted or unsubstituted heteroarylalkyl; or
$R^{6a}$ and $R^{6b}$ taken together with the carbon atom to which they are bonded form —C(=O)—;

$R^7$, $R^8$, $R^9$, and $R^{10}$ are each, independently,
hydrogen,
hydroxy,
substituted or unsubstituted lower alkyl,
substituted or unsubstituted lower alkoxy,
substituted or unsubstituted lower alkanoyl,
substituted or unsubstituted lower alkanoyloxy
substituted or unsubstituted lower alkoxycarbonyl,
substituted or unsubstituted aryl,
substituted or unsubstituted heteroaryl,
halogen,
—CN,
—NO$_2$,
—COOR$^{16a}$,
—NR$^{16a}R^{16b}$, or
—CONR$^{16a}R^{16b}$, $R^{16a}$ and $R^{16b}$ are each, independently,
hydrogen,
substituted or unsubstituted lower alkyl,
substituted or unsubstituted cycloalkyl,
substituted or unsubstituted aryl,
substituted or unsubstituted aralkyl,
$R^{16a}$ and $R^{16b}$ taken together with the nitrogen atom to which they are bonded form a substituted or unsubstituted heterocyclic group containing at least one nitrogen atom;

$R^{11a}$ and $R^{11b}$ are each, independently,
hydrogen,
substituted or unsubstituted lower alkyl,
substituted or unsubstituted cycloalkyl,
substituted or unsubstituted aryl,
substituted or unsubstituted aralkyl,
substituted or unsubstituted heteroarylakyl; or
$R^{11a}$ and $R^{11b}$ taken together with the nitrogen atom to which they are bonded form a substituted or unsubstituted heterocyclic group containing at least one nitrogen atom;

$R^{12a}$ and $R^{12b}$ are each, independently,
hydrogen,
substituted or unsubstituted lower alkyl,
substituted or unsubstituted cycloalkyl,
substituted or unsubstituted aryl,
substituted or unsubstituted aralkyl,
substituted or unsubstituted heteroarylakyl; or
$R^{12a}$ and $R^{12b}$ taken together with the carbon atom to which they are bonded form a substituted or unsubstituted cyclic group;

n is an integer from 0 to about 4;
m is an integer from 0 to about 6;
p is an integer from 0 to about 2; and
q is an integer from 0 to about 8.

Hereinafter, the compound(s) represented by Formula (I) are referred to as Compound(s) (I) or the compound(s) of the present invention. The same applies to the compounds of other formula numbers.

As used herein, the term "alkoxy" refers to —O-alkyl; "alkanoyloxy" refers to —O—C(O)-alkyl; "alkanoyl" refers to —C(O)-alkyl; "alkoxycarbonyl" refers to —C(O)—O-alkyl.

As used herein, the term "lower alkyl" refers to straight-chain or branched alkyl groups having from 1 to about 8 carbon atoms. Lower alkyl groups and the lower alkyl moiety of lower alkoxy, lower alkanoyloxy, lower alkanoyl, the lower alkoxycarbonyl, non-aromatic heterocycloalkyl, heteroarylalkyl and hydroxyalkyl include, for example, methyl, ethyl, propyl, isopropyl, butyl, isobutyl, sec-butyl, tert-butyl, pentyl, hexyl, heptyl and octyl.

A "cycloalkyl" group is a cyclic alkyl group having from 3 to about 10 carbon atoms, for example, cyclopropyl, cyclobutyl, cyclopentyl, cyclohexyl, cycloheptyl, cyclooctyl, cyclononyl and cyclodecyl.

A "polycycloalkyl" group is a polycyclic alkyl group having from four to about twelve carbon atoms, for example, bicyclo[3.2.1]octyl, bicyclo[4.3.2]undecyl, adamantyl and noradamantyl.

A "lower alkenyl" group is a straight-chain or branched $C_2$ to $C_8$ alkyl group having one or more carbon-carbon double bonds, for example, vinyl, 1-propenyl, allyl, methacryl, 1-butenyl, crotyl, pentenyl, isoprenyl, hexenyl, heptenyl and octenyl.

A "cycloalkenyl" group is a cyclic alkenyl group having from 4 to about 10 carbon atoms, for example, cyclobutenyl, cyclopentenyl, cyclohexenyl, cycloheptenyl, cyclooctenyl, cyclononenyl and cyclodecenyl.

The term "aryl" refers to carbocyclic aromatic groups, including fused polycyclic aromatic ring systems in which a carbocyclic aromatic ring is fused to one or more other carbocyclic aromatic rings. Aryl groups include, for example, phenyl and napthyl.

"Aralkyl" refers to an aryl-alkyl group having from about 7 to about 15 carbon atoms, for example, benzyl, phenethyl, benzhydryl, naphthylmethyl and acenaphthenyl.

The term "heteroaryl" or a "heteroaryl moiety" of the heteroarylalkyl refers to aromatic heterocyclic groups, including fused polycyclic aromatic ring systems in which an aromatic heterocyclic ring is fused to one or more other aromatic rings or aromatic heterocyclic rings, for example, pyridyl, pyrazinyl, pyrimidinyl, pyridazinyl, quinolinyl, isoquinolinyl, phthalazinyl, quinazolinyl, quinoxalinyl, naphthyridinyl, pyrrolyl, pyrazolyl, imidazolyl, triazolyl, tetrazolyl, thienyl, furyl, thiazolyl, oxazolyl, indolyl, indazolyl, benzimidazolyl, benzotriazolyl, purinyl, phenothiazinyl and phenoxazinyl.

A "non-aromatic heterocyclic" group or a "non-aromatic heterocyclo moiety" of the non-aromatic heterocycloalky group is a cycloaliphatic group that contains one or more heteroatoms, such as nitrogen, oxygen and sulfur. A non-aromatic heterocyclic group can be unsubstituted or can be substituted with a suitable substituent. Suitable substituents for a non-aromatic heterocyclic group include those substituents described herein, including fused aromatic or non-aromatic rings. Non-aromatic heterocyclic groups which are suitable for use in the invention include, for example, pyrrolidinyl, piperidino, piperazinyl, morpholino, thiomorpholino, homopiperidino, homopiperazinyl, tetrahydropyridinyl, tetrahydroquinolinyl, tetrahydroisoquinolinyl, pyrrolinyl, indolinyl, benzimidazolin-2-on-1-yl, imidazolin-2-on-1-yl, piperazin-2-on-4-yl, piperazine-2,3-dion-1-yl, piperazine-2,5-dion-1-yl, 1-methylpiperazin-4-yl, 1-(2-hydroxyethyl)piperazin-4-yl, 1-(3-hydroxypropyl)piperazin-4-yl, 1-benzylpiperazin-4-yl, dioxanyl, dioxolanyl, tetrahydropyranyl, succinimido and phthalimido.

A "heterocyclic group containing at least one nitrogen atom" can be an aromatic group or a cycloaliphatic group, and includes fused polycyclic ring systems in which a ring containing at least one nitrogen atom is fused to one or more other rings. Examples of heterocyclic groups which contain at least one nitrogen atom include, pyrrolidinyl, piperidino, piperazinyl, morpholino, thiomorpholino, homopiperidino, homopiperazinyl, tetrahydropyridinyl, tetrahydroquinolinyl, tetrahydroisoquinolinyl, pyrrolinyl, indolinyl, benzimidazolin-2-on-1-yl, imidazolin-2-on-1-yl, piperazin-2-on-4-yl, piperazine-2,3-dion-1-yl, piperazine-2,5-dion-1-yl, 1-methylpiperazin-4-yl, 1-(2-hydroxyethyl)piperazin-4-yl, 1-(3-hydroxypropyl)piperazin-4-yl, 1-benzylpiperazin-4-yl, imidazolidyl, imidazolyl, benzimidazolyl, azabenzimidazolyl, succinimido, phthalimido and the like.

A "cyclic group" is a group containing at least one cyclic ring, and includes those as described above, for example, cycloalkyl groups, polycycloalkyl groups, cycloalkenyl groups, aryl groups, heteroaryl groups, non-aromatic heterocyclic groups, and heterocyclic groups containing at least one nitrogen atom.

The halogen includes a fluorine, chlorine, bromine and iodine atom.

Suitable substituents on lower alkyl, cycloalkyl, polycycloalkyl, lower alkenyl, cycloalkenyl, aryl, aralkyl, heteroaryl, heteroarylalkyl, non-aromatic heterocyclic group, lower alkoxy, lower alkanoyl, lower alkanoyloxy, lower alkoxycarbonyl, heterocyclic group containing at least one nitrogen atom or cyclic group include, for example, halogen, —CN, —NO$_2$, —CF$_3$, hydroxy, oxo, lower alkyl, cycloalkyl, lower alkoxy, lower alkanoyl, lower alkoxycarbonyl, aryl, aralkyl, heteroaryl, non aromatic heterocycloalkyl, heteroarylalkyl, non-aromatic heterocycloalkyl, hydroxyalkyl, —COOR$^{17a}$, —NR$^{17a}$R$^{17b}$ and —CONR$^{17a}$R$^{17b}$.

R$^{17a}$ and R$^{17b}$ are each, independently, hydrogen, lower alkyl, cycloalkyl, aryl, or aralkyl; or R$^{17a}$ and R$^{17b}$ taken together with the nitrogen atom to which they are bonded form a heterocyclic group containing at least one nitrogen atom).

When a ring (e.g., cycloalkyl, polycycloalkyl, cycloaklenyl, aryl, heteroaryl, aralkyl, heteroarylalkyl, non-aromatic heterocyclic group, heterocyclic group containing at least one nitrogen atom, cyclic group) is substituted with one or more other rings, the rings can be fused. For example, when a phenyl ring is substituted with dioxolane the rings can be fused to create a benzodioxolanyl group. The substituted groups described herein can have one or more substituents.

When a group is substituted with two substituents, the two substituents taken together can form —OCH$_2$O—.

In a preferred embodiment, W is a bond or —O—; X$^1$ and X$^2$ are —CN; R$^{2a}$, R$^{2b}$, R$^{3a}$, R$^{3b}$, R$^{4a}$, R$^{4b}$, R$^{5a}$, R$^{5b}$, R$^{6a}$, and R$^{6b}$ are hydrogen; and n is 1. Additionally, Q is hydrogen, substituted or unsubstituted cycloalkyl, substituted or unsubstituted lower alkenyl, or substituted or unsubstituted lower alkynyl; W is at the para- or meta-position of the benzene ring from the —CR$^{6a}$R$^{6b}$— group; R$^7$, R$^8$, R$^9$, and R$^{10}$ are hydrogen; q is 0, 1, 2, 3, 4, 5, or 6; R$^1$ is substituted or unsubstituted aryl, substituted or unsubstituted heteroaryl, substituted or unsubstituted aralkyl, or substituted or unsubstituted heteroarylalkyl; or Y is a bond, —C(=O)— or —CH$_2$—.

Physiologically or pharmaceutically acceptable salts of Compounds (I) include acceptable acid addition salts, metal salts, ammonium salts, and organic amine addition salts. Pharmaceutically or physiologically acceptable acid addition salts of Compounds (I) include inorganic acid addition salts such as hydrochloride, sulfate, nitrate, phosphate and the like, and organic acid addition salts such as acetate, maleate, fumarate, citrate and the like. Pharmaceutically or physiologically acceptable metal salts include alkali metal salts such as sodium salt and potassium salt, alkaline earth metal salts such as magnesium salt and calcium salt, aluminum salt, zinc salt and the like. Pharmaceutically or physiologically acceptable ammonium salts include ammonium, tetramethylammonium and the like; and pharmaceutically or physiologically acceptable organic amine addition salts include addition salts with morpholine, piperidine and the like.

The compounds described herein can be prepared by the synthetic processes shown in FIGS. 1 to 10 described below, or by other suitable methods.

FIG. 1 is a schematic diagram showing the preparation of compounds represented by Structural Formula (IV) by Process 1.

Step 1-1:

In FIG. 1, step 1-1, L$^1$ is a suitable leaving group, such as a sulfonate group (e.g., p-toluenesulfonyloxy or methanesulfonyloxy) or a halogen atom (e.g., chlorine, bromine or iodine). The other symbols are as described above.

Compound (IV) can be obtained by alkylating Compound (II), which can be prepared using suitable methods. For example, Compound (II) can be prepared by the methods disclosed in U.S. Pat. No. 5,075,301, JP91-163074, JP92-279581 and JP93-17471 the entire teachings of each of the foregoing are incorporated herein by reference. U.S. Pat. No. 5,075,301, JP91-163074, JP92-279581 and JP93-17471 disclose dicyanodiaminoethylene derivatives which inhibit acetylcholinesterases and exhibit gastrointestinal motility enhancing activity.

The alkylation reaction is carried out in an inert solvent in the presence of a suitable base at a temperature between about −50° C. and the boiling point of the employed solvent for about 5 minutes to about 48 hours.

Bases which are suitable for use in the alkylation reaction include, for example, sodium hydride, potassium hydride, sodium hydroxide, potassium hydroxide, sodium carbonate, potassium carbonate, sodium methoxide, potassium ethoxide, potassium tert-butoxide, butyl lithium, lithium diisopropylamide, triethylamine, tributylamine, N-methylmorpholine, diazabicycloundecene, and diazabicyclononene.

Inert solvents which are suitable for use in the alkylation reaction include, for example, tetrahydrofuran, dioxane, methanol, ethanol, 2-propanol, 1-butanol, dichloromethane, toluene, benzene, hexane, dimethyl sulfoxide, and dimethylformamide.

Step 1-2:

In FIG. 1, step 1-2, $L^1$ is a hydroxyl group. The other symbols are as described above.

Compound (IV) can also be prepared by condensing Compound (II) and Compound (III) under the Mitsunobu reaction conditions (Carey, F. A. and Sundberg, R. J., *Advanced Organic Chemistry* (3rd ed.), Ed. Plenum, New York (1990)). For example, Compound (II) and Compound (III) are allowed to react in a suitable inert solvent maintained under an atmosphere of a suitable inert gas in the presence of triphenylphosphine and diethyl azodicarboxylate at a temperature between about −50° C. and about room temperature for about 5 minutes to about 48 hours.

Inert solvents which are suitable for use in the condensation reaction include, for example, tetrahydrofuran, dioxane, dichloromethane, toluene, and benzene.

Inert gases which are suitable for use in the condensation reaction include, for example, argon, helium, and nitrogen.

Figure 2:
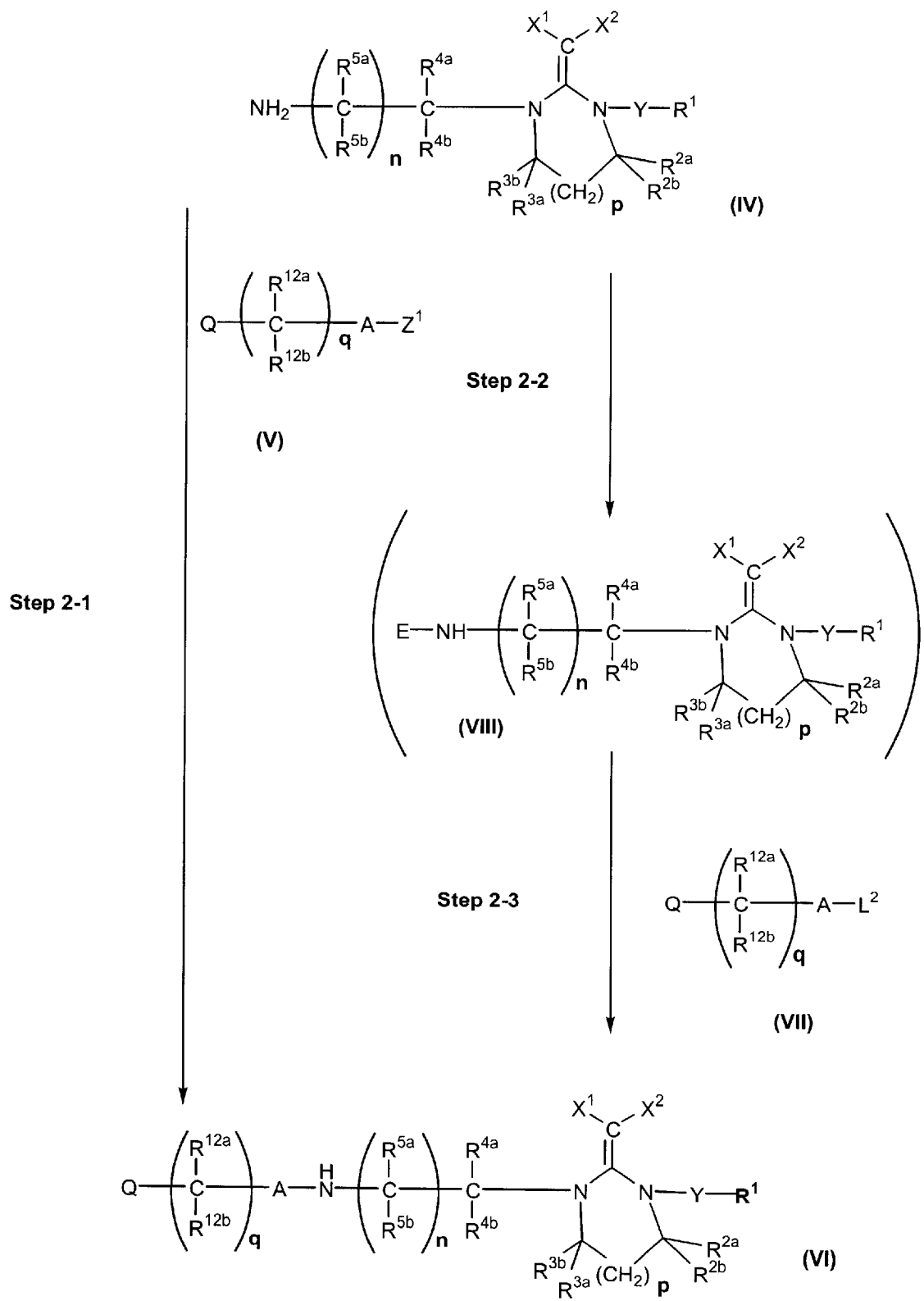
FIG. 2 is a schematic diagram showing the preparation of compounds represented by Structural Formula (VI).

FIG. 2 is a schematic diagram showing the preparation of compounds represented by Structural Formula (VI) by Process 2. In FIG. 2, $Z^1$ is an aldehyde group or a ketone group, $L^2$ is a suitable leaving group, such as a sulfonate group (e.g., p-toluenesulfonyloxy or methanesulfonyloxy) or a halogen atom (e.g., chlorine, bromine or iodine) and E is a protective group for a nitrogen atom. The other symbols are as described above.

Step 2-1:

Compound (VI) can be prepared by alkylating Compound (IV) prepared in step 1-1 or 1-2 in a conventional manner. Various known methods for alkylation of nitrogen can be used (see, for example, *Jikken Kagaku Koza* (4th ed.), Vol. 20, p. 300, Maruzen (1990)). For example, when A is a bond and $R^{12b}$ is hydrogen, Compound (IV) can be allowed to react with Compound (V) in an inert solvent, and the product can be allowed to react with a suitable reducing agent at a temperature between about −78° C. and the boiling point of the employed solvent for about 5 minutes to about 48 hours to give Compound (VI).

Inert solvents which are suitable for use in the alkylation reaction include, for example tetrahydrofuran, dioxane, diethyl ether, ethylene glycol, dichloromethane, chloroform, methanol, ethanol, butanol, isopropyl alcohol, benzene, toluene, and water.

Reducing agents which are suitable for use in the alkylation reaction include, for example, lithium aluminum hydride, sodium bis(2-methoxyethoxy)aluminum hydride, potassium borohydride, sodium borohydride, sodium triacetoxyborohydride, sodium cyanoborohydride, a borane-dimethyl sulfide complex, a borane-dimethylamine complex, and diisobutylaluminum hydride.

Step 2-2:

Compound (VI) can be prepared by alkylating Compound (IV) prepared in step 1-1 or 1-2 in a conventional manner (see, for example, *Jikken Kagaku Koza* (4th ed.), Vol. 20, p. 296, Maruzen (1990)). For example, Compound (IV) and Compound (VII) can be allowed to react in a suitable inert solvent in the presence of a suitable base at a temperature between about −50° C. and the boiling point of the employed solvent for about 5 minutes to about 48 hours. If desired, Compound (IV) can be once protected with a suitable protective group (Greene, T. W. and Wuts, P. G. M., *Protective Groups in Organic Synthesis* (2nd ed.), John Wiley & Sons, Inc., New York (1991)) and, after the reaction with Compound (VII), the protective group can be removed to give Compound (VI).

Bases and inert solvents suitable for use in the alkylation reaction are those described herein, in the description of step 1-1.

Protective groups which are suitable for use in the alkylation reaction include, for example, tert-butyloxycarbonyl, tosyl, 2,4-dinitrobenzenesulfonyl, acetyl and the like.

Figure 3:
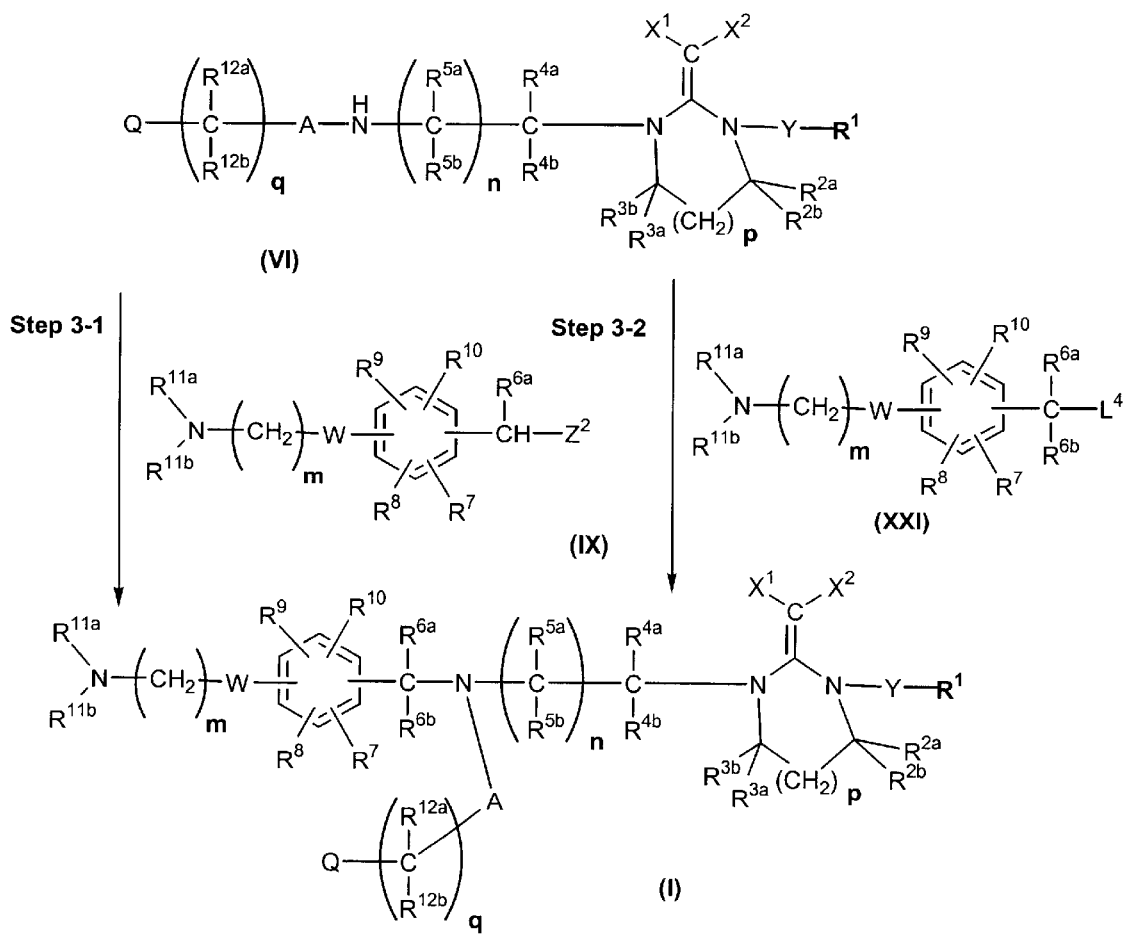
FIG. 3 is schematic diagram showing the preparation of compounds represented by Structural Formula (I).

FIG. 3 is a schematic diagram showing the preparation of compounds represented by Structural Formula (I) by Process 3. In FIG. 3, $Z^2$ is an aldehyde group or a ketone group, $L^4$ is a suitable leaving group, such as, a sulfonate group (e.g., p-toluenesulfonyloxy or methanesulfonyloxy) or a halogen atom (e.g., chlorine, bromine or iodine). The other symbols are as described above.

Step 3-1:

When $R^{6b}$ is hydrogen, Compound (I) can be obtained by alkylating Compound (VI) prepared in step 2-1 or 2-2 with Compound (IX). For example, Compound (VI) can be allowed to react with an equivalent to large excess of Compound (IX) in an inert solvent and then to react with a suitable reducing agent at a temperature between about −78° C. and the boiling point of the employed solvent for about 5 minutes to about 48 hours to prepare Compound (I).

Inert solvents and reducing agents suitable for use in the alkylation reaction are those described herein, in the description of step 2-1.

Step 3-2:

Compound (I) can be obtained by alkylating Compound (VI) prepared in step 2-1 or 2-2 with Compound (XXI) as described in step 1-1.

Figure 4:
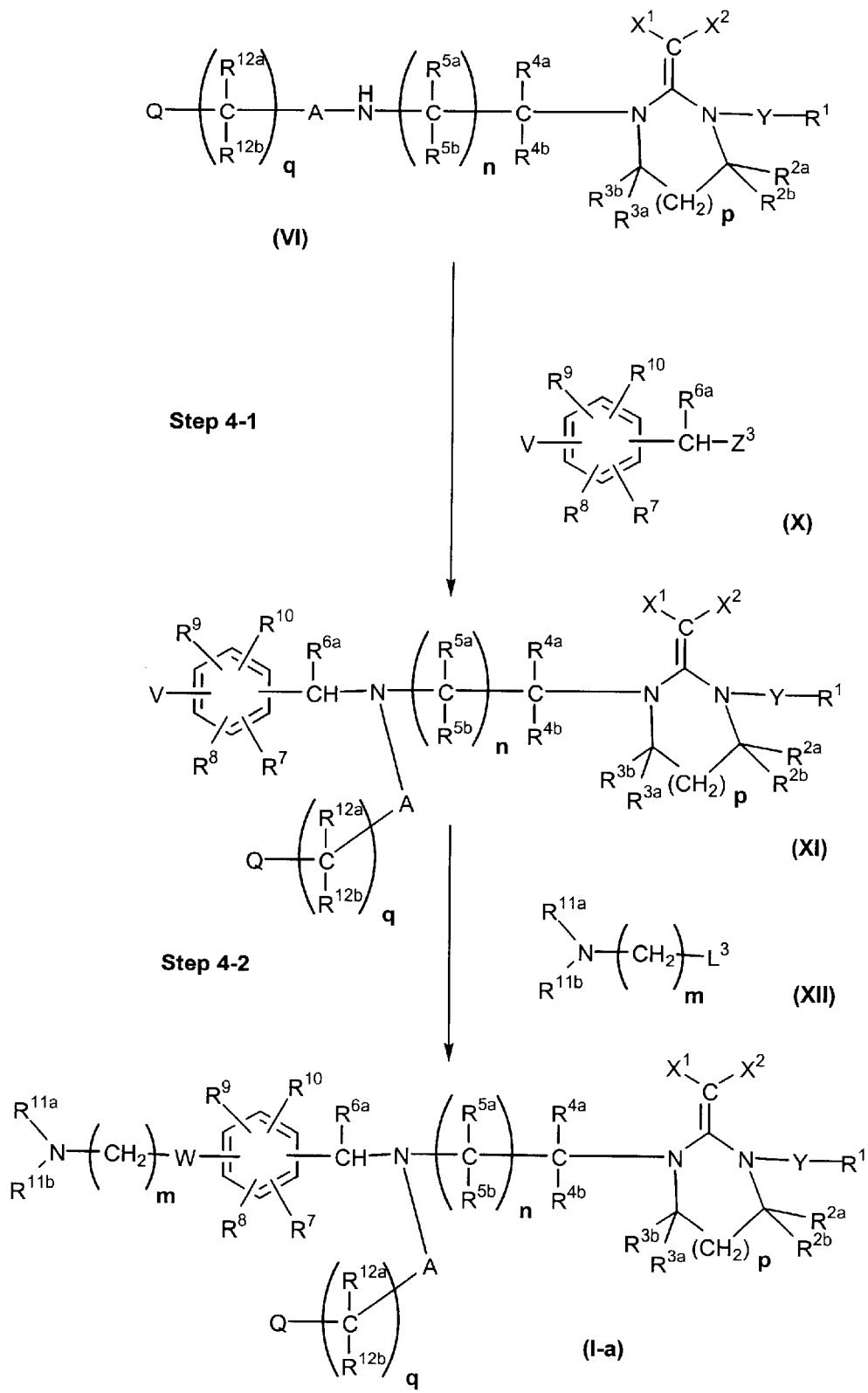
FIG. 4 is schematic diagram showing the preparation of compounds represented by Structural Formula (I-a).

FIG. 4 is a schematic diagram showing the preparation of compounds represented by Structural Formula (I-a) by process 4. In FIG. 4, $Z^3$ is an aldehyde group or a ketone group; V is —OH, —SH, or —NHR$^{13}$ (wherein R$^{13}$ has the same meaning as defined above) and $L^3$ is a suitable leaving group, as described herein. The other symbols are as described above.

Step 4-1:

Compound (XI) can be prepared from Compound (IV) obtained in step 2-1 or 2-2 as described in step 3-1.

Step 4-2:

When W is —O—, —S—, or —NR$^{13}$ (wherein R$^{13}$ has the same meaning as defined above), Compound (I-a), which is Compound (I) wherein $R^{12b}$ is hydrogen, can be obtained by alkylating Compound (XI) obtained in step 4-1 with Compound (XII). For example, Compound (XI) and Compound (XII) can be allowed to react in an inert solvent in the presence of a suitable base at a temperature between about −50° C. and the boiling point of the employed solvent for about 5 minutes to about 48 hours.

Bases and inert solvents suitable for use in the alkylation reaction are those described herein, in the description of step 1-1.

Figure 5:
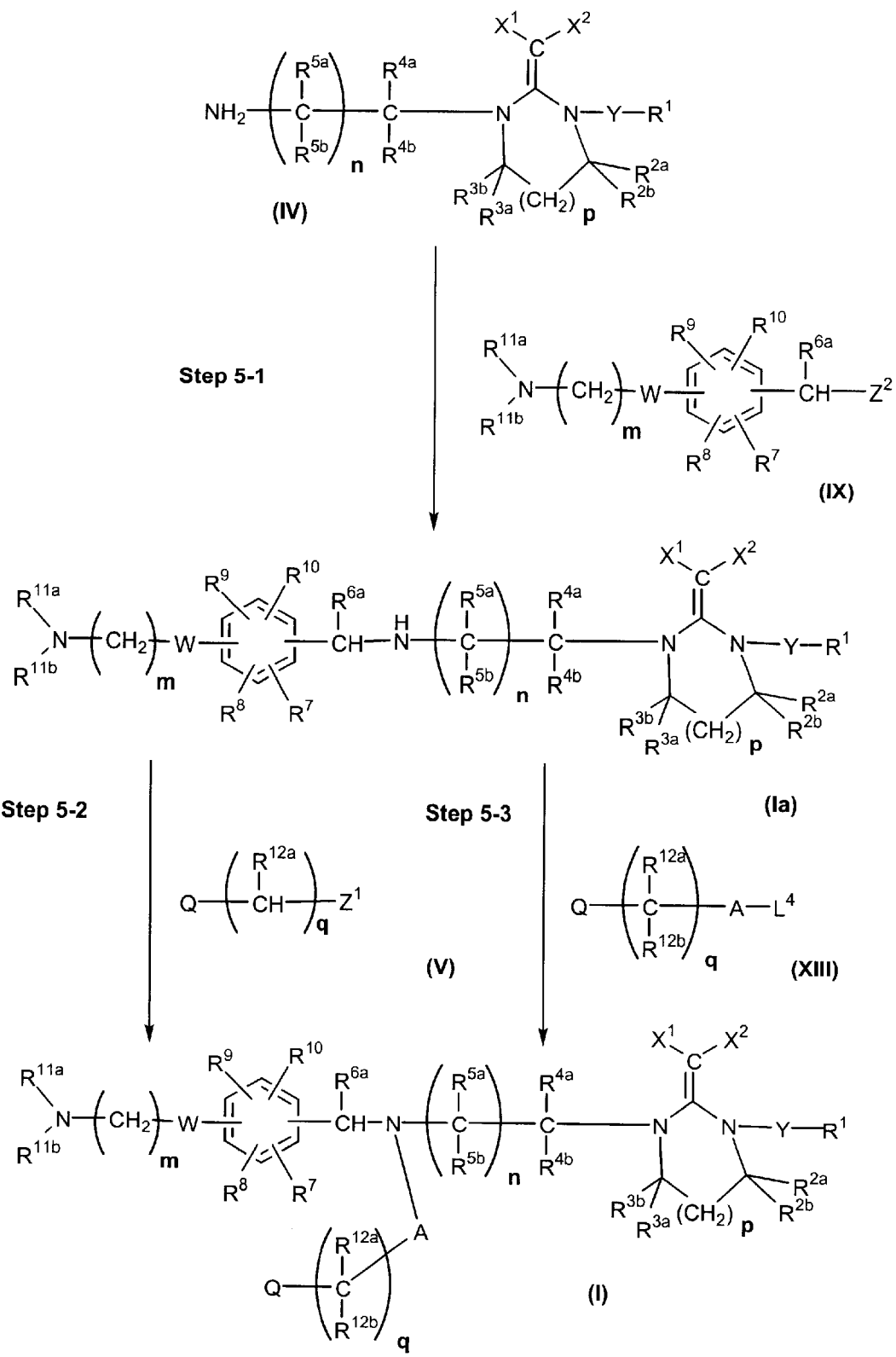
FIG. 5 is schematic diagram showing the preparation of compounds represented by Structural Formula (I).

FIG. 5 is a schematic diagram showing the preparation of compounds represented by Structural Formula (I) by process 5. In FIG. 5, $L^4$ is a suitable leaving group, such as a halogen atom (e.g., chlorine, bromine or iodine) or a corresponding acid anhydride residue. The other symbols are as described above.

Step 5-1:

Compound (Ia) can be prepared from Compound (IV) obtained in step 1-1 or 1-2 and Compound (IX) as described in step 3-1.

Step 5-2:

When A is a bond and $R^{12b}$ is hydrogen, Compound (I) can be prepared from Compound (Ia) obtained in step 5-1 and Compound (V) as described in step 2-1.

Step 5-3:

Compound (I) can be obtained by acylation or sulfonylation of Compound (Ia) obtained in step 5-1 with Compound (XIII). A variety of methods suitable for acylation or sulfonylation of an amine compound can be used (see, for example, *Jikken Kagaku Koza* (4th ed.), Vol. 23, p. 137, Maruzen (1990)). For example, Compound (Ia) and Compound (XIII) can be allowed to react in an inert solvent in the presence or absence of a suitable base at a temperature between about −40° C. and the boiling point of the employed solvent for about 5 minutes to about 48 hours.

Inert solvents suitable for use in the acylation or sulfonylation reaction include, for example, tetrahydrofuran, dioxane, diethyl ether, dichloromethane, chloroform, dimethylformamide, tert-butanol, benzene, toluene, dimethyl sulfoxide, and ethyl acetate.

Bases suitable for use in the acylation or sulfonylation reaction include, for example, pyridine, polyvinylpyridine, dimethylaminopyridine, triethylamine, sodium hydride, and sodium hydroxide.

Figure 6:
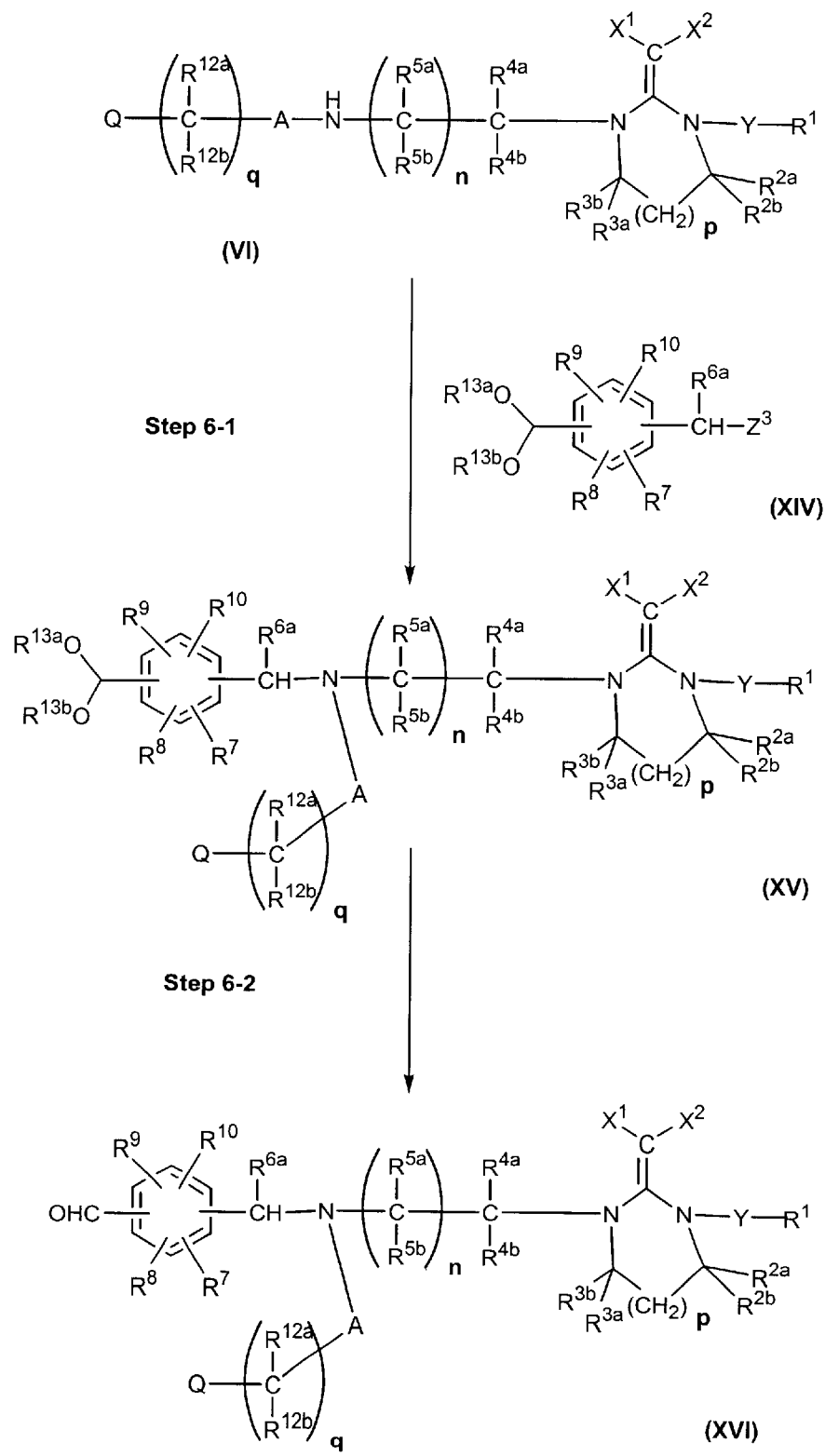
FIG. 6 is schematic diagram showing the preparation of compounds represented by Structural Formula (XVI).

FIG. 6 is a schematic diagram showing the preparation of compounds represented by Structural Formula (XVI) by process 6. In FIG. 6, $R^{13a}$ and $R^{13b}$ are each, independently, a lower alkyl group, or $R^{13a}$ and $R^{13b}$ taken together form an alkylene group (e.g., ethylene, propylene or butylene). The other symbols are as described above.

Step 6-1:

Compound (XV) can be prepared by reacting Compound (VI) obtained in step 2-1 or 2-2 with Compound (XIV) as described in step 3-1.

Step 6-2:

Compound (XVI) can be prepared by removing the protective group from Compound (XV) obtained in step 6-1. A variety of suitable reactions for removing a protective group from an acetal or a ketal can be applied (Greene, T. W. and Wuts, P. G. M., *Protective Groups in Organic Synthesis* (2nd ed.), John Wiley & Sons, Inc., New York (1991)). For example, Compound (XV) can be allowed to react with an excess of acid in a suitable solvent at a temperature between about −78° C. and the boiling point of the employed solvent for about 5 minutes to about 48 hours.

Solvents which are suitable for use in the deprotection reaction include, for example, water and acetone.

Acids which are suitable for use in the deprotection reaction include, for example, hydrochloric acid, acetic acid, and toluenesulfonic acid.

Figure 7:
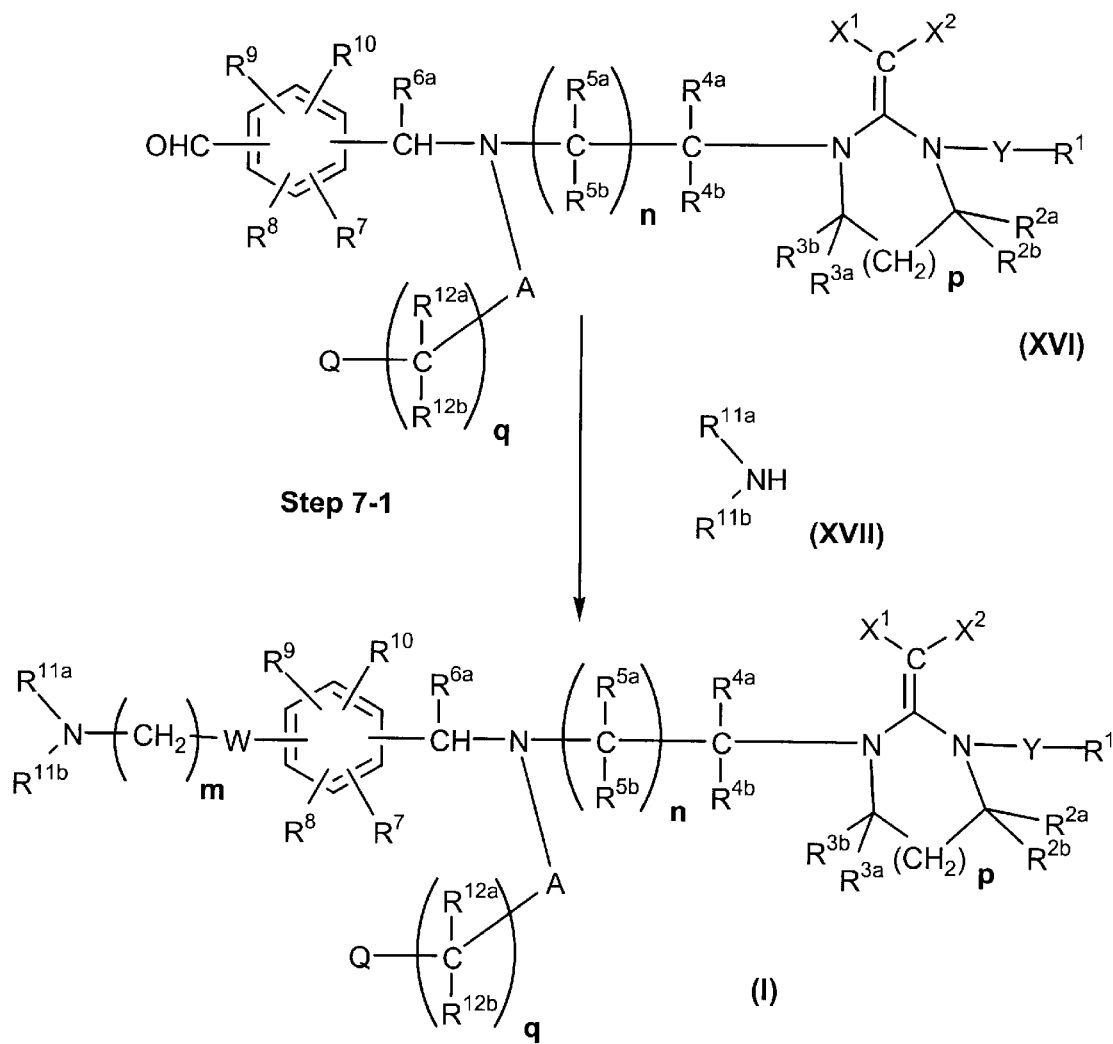
FIG. 7 is schematic diagram showing the preparation of compounds represented by Structural Formula (I).

FIG. 7 is a schematic diagram showing the preparation of compounds represented by Structural Formula (I) by process 7. In FIG. 7 the symbols are as described above.

Step 7-1:

When m is 1, and W is a bond, Compound (I) can be prepared by reacting Compound (XVI) obtained in step 6-2 and Compound (XVII) as described in step 3-1.

Figure 8:
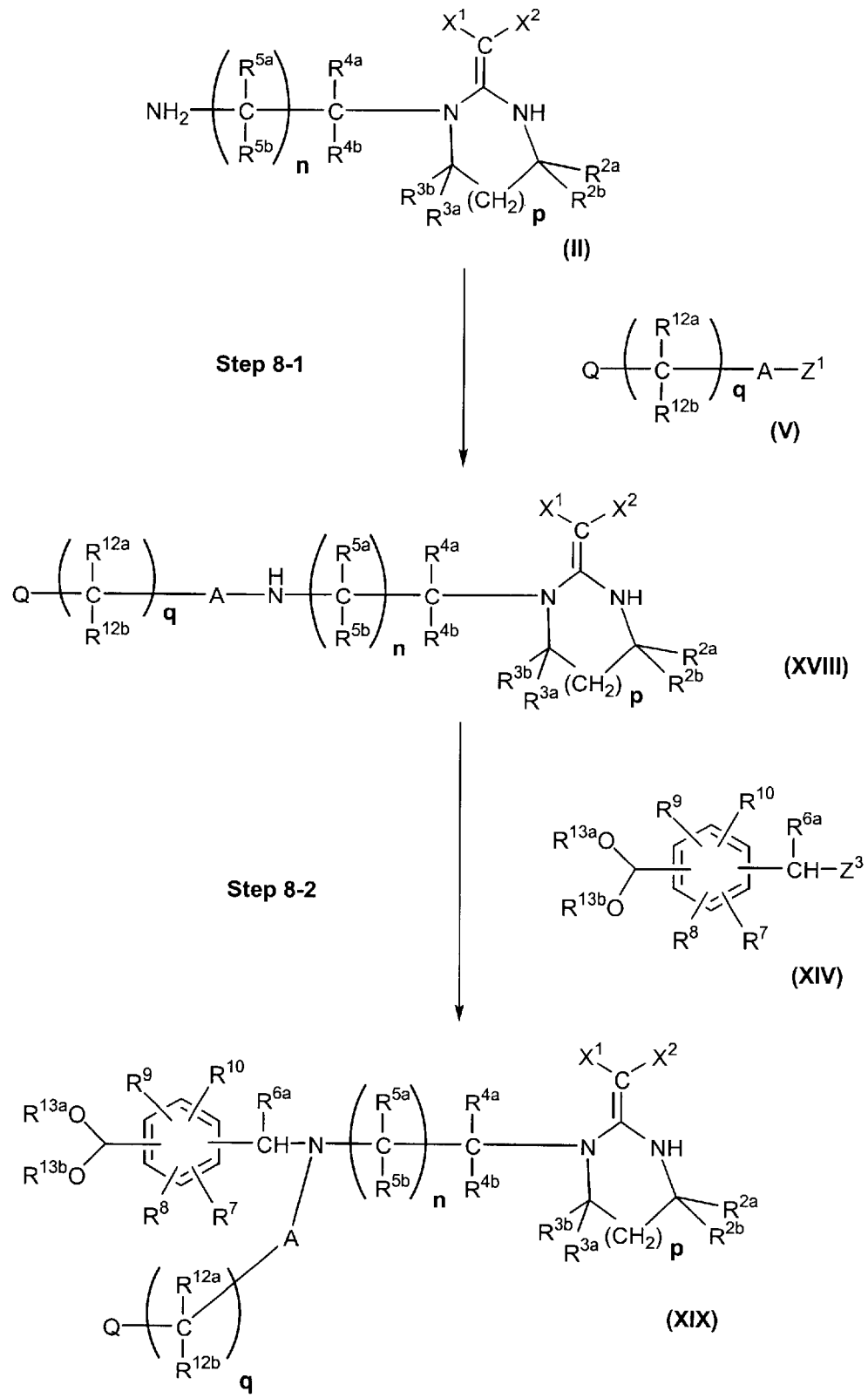
FIG. 8 is schematic diagram showing the preparation of compounds represented by Structural Formula (XIX).

FIG. 8 is a schematic diagram showing the preparation of compounds represented by Structural Formula (XIX) by process 8. In FIG. 8, $R^{6b}$ is hydrogen and the other symbols are as described above.

Step 8-1:

Compound (XVIII) can be prepared by reacting Compound (II) and Compound (V) as described in step 2-1.

Step 8-2:

Compound (XIX) can be prepared by reacting Compound (XVIII) obtained in step 8-1 and Compound (XIV) as described in step 3-1.

Figure 9:
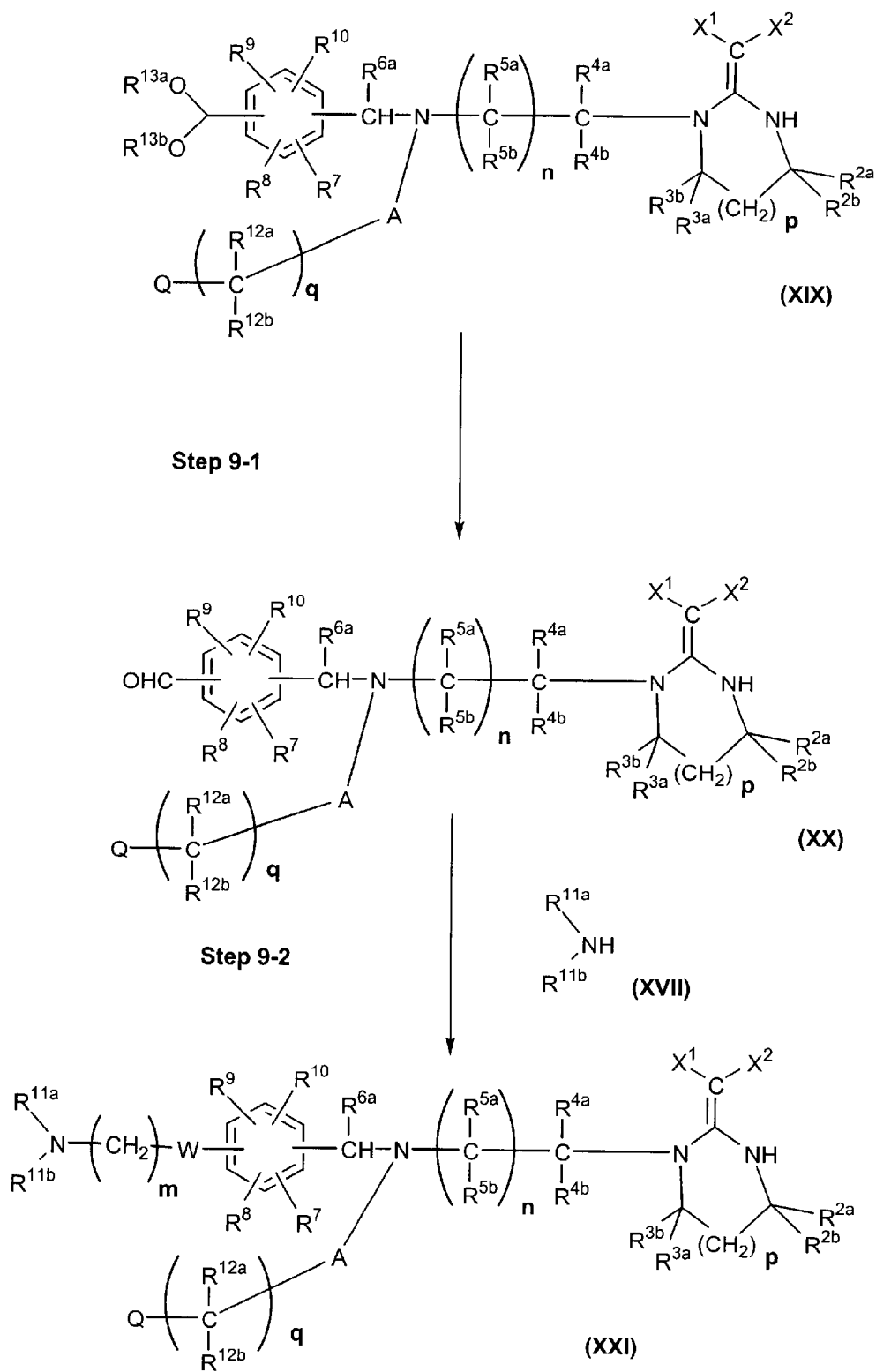
FIG. 9 is schematic diagram showing the preparation of compounds represented by Structural Formula (XXI).

FIG. 9 is a schematic diagram showing the preparation of compounds represented by Structural Formula (XXI) by process 9. In FIG. 9, the symbols are as described above.

Step 9-1:

Compound (XX) can be prepared from Compound (XIX) obtained in step 8-2 as described in step 6-2.

Step 9-2:

When m is 1, and W is a bond, Compound (XXI) can be prepared by reacting Compound (XX) obtained in step 9-1 and Compound (XVII) as described in step 7-1.

Figure 10:
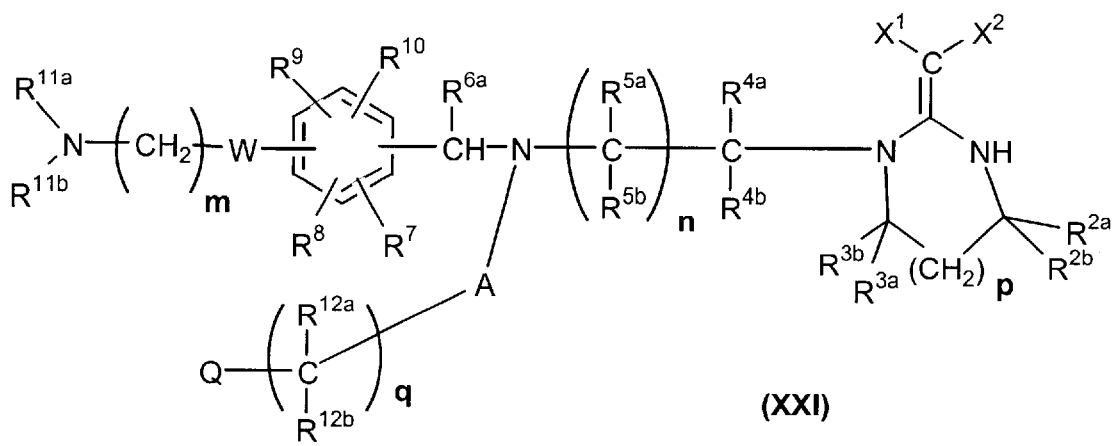
FIG. 10 is schematic diagram showing the preparation of compounds represented by Structural Formula (I).
Figure 10:
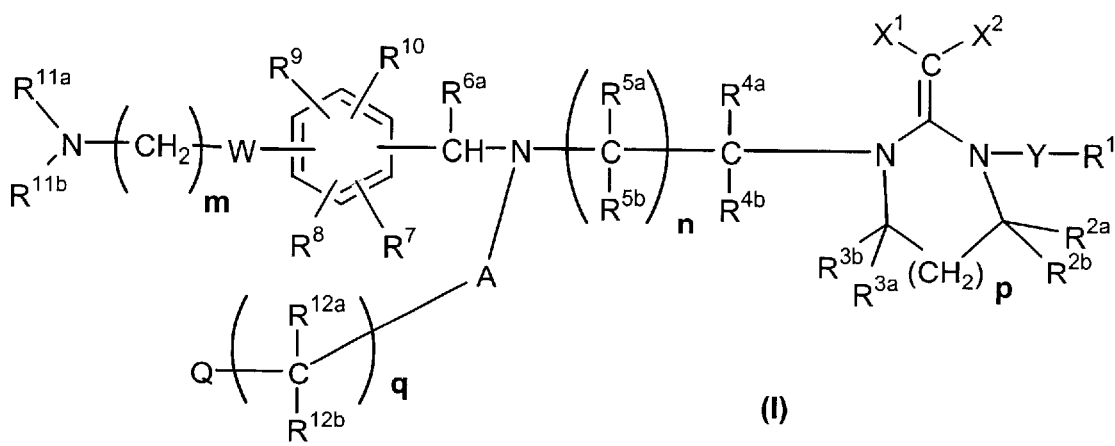

FIG. 10 is a schematic diagram showing the preparation of compounds represented by Structural Formula (I) by process 10. In FIG. 10, the symbols are as described above.

Step 10-1:

Compound (I) can be prepared by reacting Compound (XXI) obtained in step 9-2 and Compound (III) as described in step 1-2.

Figure 11:
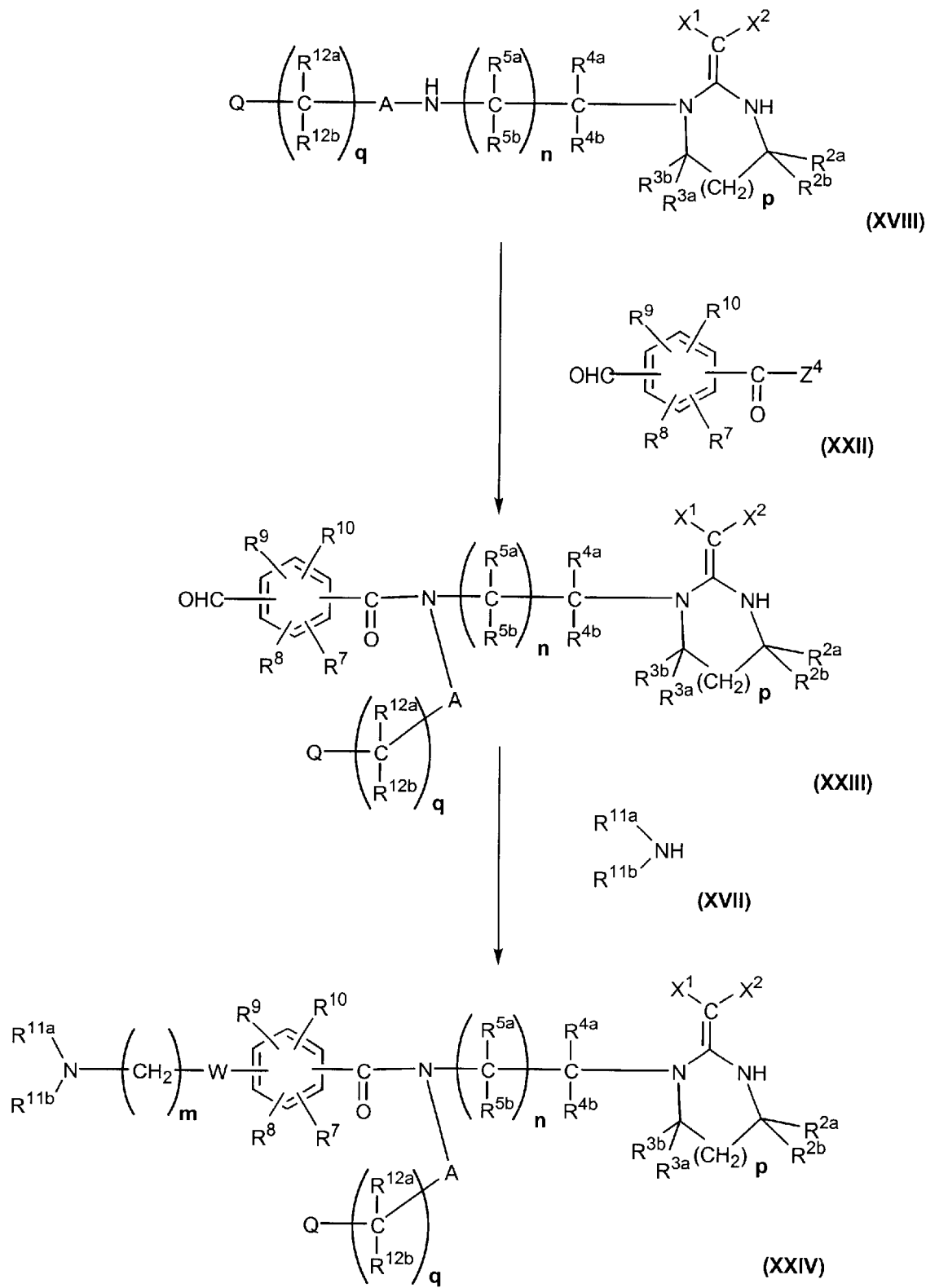
FIG. 11 is schematic diagram showing the preparation of compounds represented by Structural Formula (XXIV).

FIG. 11 is a schematic diagram showing the preparation of compounds represented by Structural Formula (XXIV) by process 11. In FIG. 11, $Z^4$ is a hydroxyl group or a halogen atom. The other symbols are as described above.

Step 11-1:

Compound (XXIII) can be prepared by allowing Compound (XVIII) obtained in step 8-1 and Compound (XXII) to react in an organic solvent in the presence of a condensing agent and a base at 0 to 50° C. for 5 minutes to 48 hours. Suitable organic solvents include tetrahydrofuran, dioxane, dichloromethane, N,N-dimethylformamide, and dimethyl sulfoxide.

Suitable condensing agents include dicyclohexylcarbodiimide, 1-(3-dimethylaminopropyl)-3-ethylcarbodiimide, cyanide diethylphosphate, and benzotriazol-1-yloxy-tris(dimethylamino)phosphonium hexafluorophosphate.

Suitable bases include triethylamine, diisopropylethylamine, N-methyhnorpholine, 1-hydroxy-7-azabenzotriazole, and 1-hydroxybenzotriazole.

Step 11-2:

When m is 1, and W is a bond, Compound (XXIV) can be prepared from Compound (XXIII) obtained in step 11-1 and Compound (XVII) as described in step 3-1.

Figure 12:
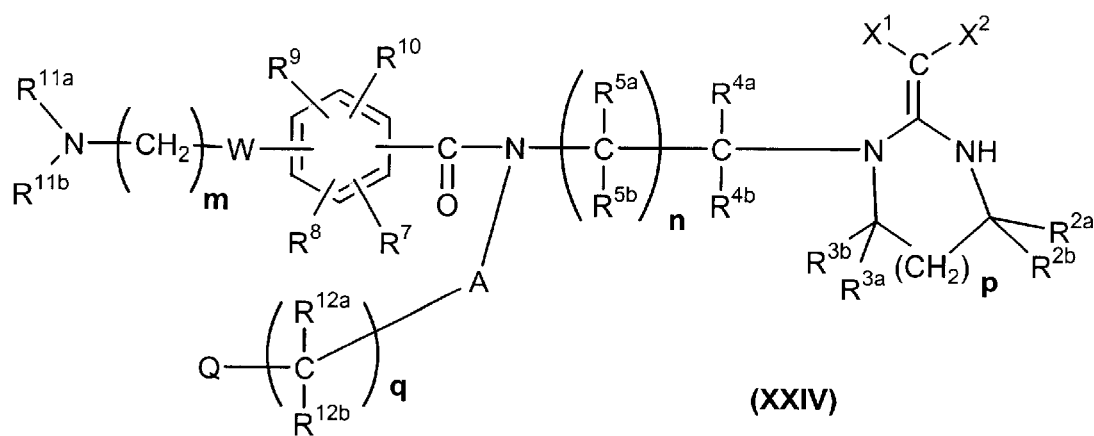
FIG. 12 is schematic diagram showing the preparation of compounds represented by Structural Formula (Ib).
Figure 12:
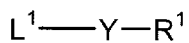
Figure 12:
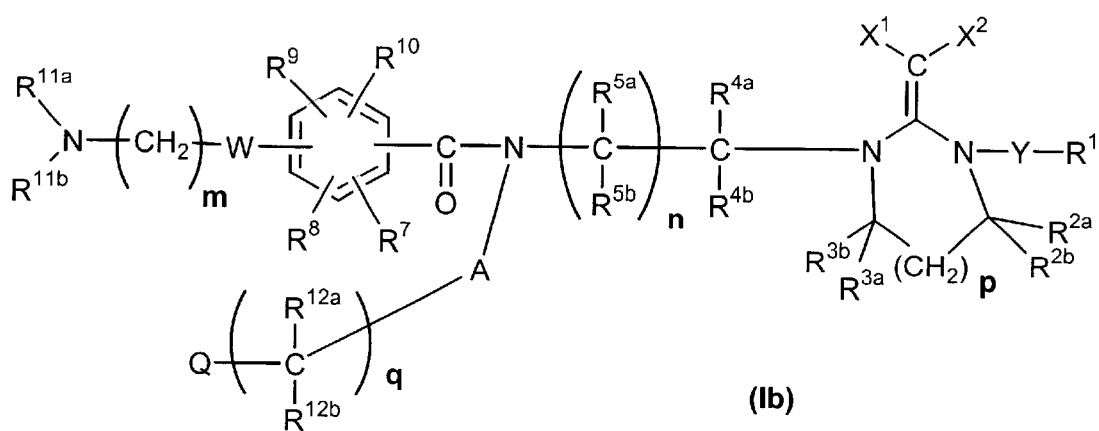

FIG. 12 is a schematic diagram showing the preparation of compounds represented by Structural Formula (Ib) by process 12.

Step 12-1:

In FIG. 12, step 12-1, $L^1$ is a suitable leaving group. The other symbols are as described above. Compound (Ib) can be prepared from Compound (XXIV) obtained in step 11-2 and Compound (I) as described in step 1-1.

Step 12-2:

In FIG. 12, step 12-2, $L^1$ is a hydroxyl group. The other symbols are as described above.

Compound (Ib) can also be prepared from Compound (XXIV) obtained in step 11-2 and Compound (III) as described in step 1-2.

Figure 13:
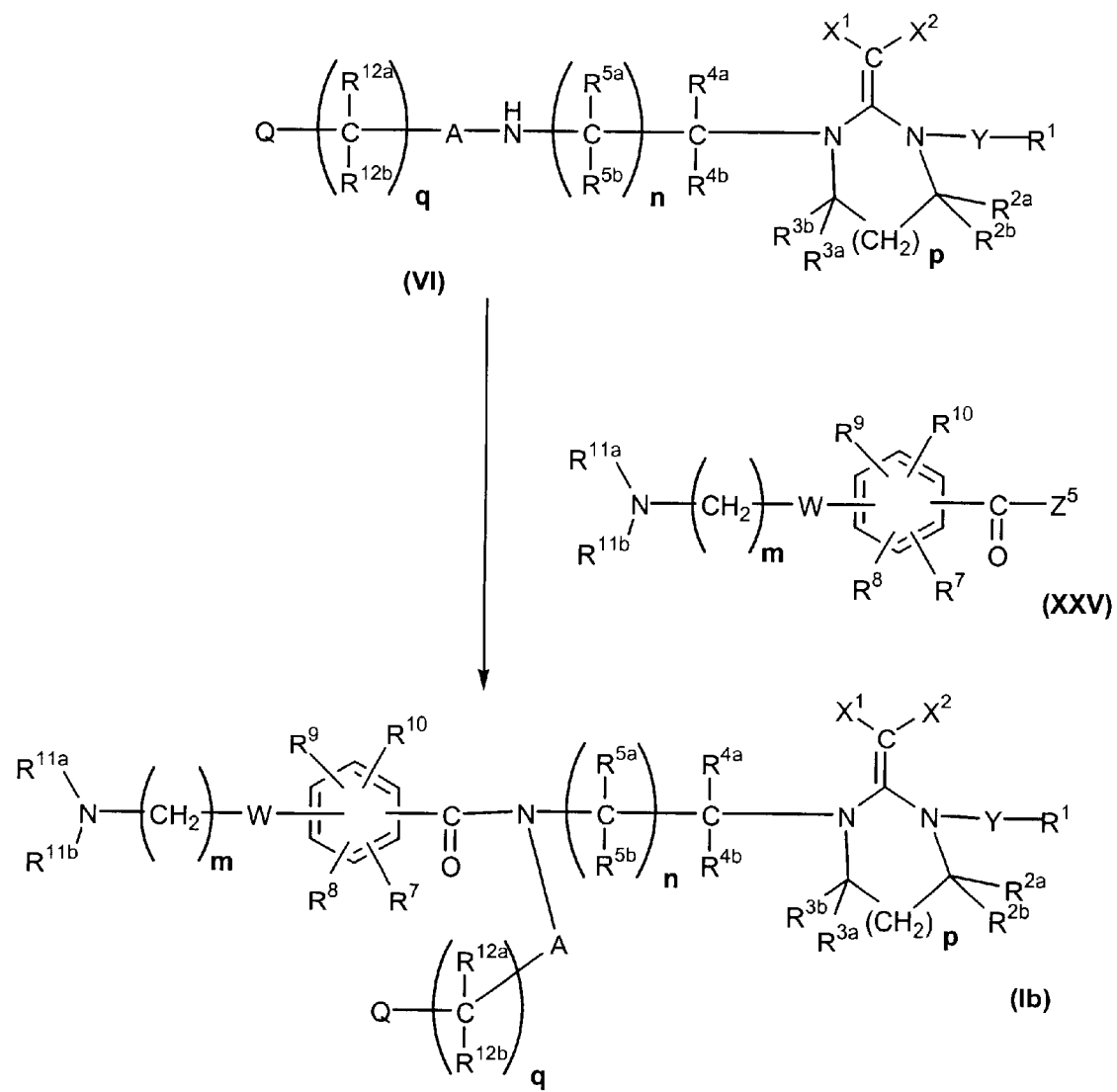
FIG. 13 is schematic diagram showing the preparation of compounds represented by Structural Formula (Ib).

FIG. 13 is a schematic diagram showing the preparation of compounds represented by Structural Formula (Ib) by process 13. In FIG. 13, $Z^5$ is a hydroxyl group or a halogen atom The other symbols are as described above.

Step 13-1:

Compound (Ib) can also be prepared from Compound (VI) obtained in step 2-1 or step 2-2 and Compound (XXV) as described in step 11-1.

The intermediates and the desired compounds produced by the processes described herein can be isolated using suitable methods, for example, filtration, extraction, washing, drying, concentration, recrystallization and various kinds of chromatography. The intermediates can also be subjected to subsequent reactions without isolation.

The compounds of the invention can be produced as a salt or as free compounds. The desired salt of a compound of the invention can be prepared by dissolving or suspending the compound in a suitable solvent and adding a suitable acid or base to the solution, thereby forming a salt. When the compound is produced as a salt, it can be purified as such.

Compound (I) and pharmaceutically acceptable salts thereof may be in the form of adducts with water or various solvents, which are also within the scope of the present invention.

The activity of the compounds of the present invention can be assessed using a suitable assay, such as a receptor binding assay, a chemotaxis assays, an extracellular acidification assay or a calcium flux assay (see, for example, Hesselgesser et al., *J. Biol. Chem.* 273(25):15687–15692 (1998) and WO 98/02151). For example, as described herein, small organic molecule antagonists of CXCR3/IP-10 binding have been identified utilizing cells engineered to express recombinant human CXCR3 (CXCR3.L1/2) and which bind $^{125}$I-IP-10 and chemotax in response to IP-10, Mig or I-TAC. Specifically, a high through-put receptor binding assay, which monitors $^{125}$I-IP-10 binding to CXCR3.L1/2 cell membranes, was used to identify small molecule antagonists which block binding of IP-10, Mig or I-TAC to CXCR3.

The activity of the compounds can also be assessed by monitoring cellular responses induced by active receptor, using suitable cells expressing receptor. For instance, exocytosis (e.g., degranulation of cells leading to release of one or more enzymes or other granule components, such as esterases (e.g., serine esterases), perforin, and/or granzymes), inflammatory mediator release (such as release of bioactive lipids such as leukotrienes (e.g., leukotriene $C_4$)), and respiratory burst, can be monitored by methods known in the art or other suitable methods (see e.g., Taub, D. D. et al., *J. Immunol.*, 155: 3877–3888 (1995), regarding assays for release of granule-derived serine esterases; Loetscher et al., *J. Immunol.*, 156: 322–327 (1996), regarding assays for enzyme and granzyme release; Rot, A. et al., *J. Exp. Med.*, 176: 1489–1495 (1992) regarding respiratory burst; Bischoff, S. C. et al., *Eur. J. Immunol.*, 23: 761–767 (1993) and Baggliolini, M. and C. A. Dahinden, *Immunology Today*, 15: 127–133 (1994)).

In one embodiment, an antagonist of CXCR3 is identified by monitoring the release of an enzyme upon degranulation or exocytosis by a cell capable of this function. Cells expressing CXCR3 can be maintained in a suitable medium under suitable conditions, and degranulation can be induced. The cells are contacted with an agent to be tested, and enzyme release can be assessed. The release of an enzyme into the medium can be detected or measured using a suitable assay, such as in an immunological assay, or biochemical assay for enzyme activity.

The medium can be assayed directly, by introducing components of the assay (e.g., substrate, co-factors, antibody) into the medium (e.g., before, simultaneous with or after the cells and agent are combined). The assay can also be performed on medium which has been separated from the cells or further processed (e.g., fractionated) prior to assay. For example, convenient assays are available for enzymes, such as serine esterases (see e.g., Taub, D. D. et al., *J. Immunol.*, 155: 3877–3888 (1995) regarding release of granule-derived serine esterases).

In another embodiment, cells expressing CXCR3 are combined with a ligand of CXCR3 (e.g., IP-10, Mig, I-TAC) or promoter of CXCR3 function, a compound to be tested is added before, after or simultaneous therewith, and degranulation is assessed. Inhibition of ligand- or promoter-induced degranulation is indicative that the compound is an inhibitor of mammalian CXCR3 function (a CXCR3 antagonist).

Therapeutic Applications

The compounds of the present invention are useful in the treatment of certain diseases or conditions (e.g., autoimmune, inflammatory, infectious, cancer). Modulation of mammalian CXCR function according to the present invention, through the inhibition or promotion of at least one function characteristic of a mammalian CXCR protein, provides an effective and selective way of inhibiting or promoting receptor-mediated functions. As CXC-chemokine receptors selectively expressed on activated lymphocytes, responsive to chemokines such as IP-10, Mig or I-TAC whose primary targets are lymphocytes, particularly effector cells such as activated or stimulated T lymphocytes and NK cells, mammalian CXCR3 proteins provide a target for selectively interfering with or promoting lymphocyte function in a mammal, such as a human. Once lymphocytes are recruited to a site, other leukocyte types, such as monocytes, may be recruited by secondary signals. Thus, agents which inhibit or promote CXCR3 function, including inhibitors (antagonists) and/or promoters (agonists), such as the compounds described herein, can be used to modulate leukocyte function (e.g., leukocyte infiltration including recruitment and/or accumulation), particularly of lymphocytes, for therapeutic purposes.

In one aspect, the present invention provides a method of modulating (inhibiting or promoting) an inflammatory response in an individual in need of such therapy, comprising administering an agent which inhibits or promotes mammalian CXCR3 function to an individual in need of such therapy. In one embodiment, a compound which inhibits one or more functions of a mammalian CXCR3 protein (e.g., a human CXCR3) is administered to inhibit (i.e., reduce or prevent) inflammation. For example, the small organic molecules of the present invention, including Compound 1 can be used in the method. As a result, one or more inflammatory processes, such as leukocyte emigration, chemotaxis, exocytosis (e.g., of enzymes) or inflammatory mediator release, can be inhibited. For example, leukocytic infiltration of inflammatory sites (e.g., in a delayed-type hypersensitivity response) can be inhibited according to the present method. The inflammation can be acute or chronic and can be a consequence of an autoimmune disease, allergic reaction, infection (e.g., bacterial, viral, fungal, parasitic) or trauma (e.g., ischemia/reperfusion injury), for example.

In another embodiment, a compound which promotes one or more functions (e.g., receptor agonist) of a mammalian CXCR3 protein (e.g., a human CXCR3) is administered to induce (trigger or enhance) an inflammatory response, such as leukocyte emigration, chemotaxis, exocytosis (e.g., of enzymes) or inflammatory mediator release, resulting in the beneficial stimulation of inflammatory processes. For example, natural killer cells can be recruited to combat viral infections or neoplastic disease.

In another embodiment, the present invention is a method of treating (e.g., palliative therapy, curative therapy, maintenance therapy, prophylactic therapy) an individual having a disease associated with pathogenic leukocyte recruitment and/or activation. The method comprises administering a compound which inhibits mammalian CXCR3 function (e.g., a compound of Structural Formula I or physiologically or pharmaceutically acceptable salt thereof) to an individual in need of such therapy. Where the individual has a relapsing or chronic condition, an effective amount of an a compound which inhibits mammalian CXCR3 function (e.g., a compound of Structural Formula I or physiologically or pharmaceutically acceptable salt thereof) can be administered to treat the condition, and therapy can be continued (maintenance therapy) with the same or different dosing as indicated, to inhibit relapse or renewed onset of symptoms.

The term "individual" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species. Diseases and conditions associated with inflammation, infection, and cancer can be treated using the method. In a preferred embodiment, the disease or condition is one in which the actions of lymphocytes, particularly effector cells such as activated or stimulated T lymphocytes and natural killer (NK) cells, are to be inhibited or promoted for therapeutic and/or prophylactic purposes. In a particularly preferred embodiment, the inflammatory disease or condition is a T cell-mediated disease or condition.

Diseases or conditions, including chronic diseases, of humans or other species which can be treated with inhibitors of CXC chemokine receptor 3 (CXCR3) function, include, but are not limited to:

inflammatory or allergic diseases and conditions, including systemic anaphylaxis or hypersensitivity responses, drug allergies (e.g., to penicillin, cephalosporins), insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, or other autoimmune conditions);

autoimmune diseases, such as arthritis (e.g., rheumatoid arthritis, psoriatic arthritis, juvenile rheumatoid arthritis, polyarthritis, spondyloarthropathy), multiple sclerosis, systemic lupus erythematosus, myasthenia gravis, diabetes, including diabetes mellitus and juvenile onset diabetes, glomerulonephritis and other nephritides, autoimmune thyroiditis, Behcet's disease;

graft rejection (e.g., in transplantation), including allograft rejection, xenograft rejection or graft-versus-host disease;

other diseases or conditions in which undesirable inflammatory responses are to be inhibited can be treated, including, but not limited to, atherosclerosis, restenosis, cytokine-induced toxicity, myositis (including polymyositis, dermatomyositis);

diseases in which angiogenesis or neovascularization plays a role, including neoplastic disease (e.g., tumor formation and growth), retinopathy (e.g., retinopathy of prematurity, diabetic retinopathy), retinal vein occlusion, macular degeneration (e.g., age-related macular degeneration), hemangiomas, arthritis (e.g., rheumatoid arthritis) and psoriasis.

Diseases or conditions of humans or other species which can be treated with a promoter (e.g., an agonist) of CXC chemokine receptor 3 (CXCR3) function, include, but are not limited to:

cancers, particularly those with leukocytic infiltration of the skin or organs such as cutaneous T cell lymphoma (e.g., mycosis fungoides);

diseases in which angiogenesis or neovascularization plays a role, including neoplastic disease, retinopathy (e.g., diabetic retinopathy), and macular degeneration;

infectious diseases, such as bacterial infections and tuberculoid leprosy, and especially viral infections;

immunosuppression, such as that in individuals with immunodeficiency syndromes such as AIDS, individuals undergoing radiation therapy, chemotherapy, or other therapy which causes immunosuppression; immunosuppression due congenital deficiency in receptor function or other causes. Promoters of CXCR3 function can also have protective effects useful to combat stem cell depletion during cancer chemotherapy (Sarris, A. H. et al., *J. Exp. Med.*, 178: 1127–1132 (1993)).

Modes of Administration

According to the method, one or more compounds can be administered to an individual by an appropriate route, either alone or in combination with another drug. A therapeutically effective amount of an agent (e.g., a small organic molecule which inhibits ligand binding) is administered. A "therapeutically effective amount" of a compound is an amount which is sufficient to achieve a desired therapeutic and/or prophylactic effect, such as an amount which results in the prevention or a decrease in the severity of symptoms associated with an inflammatory disease or condition. For example, an effective amount of an antagonist of CXCR3 function is an amount sufficient to inhibit a (i.e., one or more) function of CXCR3 (e.g., ligand (e.g., IP-10, Mig, I-TAC) bindind, ligand-induced leukocyte migration, ligand-induced integrin activation, ligand-induced transient increases in the concentration of intracellular free calcium $[Ca^{2+}]_i$ and ligand-induced granule release of proinflammatory mediators).

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, a therapeutically effective amount of the compound can range from about 0.1 mg per day to about 100 mg per day for an adult. Preferably, the dosage ranges from about 1 mg per day to about 100 mg per day. An antagonist of chemokine receptor function can also be administered in combination with one or more additional therapeutic agents, e.g., theophylline, β-adrenergic bronchdilators, corticosteroids, antihistamines, antiallergic agents, immunosuppressive agents and the like.

The compound of the invention can be administered by any suitable route, including, for example, orally in capsules, suspensions or tablets or by parenteral administration. Parenteral administration can include, for example, intramuscular, intravenous, subcutaneous, intrathecal or intraperitoneal administration. The compound can also be administered orally (e.g., dietary), transdermally, topically, by inhalation (e.g., intrabronchial, intranasal, oral inhalation or intranasal drops) or rectally. Administration can be local or systemic as indicated. The preferred mode of administration can vary depending upon the particular disease or condition to be treated, however, oral or parenteral administration is generally preferred.

The compound can be administered to the individual in conjunction with a physiologically or pharmaceutically acceptable carrier as part of a pharmaceutical composition for treatment or prevention of inflammation, an inflammatory disease or other disease (e.g., an autoimmune disease), as described herein. Formulation of a compound to be administered will vary according to the route of administration selected (e.g., solution, emulsion, capsule). Suitable physiologically or pharmaceutically acceptable carriers may contain inert ingredients which do not interact with the compound. Standard pharmaceutical formulation techniques can be employed, such as those described in Remington's Pharmaceutical Sciences, Mack Publishing Company, Easton, Pa. Suitable physiologically or pharmaceutically acceptable carriers for parenteral administration include, for example, sterile water, physiological saline, bacteriostatic saline (saline containing about 0.9% benzyl alcohol), phosphate-buffered saline, Hank's solution, Ringer's-lactate and the like. Methods for encapsulating compositions (such as in a coating of hard gelatin or cyclodextran) are known in the art (Baker et al., *Controlled Release of Biological Active Agents*, John Wiley and Sons, 1986).

The compounds of the present invention can also be administered to treat a inflammatory and/or autoimmune diseases or conditions in combination with a variety of other anti-inflammatory and/or immunosuppressive drugs, such as cyclosporin A, rapamycin, steroids (e.g., prednisone, methylpednisolone), azothioprine, methotrexate, or FK506 (tacrolimus). Such combination therapy can result in more efficacious therapy with reduced doses of the anti-inflammatory or immunosuppressive drugs. The ability to reduce the dose of the anti-inflammatory or immunosuppressive drug can greatly benefit the patient as many of these drugs have severe and well-known side effects (Spencer, C. M. et al. *Drugs*, 54(6):925–975 (1997); *Physicians Desk Reference*, 53rd Edition, Medical Economics Co., pp. 2081–2082 (1999)).

The invention is illustrated by the following Examples and Test Example which are not intended to be limiting in any way.

EXEMPLIFICATION

Example 1

1-[2-{N-Ethyl-N-(4-dimethylaminobenzyl) amino}ethyl]-3-(1-naphthylmethyl)-2-imidazolidinylidenepropanedinitrile (Compound 1)

In 4 ml of tetrahydrofuran were dissolved 200 mg of Compound (I) obtained in Reference Example 1 and 270 mg of 4-dimethylaminobenzaldehyde, and 380 mg of sodium triacetoxyborohydride was added thereto, followed by stirring at room temperature for 20 minutes. An aqueous solution of sodium bicarbonate was added to the reaction mixture, and the mixture was extracted with chloroform. The extract was washed with a saturated aqueous solution of sodium chloride, dried over potassium carbonate, and evaporated to remove the solvent. The residue was purified by silica gel column chromatography (hexane:ethyl acetate= 1:2 to 0:1) to give 280 mg (98%) of Compound 1 as a colorless oily substance.

$^1$H NMR (270 MHz, DMSO-d$_6$) δ: 8.0–7.4 (7H, m), 7.23 (2H, d, J=7.9 Hz), 6.69 (2H, d, J=7.9 Hz), 5.21 (2H, s), 3.8–3.4 (6H, m), 3.0–2.7 (10H, m), 1.16 (3H, t, J=7.3 Hz). MASS (m/z) 478 (M$^+$).

Example 2

1-[2-{N-Ethyl-N-(4-piperidinomethylbenzyl) amino}ethyl]-3-(1-naphthylmethyl)-2-imidazolidinylidenepropanedinitrile (Compound 2)

Compound (I) (200 mg) obtained in Reference Example 1 and 610 mg of Compound (XIII) obtained in Reference Example 13 were allowed to react as described in Example 1, and the product was recrystallized in acetone in the form of an oxalate to give 310 mg (71%) of Compound 2 as colorless crystals.

$^1$H NMR (270 MHz, CDCl$_3$) δ: 7.9–7.8 (3H, m), 7.6–7.2 (8H, m), 5.17 (2H, s), 3.62 (2H, t, J=5.9 Hz), 3.56 (2H, s), 3.42 (2H, s), 3.4–3.1 (4H, m), 2.74 (2H, t, J=5.9 Hz), 2.60 (2H, q, J=6.9 Hz), 2.33 (4H, brs), 1.53 (4H, brs), 1.42 (2H, brs), 1.12 (3H, t, J=6.9 Hz). MASS (m/z) 532 (M$^+$); Elemental Analysis: $C_{34}H_{40}N_6 \cdot 1.5C_2H_2O_4 \cdot 2.0H_2O$;

| Found (%) | C:63.38, H:6.49, N:11.72 |
| Calculated (%) | C:63.30, H:6.72, N:11.97 |

Example 3

1-[2-{N-Ethyl-N-{4-(2-piperidinoethoxy) benzyl}amino}ethyl]-3-(1-naphthylmethyl)-2-imidazolidinylidenepropanedinitrile (Compound 3)

In 5 ml of dimethylformamide were dissolved 91 mg of Compound (II) obtained in Reference Example 2 and 45 mg of 1-(2-chloroethyl)piperidine hydrochloride, and 30 mg of sodium ethoxide was added to the solution at 0° C. After the mixture was stirred at 65° C. for 2 hours, an aqueous solution of sodium bicarbonate was added, and the reaction mixture was extracted with chloroform. The extract was washed with a saturated aqueous solution of sodium chloride, dried over potassium carbonate, and evaporated to remove the solvent. The residue was purified by silica gel column chromatography (chloroform:methanol=10:1) to give 86 mg (76%) of Compound 3 as a colorless oily substance.

$^1$H NMR (270 MHz, CDCl$_3$) δ: 7.9–7.4 (7H, m), 7.15 (2H, d, J=8.6 Hz), 6.79 (2H, d, J=8.6 Hz), 5.14 (2H, s), 4.01 (2H, t, J=5.9 Hz), 3.59 (2H, t, J=5.8 Hz), 3.49 (2H, s), 3.4–3.0 (4H, m), 2.8–2.5 (10H, m), 1.60 (4H, brs), 1.44 (2H, m), 1.11 (3H, t, J=6.9 Hz).

Example 4

1-[2-{N-Ethyl-N-{4-(2-(1-pyrrolidinyl)ethoxy) benzyl}amino}ethyl]-3-(1-naphthylmethyl)-2-imidazolidinylidenepropanedinitrile (Compound 4)

Compound (II) (100 mg) obtained in Reference Example 2 and 45 mg of 1-(2-chloroethyl)pyrrolidine hydrochloride were allowed to react as described in Example 3 to give 57 mg (47%) of Compound 4 as a colorless oily substance.

$^1$H NMR(270 MHz, CDCl$_3$) δ: 7.9–7.4 (7H, m), 7.15 (2H, d, J=8.6 Hz), 6.80 (2H, d, J=8.6 Hz), 5.14 (2H, s), 4.07 (2H, t, J=5.9 Hz), 3.59 (2H, t, J=5.6 Hz), 3.49 (2H, s), 3.4–3.0 (4H, m), 2.91 (2H, t, J=5.6 Hz), 2.71 (2H, t, J=5.9 Hz), 2.7–2.5 (6H, m), 1.80 (4H, brs), 1.12 (3H, t, J=7.1 Hz). MASS (m/z) 548 (M$^+$).

Example 5

1-[2-{N-Methyl-N-(4-piperidinomethylbenzyl)amino}ethyl]-3-(1-naphthylmethyl)-2-imidazolidinylidenepropanedinitrile (Compound 5)

Compound (III) (150 mg) obtained in Reference Example 3 and 280 mg of Compound (XIII) obtained in Reference Example 13 were allowed to react as described in Example 1 to give 127 mg (54%) of Compound 5 as colorless crystals.

$^1$H NMR (270 MHz, CDCl$_3$) δ: 7.9–7.2 (11H, m), 5.20 (2H, s), 3.70 (2H, t, J=5.9 Hz), 3.52 (2H, s), 3.5–3.1 (6H, m), 2.70 (2H, t, J=5.9 Hz), 2.41 (4H, brs), 2.30 (3H, s), 1.59 (4H, brs), 1.43 (2H, brs). MASS (m/z) 518 (M$^+$); Elemental Analysis: C$_{33}$H$_{38}$N$_6$0.8H$_2$O;

| | |
|---|---|
| Found (%) | C:74.39, H:7.48, N:16.05 |
| Calculated (%) | C:74.35, H:7.49, N:15.76 |

Example 6

1-[2-{N-Methyl-N-(3-piperidinomethylbenzyl)amino}ethyl]-3-(1-naphthylmethyl)-2-imidazolidinylidenepropanedinitrile (Compound 6)

Compound (III) (150 mg) obtained in Reference Example 3 and 280 mg of Compound (XIV) obtained in Reference Example 14 were allowed to react as described in Example 1 to give 111 mg (48%) of Compound 6 as colorless crystals.

$^1$H NMR (270 MHz, CDCl$_3$) δ: 7.9–7.1 (11H, m), 5.20 (2H, s), 3.71 (2H, t, J=5.9 Hz), 3.54 (2H, s), 3.5–3.2 (6H, m), 2.72 (2H, t, J=5.9 Hz), 2.29 (7H, brs), 1.51 (4H, brs), 1.41 (2H, brs). MASS (m/z) 518 (M$^+$); Elemental Analysis: C$_{33}$H$_{38}$N$_6$0.6H$_2$O;

| | |
|---|---|
| Found (%) | C:74.73, H:7.33, N:16.03 |
| Calculated (%) | C:74.85, H:7.46, N:15.87 |

Example 7

1-[2-{N-Ethyl-N-(4-morpholinomethylbenzyl)amino}ethyl]-3-(1-naphthylmethyl)-2-imidazolidinylidenepropanedinitrile (Compound 7)

In 10 ml of tetrahydrofuran were dissolved 200 mg of Compound (IV) obtained in Reference Example 4 and 0.19 ml of morpholine, and 0.25 ml of acetic acid was added to the solution. The mixture was heated at 60° C. for 5 minutes, and 460 mg of sodium triacetoxyborohydride was added thereto at room temperature, followed by stirring at room temperature for 20 minutes. An aqueous solution of sodium bicarbonate was added thereto, and the reaction mixture was extracted with methylene chloride. The extract was dried over potassium carbonate, and the solvent was removed by evaporation. The residue was purified by silica gel column chromatography (chloroform:methanol=30:1) to give 230 mg (100%) of Compound 7 as a colorless oily substance.

$^1$H NMR (270 MHz, CDCl$_3$) δ: 7.9–7.2 (11H, m), 5.17 (2H, s), 3.7–3.6 (6H, m), 3.57 (2H, s), 3.45 (2H, s), 3.4–3.1 (4H, m), 2.76 (2H, t, J=5.9 Hz), 2.59 (2H, q, J=6.9 Hz), 2.40 (4H, m), 1.10 (3H, t, J=6.9 Hz). MASS (m/z) 534 (M$^+$).

Example 8

1-[2-{N-Ethyl-N-(4-(4-methylpiperazinyl)methylbenzyl)amino}ethyl]-3-(1-naphthylmethyl)-2-imidazolidinylidenepropanedinitrile (Compound 8)

Compound (IV) (200 mg) obtained in Reference Example 4 and 0.20 ml of N-methylpiperazine were allowed to react as described in Example 7, to give 220 mg (93%) of Compound 8 as a colorless oily substance.

$^1$H NMR (270 MHz, CDCl$_3$) δ: 7.9–7.2 (11H, m), 5.17 (2H, s), 3.62 (2H, t, J=5.9 Hz), 3.57 (2H, s), 3.46 (2H, s), 3.4–3.1 (4H, m), 2.75 (2H, t, J=5.9 Hz), 2.60 (2H, q, J=6.9 Hz), 2.43 (8H, brs), 2.27 (3H, s), 1.10 (3H, t, J=6.9 Hz). MASS (m/z) 547 (M$^+$).

Example 9

1-[2-{N-Ethyl-N-(4-N,N-dimethylaminomethylbenzyl)amino}ethyl]-3-(1-naphthylmethyl)-2-imidazolidinylidenepropanedinitrile (Compound 9)

Compound (IV) (400 mg) obtained in Reference Example 4 and 176 mg of dimethylamine hydrochloride were allowed to react as described in Example 7, to give 119 mg (28%) of Compound 9. $^1$HNMR (270 MHz, CDCl$_3$) δ: 7.9–7.2 (11H, m), 5.17 (2H, s), 3.62 (2H, t, J=5.9 Hz), 3.57 (2H, s), 3.43 (2H, s), 3.4–3.1 (4H, m), 2.75 (2H, t, J=5.9 Hz), 2.60 (2H, q, J=6.9 Hz), 2.25 (6H, s), 1.11 (3H, t, J=6.9 Hz).

Elemental Analysis: C$_{31}$H$_{36}$N$_6$0.6H$_2$O;

| | |
|---|---|
| Found (%) | C:73.92, H:7.38, N:16.89 |
| Calculated (%) | C:73.95, H:7.45, N:16.69 |

Example 10

1-[2-{N-Ethyl-N-(4-(N-propylamino)methylbenzyl)amino}ethyl]-3-(1-naphthylmethyl)-2-imidazolidinylidenepropanedinitrile (Compound 10)

Compound (IV) (200 mg) obtained in Reference Example 4 and 0.18 ml of n-propylamine were allowed to react as described in Example 7 to give 100 mg (46%) of Compound 10.

$^1$H NMR (270 MHz, CDCl$_3$) δ: 7.9–7.2 (11H, m), 5.7 (2H, s), 3.76 (2H, s), 3.61 (2H, t, J=5.9 Hz), 3.56 (2H, s), 3.4–3.1 (4H, m), 2.74 (2H, t, J=5.0 Hz), 2.60 (4H, m), 1.53 (2H, tq, J=7.3, 7.3 Hz), 1.11 (3H, t, J=6.9 Hz), 0.90 (3H, t, J=7.3 Hz). MASS (m/z) 506 (M$^+$); Elemental Analysis: C$_{32}$H$_{38}$N$_6$0.2H$_2$O;

| | |
|---|---|
| Found (%) | C:75.28, H:7.57, N:16.68 |
| Calculated (%) | C:75.32, H:7.58, N:16.47 |

Example 11

1-[2-{N-Ethyl-(4-(4-(2-hydroxyethyl)piperazinyl)methylbenzyl)amino}ethyl]-3-(1-naphthylmethyl)-2-imidazolidinylidenepropanedinitrile (Compound 11)

Compound (IV) (200 mg) obtained in Reference Example 4 and 0.26 ml of 1-(2-hydroxyethyl)piperazine were allowed to react as described in Example 7 to give 180 mg (72%) of Compound 11 as a colorless oily substance.

$^1$H NMR (270 MHz, CDCl$_3$) δ: 7.9–7.2 (11H, m), 5.17 (2H, s), 3.60 (4H, m), 3.57 (2H, s), 3.46 (2H, s), 3.4–3.1 (4H, m), 2.75 (2H, t, J=5.9 Hz), 2.60 (2H, q, J=7.3 Hz), 2.49 (10H, brs), 1.11 (3H, t, J=7.9 Hz). MASS (m/z) 578 [(M+H)$^+$].

Example 12

1-[2-{N-Acetyl-N-(3-piperidinomethylbenzyl)amino}ethyl]-3-(1-naphthylmethyl)-2-imidazolidinylidenepropanedinitrile (Compound 12)

Compound (V) (26 mg) obtained in Reference Example 5, 0.5 ml of pyridine, and 0.01 ml of acetic anhydride were mixed and stirred at room temperature for 40 minutes. Toluene was added to the reaction mixture, and pyridine was removed azeotropically, and the residue was roughly purified by using an SCX-ion exchange resin (chloroform-methanol-a methanol solution of ammonia) and then further purified by silica gel column chromatography (chloroform:methanol:triethylamine=20:1:0 to 20:1:0.5) to give 27 mg (96%) of Compound 12 as a colorless oily substance.

$^1$H NMR (270 MHz, CDCl$_3$) δ: 7.95–7.05 (11H, m), 5.19 (2H, s), 4.74 (2H, s), 3.85–3.40 (8H, m), 3.36 (2H, dd, J=10.7, 7.8 Hz), 2.37 (4H, m), 2.22 (3H, s), 1.57 (4H, m), 1.44 (2H, m). MASS (m/z) 547 [(M+H)$^+$].

Example 13

1-[2-{N-Benzoyl-N-(3-piperidinomethylbenzyl)amino}ethyl]-3-(1-naphthylmethyl)-2-imidazolidinylidenepropanedinitrile (Compound 13)

Compound (V) (26.1 mg) obtained in Reference Example 5, 0.015 ml of benzoyl chloride, and 0.5 ml of pyridine were allowed to react as described in Example 12, to give 22.8 mg (72%) of Compound 13 as a pale yellow oily substance.

$^1$H NMR (270 MHz, CDCl$_3$) δ: 7.95–7.05 (11H, m), 5.19 (2H, s), 4.73 (2H, s), 4.05–3.20 (10H, m), 2.57 (4H, m), 1.72 (4H, m), 1.50 (2H, m). MASS (m/z) 609 [(M+H)$^+$].

Example 14

1-[2-{N-Furoyl-N-(3-piperidinomethylbenzyl)amino}ethyl]-3-(1-naphthylmethyl)-2-imidazolidinylidenepropanedinitrile (Compound 14)

Compound (V) (10.1 mg) obtained in Reference Example 5, 0.020 ml of 2-furoyl chloride, and 30 mg of polyvinylpyridine were allowed to react as described in Example 12 to give 5.7 mg (48%) of Compound 14 as a pale yellow oily substance.

$^1$H NMR (270 MHz, CDCl$_3$) δ: 7.95–7.10 (12H, m), 7.03 (1H, brs), 6.49 (1H, brs), 5.17 (2H, s), 5.07 (2H, brs), 3.95–3.50 (6H, m), 3.47 (2H, s), 3.31 (2H, m), 2.37 (4H, m), 1.56 (4H, m), 1.44 (2H, m). MASS (m/z) 599 [(M+H)$^+$].

Example 15

1-[2-{N-(2-Thiophenecarbonyl)-N-(3-piperidinomethylbenzyl)amino}ethyl]-3-(1-naphthylmethyl)-2-imidazolidinylidenepropanedinitrile (Compound 15)

Compound (V) (11.0 mg) obtained in Reference Example 5, 0.020 ml of 2-thiophenecarbonyl chloride, and 30 mg of polyvinylpyridine were allowed to react as described in Example 12 to give 6.3 mg (47%) of Compound 15 as a pale yellow oily substance.

$^1$H NMR (270 MHz, CDCl$_3$) δ: 7.95–6.95 (14H, m), 5.19 (2H, s), 5.02 (2H, brs), 4.00–3.55 (6H, m), 3.48 (2H, s), 3.33 (2H, m), 2.37 (4H, m), 1.57 (4H, m), 1.44 (2H, m). MASS (m/z) 615 [(M+H)$^+$].

Example 16

1-[2-{N-Methanesulfonyl-N-(3-piperidinomethylbenzyl)amino}ethyl]-3-(1-naphthylmethyl)-2-imidazolidinylidenepropanedinitrile (Compound 16)

Compound (V) (28.5 mg) obtained in Reference Example 5, 0.010 ml of methanesulfonyl chloride, and 0.50 ml of pyridine were allowed to react as described in Example 12 to give 25.6 mg (76%) of Compound 16 as a pale yellow oily substance.

$^1$H NMR (270 MHz, CDCl$_3$) δ: 7.95–7.05 (11H, m), 5.14 (2H, s), 4.41 (2H, s), 3.70–3.30 (8H, m), 3.16 (2H, dd, J=10.7, 7.8 Hz), 2.84 (3H, s), 2.36 (4H, m), 1.55 (4H, m), 1.43 (2H, m). MASS (m/z) 583 [(M+H)$^+$].

Example 17

1-[2-{N-Ethyl-N-(3-piperidinomethylbenzyl)amino}ethyl]-3-(1-naphthylmethyl)-2-imidazolidinylidenepropanedinitrile (Compound 17)

Compound (V) (18.3 mg) obtained in Reference Example 5 was dissolved in 2 ml of tetrahydrofuran, and 0.015 ml of acetaldehyde, 0.025 ml of acetic acid, and 87 mg of sodium triacetoxyborohydride were added thereto. After the mixture was stirred at room temperature for 30 minutes, a 2 mol/L aqueous solution of potassium hydroxide was added thereto while cooling on an ice bath. The reaction mixture was extracted with chloroform, and the extract was dried over anhydrous magnesium sulfate and evaporated to remove the solvent. The residue was roughly purified by using an SCX-ion exchanger resin (chloroform-methanol-a methanol solution of ammonia) and further purified by silica gel column chromatography (chloroform:methanol:triethylamine=20:1:0 to 20:1:0.05) to give 8 mg (41%) of Compound 17 as a colorless oily substance.

$^1$H NMR (270 MHz, CDCl$_3$) δ: 7.95–7.05 (11H, m), 5.17 (2H, s), 3.75–3.25 (8H, m), 3.14 (2H, dd, J=10.4, 7.4 Hz), 2.77 (2H, t, J=5.9 Hz), 2.59 (2H, q, J=7.2 Hz), 2.34 (4H, m), 1.52 (4H, m), 1.41 (2H, m), 1.11 (3H, t, J=7.2 Hz). MASS (m/z) 533 [(M+H)$^+$].

Example 18

1-[2-{N-Benzyl-N-(3-piperidinomethylbenzyl)amino}ethyl]-3-(1-naphthylmethyl)-2-imidazolidinylidenepropanedinitrile (Compound 18)

Compound (V) (39.8 mg) obtained in Reference Example 5 and 0.015 ml of benzaldehyde were allowed to react as described in Example 17 to give 34.9 mg (74%) of Compound 18 as a pale yellow oily substance.

$^1$H NMR (270 MHz, CDCl$_3$) δ: 7.95–7.05 (16H, m), 5.13 (2H, s), 3.75–3.35 (8H, m) 3.23 (2H, dd, J=10.4, 7.4 Hz), 3.05 (2H, dd, J=10.4, 7.4 Hz), 2.80 (2H, t, J=5.9 Hz), 2.33 (4H, m), 1.52 (4H, m), 1.41 (2H, m). MASS (m/z) 595 [(M+H)$^+$].

Example 19

1-[2-{N,N-Bis(3-piperidinomethylbenzyl)amino}ethyl]-3-(1-naphthylmethyl)-2-imidazolidinylidenepropanedinitrile (Compound 19)

Compound (V) (30.1 mg) obtained in Reference Example 5 and 40.7 mg of Compound (XIV) obtained in Reference Example 14 were allowed to react as described in Example 17 to give 13.0 mg (32%) of Compound 19 as a pale yellow oily substance.

$^1$H NMR (270 MHz, CDCl$_3$) δ: 7.95–7.10 (15H, m), 5.14 (2H, s), 3.70–3.55 (6H, m), 3.48 (4H, s), 3.26 (2H, dd, J=10.6, 7.8 Hz), 3.09 (2H, dd, J=10.6, 7.8 Hz), 2.80 (2H, t, J=5.9 Hz), 2.38 (8H, m), 1.56 (8H, m), 1.43 (4H, m). MASS (m/z) 692 [(M+H)$^+$].

Example 20

1-[2-{N-(4-(1-Piperidinomethyl)benzyl)amino}propyl]-3-(1-naphthylmethyl)-2-imidazolidinylidenepropanedinitrile (Compound 20)

Compound (VI) (205 mg) obtained in Reference Example 6, 101 mg of Compound (XIII) obtained in Reference Example 13, and 314 mg of sodium triacetoxyborohydride were allowed to react in 10 ml of tetrahydrofuran as described in Example 1 to give 30 mg (9%) of Compound 20 as a pale yellow oily substance.

$^1$H NMR (270 MHz, CDCl$_3$) δ: 7.93–7.85 (3H, m), 7.62–7.23 (8H, m), 5.20 (2H, s), 3.78 (2H, s), 3.75–3.62 (2H, m), 3.55 (2H, s), 3.52–3.42 (2H, m), 3.26–3.19 (2H, m), 2.73 (2H, m), 2.46 (4H, brs), 1.96–1.86 (2H, m), 1.65–1.59 (4H, m), 1.47–1.45 (2H, brs). The signal which corresponds to secondary amine was not observed. MASS (m/z) 519 [(M+H)$^+$].

Example 21

1-[2-{N-Ethyl-N-(4-(1-propylaminomethyl)benzyl)amino}ethyl]-3-(3,5-dimethylbenzyl)-2-imidazolidinylidenepropanedinitrile (Compound 21)

In 5 ml of tetrahydrofuran were suspended 166 mg of Compound (VII) obtained in Reference Example 7, 0.133 ml of 3,5-dimethylbenzyl alcohol, and 472 mg of triphenylphosphine, and 414 mg of di-tert-butyl azodicarboxylate was added thereto while cooling with ice, followed by stirring at room temperature for 3 hours. The solvent was removed by evaporation under reduced pressure, and the residue was purified by flash silica gel column chromatography (chloroform:methanol=100:2). The resulting oily substance was recrystallized as an oxalate from ethanol to give 103 mg (36%) of Compound 21 as colorless crystals.

$^1$H NMR (270 MHz, CDCl$_3$) δ: 7.23 (4H, brs), 6.96 (1H, s), 6.87 (2H, s), 4.64 (2H, s), 3.76 (2H, s), 3.60 (2H, t), 3.57 (2H, s), 3.5–3.3 (4H, m), 2.74 (2H, t), 2.6–2.5 (4H, m), 2.31 (6H, s), 1.53 (2H, dt), 1.11 (3H, t), 0.92 (3H, t). The signal which corresponds to secondary amine was not observed. Elemental Analysis: C$_{30}$H$_{40}$N$_6$1.5C$_2$H$_2$O$_4$1.0H$_2$O;

| | |
|---|---|
| Found (%) | C:62.14, H:7.11, N:13.17 |
| Calculated (%) | C:61.89, H:7.04, N:12.99 |

Example 22

1-[2-{N-(4-(1-Propylaminomethyl)benzyl)amino}ethyl]-3-(3,5-dimethylbenzyl)-2-imidazolidinylidenepropanedinitrile (Compound 22)

In 50 ml of tetrahydrofuran were dissolved 0.40 g of Compound (VIII) obtained in step 2 of Reference Example 8, 4.3 g of Compound (IXa) obtained in step 1 of Reference Example 9, and 0.83 ml of acetic acid, and the solution was stirred at 80° C. for 10 minutes. After allowing the mixture to cool, the solvent was removed by evaporation under reduced pressure. The residue was dissolved in 100 ml of ethanol, and 0.39 g of sodium borohydride was added thereto, followed by stirring at the same temperature for 30 minutes. An aqueous solution of sodium bicarbonate was added to the reaction mixture, and the solvent was evaporated under reduced pressure. Water was added to the residue, followed by extraction with chloroform. The extract was dried over anhydrous sodium sulfate, and the solvent was evaporated under reduced pressure. To the residue was added 9.0 ml of trifluoroacetic acid under ice-cooling, and the mixture was stirred at that temperature for 1 hour. The solvent was removed by evaporation under reduced pressure, and the residue was purified by silica gel column chromatography (chloroform:methanol=100:3 to chloroform: methanol: 28% aqueous ammonia=100:5:1) to give 0.30 g (46%) of Compound 22 as a colorless oily substance.

$^1$H NMR (270 MHz, CDCl$_3$) δ: 7.27 (4H, brs), 6.96 (1H, brs), 6.88 (2H, brs), 4.68 (2H, s), 3.80 (2H, s), 3.77 (2H, s), 3.67 (2H, t), 3.64–3.37 (4H, m), 2.94 (2H, t) 2.31 (6H, s), 1.53 (2H, t), 0.92 (3H, t). The signals which correspond to two secondary amines were not observed.

Example 23

1-[2-{N-Ethyl-N-(4-(1-piperidinomethyl)benzyl)amino}ethyl]-3-(3,5-dimethylbenzyl)-2-imidazolidinylidenepropanedinitrile (Compound 23)

In 10 ml of tetrahydrofuran were dissolved 0.50 g of Compound (X) obtained in Reference Example 10 and 0.40 ml of 3,5-dimethylbenzyl alcohol, and 0.67 g of triphenylphosphine and 1.1 ml of a 40% toluene solution of diethyl azodicarboxylate were added thereto under ice-cooling, followed by stirring at room temperature for 2 hours. The solvent was evaporated under reduced pressure, and the residue was purified by silica gel column chromatography (chloroform:methanol=30:1) to give 0.65 g (99%) of Compound 23 as a pale yellow oily substance.

$^1$H NMR (270 MHz, CDCl$_3$) δ: 7.21 (4H, brs), 6.96 (1H, brs), 6.87 (2H, brs), 4.64 (2H, s), 3.65–3.56(4H, m), 3.52–3.41 (4H, m), 3.31–3.24 (2H, m), 2.73 (2H, t), 2.60 (2H, q), 2.35 (4H, m), 2.32 (6H, s), 1.56 (4H, m), 1.42 (2H, m), 1.11 (3H, t). MASS (m/z) 510 (M$^+$).

Example 24

1-[2-{N-Ethyl-N-(4-(1-piperidinomethyl)benzyl)amino}ethyl]-3-(3,5-dichlorobenzyl)-2-imidazolidinylidenepropanedinitrile (Compound 24)

Compound (X) (0.20 g) obtained in Reference Example 10, 0.35 ml of 3,5-dichlorobenzyl alcohol, 0.53 g of triphenylphosphine, and 0.46 g of di-tert-butyl azodicarboxylate were allowed to react in 10 ml of tetrahydrofuran as described in Example 23 to give 0.25 g (89%) of Compound 24 as a pale yellow oily substance.

$^1$H NMR (270 MHz, CDCl$_3$) δ: 7.35–7.19 (5H, m), 7.17 (2H, d), 4.68 (2H, s), 3.61 (2H, t), 3.56–3.48 (4H, m), 3.45 (2H, s), 3.33–3.26 (2H, m), 2.74 (2H, t), 2.61 (2H, q), 2.37 (4H, m), 1.56 (4H, m), 1.43 (2H, m), 1.13 (3H, t).

Example 25

1-[2-{N-Ethyl-N-(4-(1-piperidinomethyl)benzyl)amino}ethyl]-3-(3,5-dimethylbenzoyl)-2-imidazolidinylidenepropanedinitrile (Compound 25)

In 4.0 ml of tetrahydrofuran was dissolved 0.20 g of Compound (X) obtained in Reference Example 10, and 0.085 g of potassium tert-butoxide was added thereto under cooling with ice, followed by stirring for 30 minutes. To the mixture was added 0.13 g of 3,5-dimethylbenzoyl chloride at that temperature, and the mixture was stirred for 15 minutes. An aqueous solution of sodium bicarbonate was added thereto, and the mixture was extracted with chloroform. The extract was washed with a saturated aqueous solution of sodium chloride and dried over anhydrous sodium sulfate. The solvent was removed by evaporation under reduced pressure. The residue was purified by silica gel column chromatography (chloroform:methanol=40:1) to give 0.098 g (37%) of Compound 25 as a pale yellow oily substance.

$^1$H NMR (270 MHz, CDCl$_3$) δ: 7.3–7.2 (7H, m), 3.79 (2H, brt), 3.73 (2H, t), 3.58 (2H, s), 3.50 (2H, brt), 3.44 (2H, s), 2.81 (2H, t), 2.64 (2H, q), 2.36 (6H, s), 2.34 (4H, brs), 1.62 (4H, brs), 1.41 (2H, brs), 1.14 (3H, t). MASS (m/z) 525 [(M+H)$^+$].

Example 26

1-[2-{N-Ethyl-N-(4-(1-piperidinomethyl)benzoyl)amino}ethyl]-3-(3,5-dimethylbenzyl)-2-imidazolidinylidenepropanedinitrile (Compound 26)

In 5.0 ml of N,N-dimethylformamide were added 0.50 g of Compound (IX) obtained in step 2 of Reference Example 9, 0.40 g of 4-piperidinomethylbenzoic acid hydrochloride obtained by the process of JP86-277683, 0.45 g of 1-(3-dimethylaminopropyl)-3-ethylcarbodiimide hydrochloride, and 0.31 g of 1-hydroxybenzotriazole, and the solution was stirred at room temperature for 2 hours. A saturated aqueous solution of sodium bicarbonate was added thereto, and the mixture was extracted with ethyl acetate. The extract was washed with a saturated aqueous solution of sodium chloride and dried over anhydrous sodium sulfate. The solvent was evaporated under reduced pressure, and the residue was purified by silica gel column chromatography (chloroform:methanol=50:1 to 30:1), followed by trituration with diethyl ether to give 0.45 g (56%) of Compound 26 as colorless crystals.

$^1$H NMR (270 MHz, CDCl$_3$) δ: 7.38 (2H, d), 7.33 (2H, d), 6.94 (1H, s), 6.85 (2H, 4.70 (2H, s), 4.03–3.68 (6H, m), 3.60–3.30 (6H, m), 2.40–2.18 (4H, m), 2.28 (6H, s), 1.80–1.30 (6H, m), 1.15 (3H, t). MASS (m/z) 525 [(M+H)$^+$]; Elemental Analysis: C$_{32}$H$_{40}$N$_6$O;

| Found (%) | C:73.26, H:7.71, N:16.28 |
| Calculated (%) | C:73.25, H:7.68, N:16.02 |

Example 27

1-[2-{N-Ethyl-N-(4-(1-piperidinomethyl)benzoyl)amino}ethyl]-3-(1-naphthylmethyl)-2-imidazolidinylidenepropanedinitrile (Compound 27)

Compound (XI) (0.35 g) obtained in step 2 of Reference Example 11, 0.27 g of 1-naphthalenemethanol, 0.45 g of triphenylphosphine, and 0.34 ml of diethyl azodicarboxylate were allowed to react in 7.0 ml of tetrahydrofuran as described in Example 23 to give 0.34 g (73%) of Compound 27 as pale yellow crystals.

$^1$H NMR (270 MHz, CDCl$_3$) δ: 8.00–7.70 (3H, m), 7.65–7.18 (8H, m), 5.23 (2H, s), 4.03–3.18 (12H, m), 2.57–2.21 (4H, m), 1.80–1.33 (6H, m), 1.17 (3H, t). MASS (m/z) 546 (M$^+$); Elemental Analysis: C$_{34}$H$_{38}$N$_6$O;

| Found (%) | C:74.43, H:6.93, N:15.63 |
| Calculated (%) | C:74.69, H:7.01, N:15.37 |

Example 28

1-[2-{N-Ethyl-N-(4-(1-piperidinomethyl)benzoyl)amino}ethyl]-3-(3,5-dichlorobenzyl)-2-imidazolidinylidenepropanedinitrile (Compound 28)

Compound (XI) (0.50 g) obtained in step 2 of Reference Example 11, 0.44 g of 3,5-dichlorobenzyl alcohol, 0.65 g of triphenylphosphine, and 1.1 ml of a 40% toluene solution of diethyl azodicarboxylate were allowed to react in 10 ml of toluene as described in Example 23 to give 0.45 g (64%) of Compound 28 as a pale yellow oily substance.

$^1$H NMR (270 MHz, CDCl$_3$) δ: 7.50–7.20 (5H, m), 7.16 (2H, s), 4.74 (2H, s), 4.10–3.30 (12H, m), 2.57–2.21 (4H, m), 1.80–1.33 (6H, m), 1.15 (3H, t).

Example 29

1-[2-{N-Ethyl-N-(4-(-1-propylaminomethyl)benzoyl)amino}ethyl]-3-(3,5-dimethylbenzyl)-2-imidazolidinylidenepropanedinitrile (Compound 29)

Compound (XII) (0.20 g) obtained in Reference Example 12, 0.24 ml of 3,5-dimethylbenzyl alcohol, 0.58 g of triphenylphosphine, and 0.96 ml of a 40% toluene solution of diethyl azodicarboxylate were allowed to react in 4.0 ml of tetrahydrofuran as described in Example 23 to give 0.11 g (40%) of Compound 29 as a pale yellow oily substance.

$^1$H NMR (270 MHz, CDCl$_3$) δ: 7.41 (2H, d), 7.37 (2H, d), 6.96 (1H, s), 6.87 (2H, s), 4.72 (2H, s), 4.03–3.64 (8H, m), 3.63–3.30 (4H, m), 2.63 (2H, t), 2.30 (6H, s), 1.56 (2H, tq), 1.17 (3H, t), 0.95 (3H, t). The signal which corresponds to secondary amine was not observed. MASS (m/z) 499 [(M+H)$^+$].

Example 30

1-[2-{N-Ethyl-N-(4-(1-propylaminomethyl)benzoyl)amino}ethyl]-3-(3,5-dichlorobenzyl)-2-imidazolidinylidenepropanedinitrile (Compound 30)

Compound (XII) (0.44 g) obtained in Reference Example 12, 0.61 g of 3,5-dichlorobenzyl alcohol, 0.91 g of triphenylphosphine, and 0.80 g of di-tert-butyl azodicarboxylate were allowed to react in 100 ml of tetrahydrofuran as described in Example 23 to give 0.35 g (51%) of Compound 30 as a pale yellow oily substance.

$^1$H NMR (270 MHz, CDCl$_3$) δ: 7.42–7.31 (5H, m), 7.16 (2H, d), 4.74 (2H, s), 3.92–3.79 (8H, m), 3.56–3.43 (4H, m), 2.61 (2H, t), 1.55 (2H, qt), 1.15 (3H, t), 0.93 (3H, t). The signal which corresponds to secondary amine was not observed.

The chemical formulae of Compounds 1 to 30 are shown in Tables 1–4 below.

TABLE 1
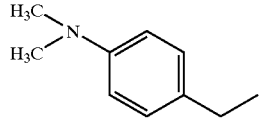
| Compound Number | R₁ | R₂ |
|---|---|---|
| 1 | 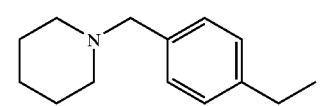 | $CH_3CH_2$ |
| 2 | 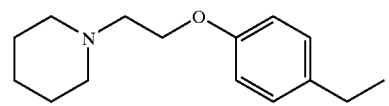 | $CH_3CH_2$ |
| 3 | 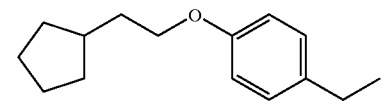 | $CH_3CH_2$ |
| 4 | 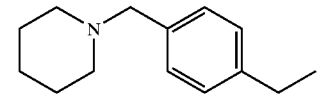 | $CH_3CH_2$ |
| 5 | 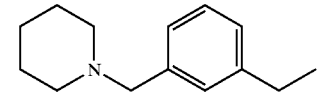 | $CH_3$ |
| 6 | 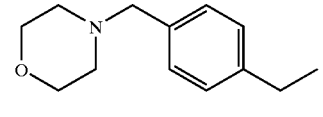 | $CH_3$ |
| 7 | 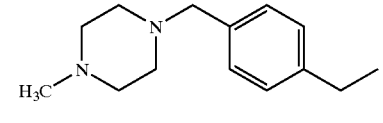 | $CH_3CH_2$ |
| 8 | 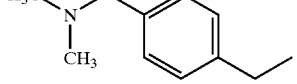 | $CH_3CH_2$ |
| 9 | 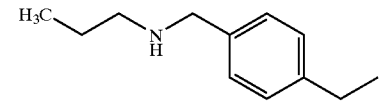 | $CH_3CH_2$ |
| 10 | 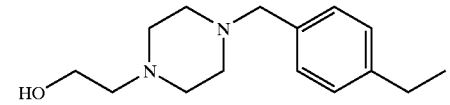 | $CH_3CH_2$ |
| 11 |  | $CH_3CH_2$ |

TABLE 2
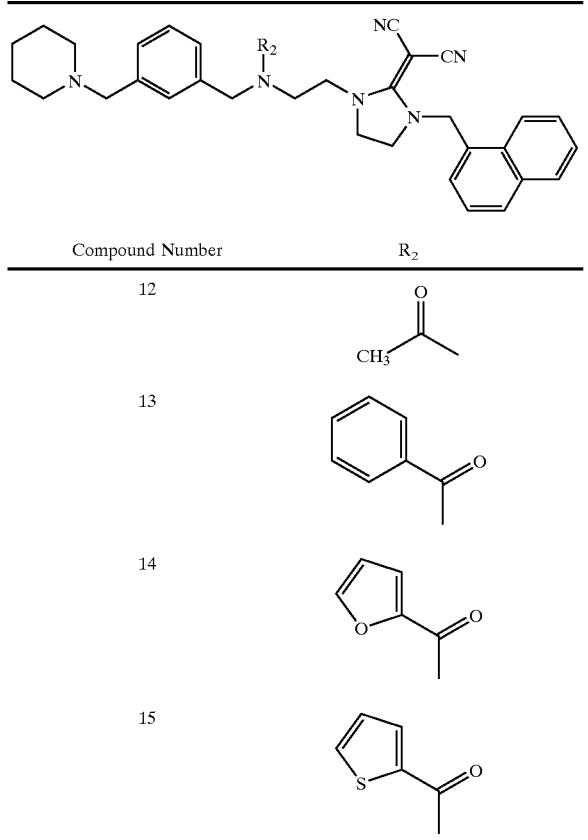
| Compound Number | R$_2$ |
| --- | --- |
| 12 | (acetyl, COCH$_3$) |
| 13 | (benzoyl) |
| 14 | (2-furoyl) |
| 15 | (2-thenoyl) |
| 16 | SO$_2$CH$_3$ |
| 17 | CH$_3$CH$_2$ |
| 18 | (benzyl) |
| 19 | (3-(piperidinylmethyl)benzyl) |
TABLE 3
| Compound Number | |
| --- | --- |
| 20 | |
| 21 | |
| 22 | |
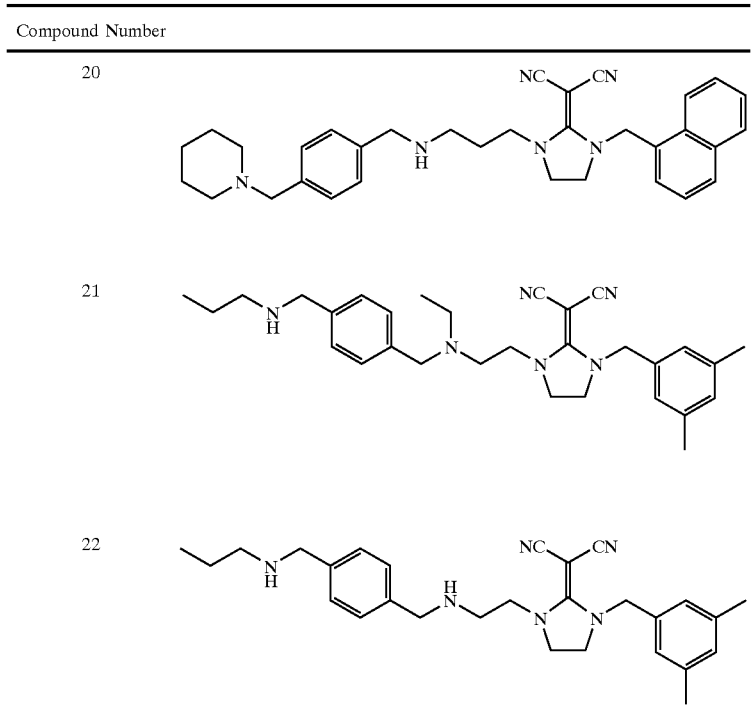

TABLE 3-continued
| Compound Number | |
|---|---|
| 23 | 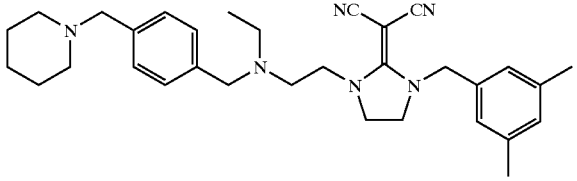 |
| 24 | 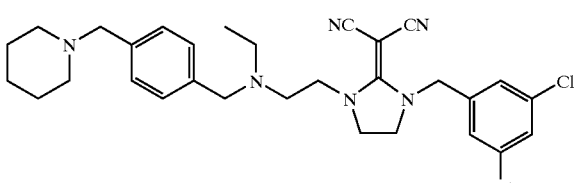 |
| 25 | 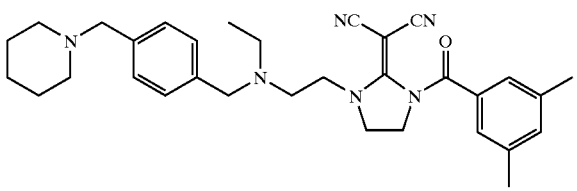 |
TABLE 4
| Compound Number | |
|---|---|
| 26 | 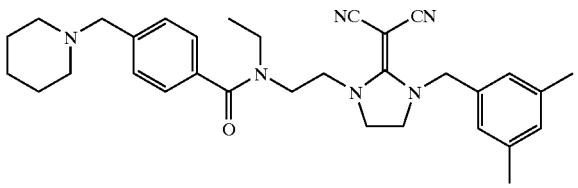 |
| 27 | 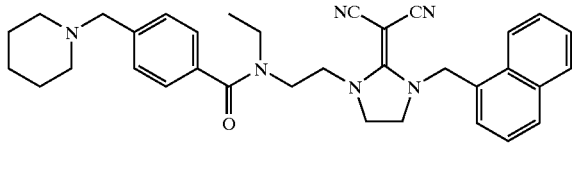 |
| 28 | 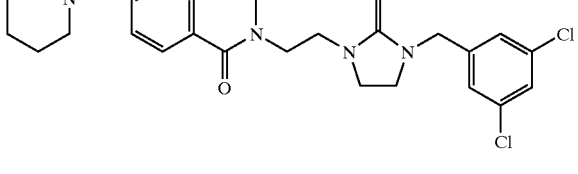 |
| 29 | 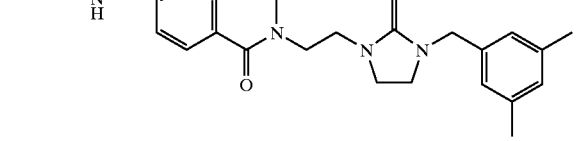 |

TABLE 4-continued

Compound Number

30 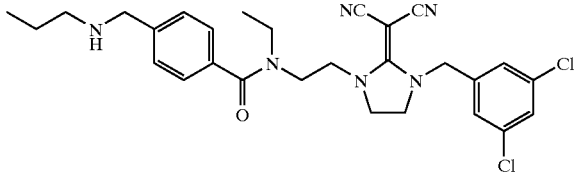

Reference Example 1

1-{2-(N-Ethylamino)ethyl}-3-(1-naphthylmethyl)-2-imidazolidinylidenepropanedinitrile (Compound (I))

Step 1:
1-(2-Aminoethyl)-3-(1-naphthylmethyl)-2-imidazolidinylidenepropanedinitrile (Compound (Ia)):

In 50 ml of dimethylformamide was dissolved 16.6 g of 1-(2-aminoethyl)-2-imidazolidinylidenepropanedinitrile obtained by a known process (JP92-279581), and 12.7 g of potassium tert-butoxide was added thereto at 0° C., followed by stirring for 30 minutes. To the mixture was added 16.7 g of 1-chloromethylnaphthalene, followed by further stirring for 1 hour. Water was added to the reaction mixture, and the solvent was removed by evaporation. An aqueous solution of sodium bicarbonate was added to the residue, and the mixture was extracted with chloroform. The extract was dried over potassium carbonate, and the solvent was removed by evaporation. The residue was purified by flash silica gel column chromatography (chloroform:methanol=100:1 to 20:1) to give 16.5 g (55%) of Compound (Ia) as pale yellow crystals.

Step 2:
1-{2-(N-Ethylamino)ethyl}-3-(1-naphthylmethyl)-2-imidazolidinylidenepropanedinitrile (Compound (I)):

Compound (Ia) (7.0 g), 6.2 ml of acetaldehyde, and 4.0 g of Molecular Sieves 3A (Wako Pure Chemical, Ltd.) were added to 100 ml of tetrahydrofuran, and the mixture was stirred at room temperature for 2 hours. The Molecular Sieves were removed, and the reaction mixture was dropwise added to a solution of 4.2 g of sodium borohydride in 100 ml of ethanol, followed by stirring at room temperature for 1 hour. An aqueous solution of sodium bicarbonate was added thereto, and the mixture was extracted with chloroform. The extract was dried over potassium carbonate and evaporated to remove the solvent. Recrystallization from ethyl acetate was conducted to give Compound (I) as pale yellow crystals in a yield of 47%.

$^1$H NMR (270 MHz, CDCl$_3$) δ: 7.9–7.4 (7H, m), 5.21 (2H, s), 3.69 (2H, t, J=6.6 Hz), 3.6–3.2 (4H, m), 2.95 (2H, t, J=6.6 Hz), 2.69 (2H, t, J=7.26 Hz), 1.11 (3H, t, J=7.26 Hz).

Reference Example 2

1-[2-{N-Ethyl-N-(4-hydroxybenzyl)amino}ethyl]-3-(1-naphthylmethyl)-2-imidazolidinylidenepropanedinitrile (Compound (II))

In 20 ml of tetrahydrofuran were dissolved 1.0 g of Compound (I) obtained in Reference Example 1 and 1.1 g of 4-hydroxybenzaldehyde, and 1.9 g of sodium triacetoxyborohydride was added thereto, followed by stirring at room temperature for 2 hours. An aqueous solution of sodium bicarbonate was added thereto, and the mixture was extracted with chloroform. The extract was dried over potassium carbonate, and the solvent was removed by evaporation. The residue was purified by silica gel column chromatography (hexane:ethyl acetate=2:1 to 0:1) to give 900 mg (67%) of Compound (II) as colorless crystals.

$^1$H NMR (270 MHz, CDCl$_3$) δ: 7.9–7.3 (7H, m), 7.10 (2H, d, J=8.6 Hz), 6.77 (2H, d, J=8.6 Hz), 5.09 (2H, s), 3.55 (2H, t, J=5.6 Hz), 3.44 (2H, s), 3.4–3.0 (4H, m), 2.71 (2H, t, J=5.6 Hz), 2.59 (2H, q, J=6.9 Hz), 1.12 (3H, t, J=6.9 Hz).

Reference Example 3

1-{2-(N-Methylamino)ethyl}-3-(1-naphthylmethyl)-2-imidazolidinylidenepropanedinitrile (Compound (III))

Step 1:
1-[2-{N-(2,4-Dinitrobenzenesulfonyl)amino}ethyl]-3-(1-naphthylmethyl)-2-imidazolidinylidenepropanedinitrile (Compound (IIIa)):

Compound (II) (5.2 g) obtained in Reference Example 1 and 5.3 g of 2,4-dinitrobenzylsulfonyl chloride were allowed to react in accordance with a known process (Tetrahedron Lett., 38(33): 5831–5834 (1997)). The reaction product was purified by flash silica gel column chromatography (chloroform:methanol=100:1) to give 9.2 g (100%) of Compound (IIIa) as red crystals.

Step 2:
1-[2-{N-(2,4-Dinitrobenzenesulfonyl)-N-methylamino}ethyl]-3-(1-naphthylmethyl)-2-imidazolidinylidenepropanedinitrile (Compound (IIIb))

Compound (IIIa) (4.0 g) and methyl iodide (0.9 ml) were allowed to react in accordance with a known process (Tetrahedron Lett., 38(33): 5831–5834 (1997)). The reaction product was purified by silica gel column chromatography (hexane:ethyl acetate=2:1 to 2:3) to give 1.6 g (39%) of Compound (IIIb) as red crystals.

Step 3:

1-{2-(N-Methylamino)ethyl}-3-(1-naphthylmethyl)-2-imidazolidinylidenepropanedinitrile (Compound (III))

Compound (IIIb) (1.6 g) was treated in accordance with a known process (Tetrahedron Lett., 38(33): 5831–5834 (1997)). The reaction product was purified by silica gel column chromatography (chloroform:methanol=50:1 to 10:1) to give 0.59 g (65%) of Compound (III) as colorless crystals.

$^1$H NMR (270 MHz, CDCl$_3$) δ: 7.9–7.4 (7H, m), 5.21 (2H, s), 3.71 (2H, t, J=6.6 Hz), 3.6–3.2 (4H, m), 2.92 (2H, t, J=6.6 Hz), 2.47 (3H, s).

Reference Example 4

1-[2-{N-Ethyl-N-(4-formylbenzyl)amino}ethyl]-3-(1-naphthylmethyl)-2-imidazolidinylidenepropanedinitrile (Compound (IV))

Compound (I) (3.5 g) and terephthalaldehyde monodiethyl acetal (6.6 g) were dissolved in 70 ml of tetrahydrofuran, and 6.7 g of sodium triacetoxyborohydride was added thereto, followed by stirring at room temperature for 2 hours. A 1 N aqueous solution of hydrochloric acid was added to the reaction mixture, and the mixture was stirred at room temperature for 15 minutes and then neutralized with a 2 N aqueous solution of sodium hydroxide. The reaction mixture was extracted with chloroform, and the extract was dried over potassium carbonate and evaporated to remove the solvent. The residue was purified by silica gel column chromatography (hexane:ethyl acetate=3:1 to 2:1) to give 2.56 g (52.4%) of Compound (IV) as colorless crystals.

$^1$H NMR (270 MHz, CDCl$_3$) δ: 9.98 (1H, s), 7.9–7.4 (11H, m), 5.14 (2H, s), 3.68 (2H, s), 3.64 (2H, t, J=6.3 Hz), 3.4–3.1 (4H, m), 2.78 (2H, t, J=6.3 Hz), 2.61 (2H, q, J=6.9 Hz), 1.11 (3H, t, J=6.9 Hz).

Reference Example 5

1-[2-{(4-Piperidinomethylbenzyl)amino}ethyl]-3-(1-naphthylmethyl)-2-imidazolidinylidenepropanedinitrile (Compound (V)):

In 50 ml of tetrahydrofuran were dissolved 692 mg of Compound (Ia), 300 mg of 4-piperidinomethylbenzaldehyde, and 0.45 ml of acetic acid, and 1.6 g of sodium triacetoxyborohydride were added thereto. The mixture was stirred at room temperature for 1 hour and then at 50° C. for 30 minutes, and a 2 mol/L aqueous solution of potassium hydroxide was added thereto on an ice bath. The reaction mixture was extracted with 500 ml of chloroform. The extract was washed with a saturated aqueous solution of sodium chloride and dried over magnesium sulfate, and the solvent was removed by evaporation. The residue was purified by silica gel column chromatography (chloroform:methanol:triethylamine=1:0:0 to 20:1:0.5) to give 289 mg (39%) of Compound (V) as a colorless oily substance.

$^1$H NMR (270 MHz, CDCl$_3$) δ: 7.95–7.05 (11H, m), 5.18 (2H, s), 3.81 (2H, s), 3.75–3.35 (4H, m), 3.58 (2H, s), 3.25 (2H, m), 2.94 (2H, t, J=5.9 Hz), 2.50 (4H, m), 1.63 (4H, m), 1.44 (2H, m). MASS (m/z) 505 [(M+H)$^+$].

Reference Example 6

1-(3-Aminopropyl)-3-(1-naphthylmethyl)-2-imidazolidinylidenepropanedinitrile (Compound (VI))

Step 1:
1-(3-Hydroxypropyl)-2-imidazolidinylidenepropanedinitrile (Compound (VIa)):

In 10 ml of methylene chloride was dissolved 10.4 g of N-(2-aminoethyl)propanolamine, and the solution was added to 15.0 g of [bis(methylthio)methylene]propanedinitrile. The mixture was allowed to stand at room temperature for 1 hour under reduced pressure. Diisopropyl ether was added to the mixture, and the solid was collected by filtration. The crystals were purified by silica gel column chromatography (chloroform:methanol=5:1) to give 15.0 g (87%) of Compound (VIa) as pale yellow crystals.

Step 2:
1-(3-Hydroxypropyl)-3-(1-naphthylmethyl)-2-imidazolidinylidenepropanedinitrile (Compound (VIb))

In 150 ml of tetrahydrofuran were suspended 5.0 g of Compound (VIa), 8.3 g of 1-naphthalenemethanol, and 20.5 g of triphenylphosphine, and 4.11 ml of diethyl azodicarboxylate was added to the suspension at 0° C. After stirring at room temperature for 6 hours, 1.4 ml of diethyl azodicarboxylate was further added thereto, followed by stirring at room temperature for additional 12 hours. The solvent was removed by evaporation, and the residue was purified by silica gel column chromatography (chloroform:methanol=50:1 to 30:1) to give 8.05 g (93%) of Compound (VIb) as white crystals.

Step 3:
1-(3-Aminopropyl)-3-(1-naphthylmethyl)-2-imidazolidinylidenepropanedinitrile (Compound (VI))

In 50 ml of pyridine was dissolved 5.0 g of Compound (VIb), and 5.73 g of p-toluenesulfonyl chloride was added to the solution at 0° C., followed by stirring for 3.5 hours. The solvent was removed by evaporation, water was added to the residue, and the mixture was extracted with chloroform. The extract was washed successively with diluted hydrochloric acid and a saturated aqueous solution of sodium chloride, dried over magnesium sulfate, and evaporated to remove the solvent. The resulting orange oily substance weighing 4.5 g was dissolved in 45 ml of dimethylformamide, and 4.17 g of sodium azide was added thereto, followed by stirring at 80° C. Water was added thereto, and the mixture was extracted with methylene chloride. The extract was washed with a saturated aqueous solution of sodium chloride, dried over magnesium sulfate, and evaporated to remove the solvent. The resulting orange crystals weighing 2.67 g were dissolved in 30 ml of ethyl acetate, and 2.94 g of triphenylphosphine was added to the solution. After stirring the mixture at 60° C. for 1 hour, 1.34 ml of water was added thereto, followed by further stirring for 4 hours. The solvent was removed by evaporation, and to the residue were added ethanol and 477 mg of fumaric acid, followed by heating to dissolve. After cooling, the crystals precipitated were collected by filtration to give 2.91 g of Compound (VI) as colorless crystals.

$^1$H NMR (270 MHz, CDCl$_3$) δ: 7.92–7.86 (3H, m), 7.64–7.38 (4H, m), 5.22 (2H, s), 3.69 (2H, t, J=7.7 Hz), 3.52–3.44 (2H, m), 3.30–3.23 (2H, m), 2.83 (2H, t, J=7.8 Hz), 1.86 (2H, tt, J=7.8, 6.8 Hz). MASS (m/z) 331 [(M+H)$^+$].

Reference Example 7

1-[2-{N-Ethyl-N-(4-propylaminomethylbenzyl)amino}ethyl]-2-imidazolidinylidenepropanedinitrile (Compound (VII))

Step 1:
1-{2-(N-Ethylamino)ethyl}-2-imidazolidinylidenepropanedinitrile (Compound (VIIa)):

30 g of 1-(2-aminoethyl)-2-imidazolidinylidenepropanedinitrile obtained by a known process (JP92-279581), 47 ml of acetaldehyde, 47 g of Molecular Sieves 3A, and 64 g of sodium borohydride were used as described in Example 1, step 2, to give 19 g (55%) of Compound (VIIa) as colorless crystals.

$^1$H NMR (270 MHz, CDCl$_3$) δ: 3.9–3.6 (6H, m), 2.92 (2H, t, J=6.6 Hz), 2.70 (2H, q, J=7.26 Hz), 1.11 (3H, t, J=7.26 Hz).

Step 2:
1-[2-{N-Ethyl-N-(4-formylbenzyl)amino}ethyl]-2-imidazolidinylidenepropanedinitrile (Compound (VIIb)):

12 g of Compound (VIIa), 38 ml of terephthalaldehyde monodiethyl acetal, and 37 g of sodium triacetoxyborohydride were used as described in Example 4 to give 8.4 g (44%) of Compound (VIIb) as colorless crystals.

$^1$H NMR (270 MHz, CDCl$_3$) δ: 10.01 (1H, s), 7.86 (2H, d, J=7.92 Hz), 7.42 (2H, d, J=7.92 Hz), 5.92 (1H, s), 3.7–3.5

(8H, m), 2.73 (2H, t, J=6.27 Hz), 2.60 (2H, q, J=7.26 Hz), 1.12 (3H, t, J=7.26 Hz).

Step 3:

1-[2-{N-Ethyl-N-(4-propylaminomethylbenzyl) amino}ethyl]-2-imidazolidinylidenepropanedinitrile (Compound (VII)):

0.40 g of Compound (VIb), 1.0 ml of n-propylamine, 0.7 ml of acetic acid, and 1.3 g of sodium triacetoxyborohydride were used as described in Example 7 to give 0.41 g (90%) of Compound (VII) as pale yellow crystals.

$^1$H NMR (270 MHz, CDCl$_3$) δ: 7.30 (2H, d, J=7.92 Hz), 7.25 (2H, d, J=7.92 Hz), 3.78 (2H, s), 3.7–3.4 (8H, m), 2.7–2.6 (6H, m), 1.56 (2H, tq, J=7.26, 7.26 Hz), 1.12 (3H, t, J=7.26 Hz), 0.93 (3H, t, J=7.26 Hz).

Reference Example 8

4-{N-tert-Butyloxycarbonyl-N-(1-propyl) aminomethyl}benzaldehyde (Compound (VIII))

Step 1:

4-{N-tert-Butyloxycarbonyl-N-(1-propyl) aminomethyl}benzaldehyde Diethylacetal (Compound (VIIIa)):

A mixture of 10 g of terephthalaldehyde monodiethylacetal and 11 ml of n-propylamine was stirred at 60° C. for 1 hour. After allowing the reaction mixture to cool, 300 ml of tetrahydrofuran was added thereto, and 12 g of sodium triacetoxyborohydride was added thereto under ice-cooling. The mixture was stirred at room temperature for 12 hours. An aqueous solution of sodium bicarbonate was added to the reaction mixture, and the mixture was extracted with chloroform. The extract was dried over potassium carbonate, and the solvent was evaporated under reduced pressure. To the residue were added 9.7 ml of triethylamine, 0.10 g of 4-dimethylaminopyridine, and 500 ml of dichloromethane. Di-tert-butyl dicarbonate was further added thereto under ice-cooling, followed by stirring at room temperature for 12 hours. An aqueous solution of sodium bicarbonate was added to the reaction mixture, and the mixture was extracted with chloroform. The extract was dried over potassium carbonate, and the solvent was evaporated under reduced pressure. The residue was purified by silica gel column chromatography (hexane:ethyl acetate=10:1 to 3:1) to give 7.0 g (42%) of Compound (VIIIa) as a colorless oily substance.

Step 2:

4-{N-tert-Butyloxycarbonyl-N-(1-propyl) aminomethyl}benzaldehyde (Compound (VIII)):

In 30 ml of methanol was dissolved 3.0 g of Compound (VIIIa) obtained in step 1 above, and 20 ml of a 33 vol % aqueous solution of acetic acid was added thereto, followed by stirring at room temperature for 4 hours. The solvent was removed by evaporation under reduced pressure, and an aqueous solution of sodium bicarbonate was added to the residue. The mixture was extracted with chloroform, and the extract was dried over potassium carbonate. The solvent was removed by evaporation under reduced pressure. The residue was purified by silica gel column chromatography (hexane:ethyl acetate=10:1 to 3:1) to give 1.2 g (51%) of Compound (VII) as a colorless oily substance.

$^1$H NMR (270 MHz, CDCl$_3$) δ: 9.98 (1H, s), 7.82 (2H, d), 7.36 (2H, d), 4.48 (2H, brs), 3.11 (2H, brs), 1.55–1.40 (11H, brs), 0.84 (3H, t).

Reference Example 9

1-{2-(N-Ethylamino)ethyl}-3-(3,5-dimethylbenzyl)-2-imidazolidinylidenepropanedinitrile (Compound (IX))

Step 1:

1-(2-Aminoethyl)-3-(3,5-dimethylbenzyl)-2-imidazolidinylidenepropanedinitrile (Compound (IXa)):

1-(2-Aminoethyl)-2-imidazolidinylidenepropanedinitrile (9.7 g) obtained by a known process (JP92-279581), 5.0 g of 3,5-dimethylbenzyl alcohol, 12 g of triphenylphosphine, and 10 g of di-tert-butyl azodicarboxylate were allowed to react in 500 ml of tetrahydrofuran as described in Example 23 to give 3.6 g (34%) of Compound (IXa) as a pale yellow oily substance.

$^1$H NMR (270 MHz, CDCl$_3$) δ: 6.89 (1H, s), 6.81 (2H, s), 4.62 (2H, s), 3.62–3.55 (4H, m), 3.42–3.34 (2H, m), 2.98 (2H, t), 2.25 (6H, s). The signal which corresponds to primary amine was not observed.

Step 2:

1-{2-(N-Ethylamino)ethyl}-3-(3,5-dimethylbenzyl)-2-imidazolidinylidenepropanedinitrile (Compound (IX)):

Compound (VIIa) (2.0 g) obtained in step 1 of Reference Example 7, 2.9 ml of 3,5-dimethylbenzyl alcohol, 5.1 g of triphenylphosphine, and 8.5 ml of a 40% toluene solution of diethyl azodicarboxylate were allowed to react in 40 ml of tetrahydrofuran as described in Example 23 to give 2.4 g (75%) of Compound (IX) as a pale yellow oily substance.

$^1$H NMR (270 MHz, CDCl$_3$) δ: 6.96 (1H, brs), 6.88 (2H, brs), 4.68 (2H, s), 3.78–3.60 (4H, m), 3.54–3.38 (2H, m), 2.95 (2H, t), 2.69 (2H, q), 2.32 (6H, s), 1.31 (1H, brs), 1.11 (3H, t).

Reference Example 10

1-[2-{N-Ethyl-N-(4-(1-piperidinomethyl)benzyl) amino}ethyl]-2-imidazolidinylidenepropanedinitrile (Compound (X))

Compound (VIIb) (3.4 g) obtained in step 2 of Reference Example 7, 5.2 ml of piperidine, 6.0 ml of acetic acid, and 11 g of sodium triacetoxyborohydride were allowed to react in 300 ml of tetrahydrofuran as described in Example 7 to give Compound (X). Recrystallization of the product from isopropyl alcohol was performed to give 2.9 g (69%) of Compound (X) as colorless crystals.

$^1$H NMR (270 MHz, CDCl$_3$) δ: 7.27 (2H, d), 7.22 (2H, d), 5.42 (1H, brs), 3.68–3.44 (10H, m), 2.72–2.67 (2H, m), 2.61 (2H, q), 2.37 (4H, m), 1.57 (4H, m), 1.43 (2H, m), 1.11 (3H, t). MASS (m/z) 392 (M$^+$).

Reference Example 11

1-[2-{N-Ethyl-N-(4-(1-piperidinomethyl)benzoyl) amino}ethyl]-2-imidazolidinylidenepropanedinitrile (Compound (XI))

Step 1:

1-[2-{N-Ethyl-N-(4-formylbenzoyl)amino}ethyl]-2-imidazolidinylidenepropanedinitrile (Compound (XIa)):

Compound (VIIa) (7.7 g) obtained in step 1 of Reference Example 7, 7.3 g of 4-carboxybenzaldehyde, 13 g of 1-(3-dimethylaminopropyl)-3-ethylcarbodiimide hydrochloride, and 10 g of 1-hydroxybenzotriazole were allowed to react in 100 ml of N,N-dimethylformamide as described in Example 26 to give 8.1 g (64%) of Compound (XIa) as colorless crystals.

$^1$H NMR (270 MHz, CDCl$_3$) δ: 10.06 (1H, s), 7.96 (2H, d), 7.53 (2H, d), 5.65 (1H, brs), 4.18–3.25 (10H, m), 1.11 (3H, t).

Step 2:
1-[2-{N-Ethyl-N-(4-(1-piperidinomethyl)benzoyl)amino}ethyl]-2-imidazolidinylidenepropanedinitrile (Compound (XI)):

Compound (XIa) (2.0 g) obtained in step 1 of Reference Example 11, 2.9 ml of piperidine, 3.4 ml of acetic acid, and 6.3 g of sodium triacetoxyborohydride were allowed to react in 40 ml of tetrahydrofuran as described in Example 7 to give 1.6 g (68%) of Compound (XI) as a pale yellow oily substance.

$^1$H NMR (270 MHz, CDCl$_3$) δ: 7.38 (2H, d), 7.31 (2H, d), 5.89 (1H, brs), 4.15–3.25 (12H, m), 2.58–2.20 (4H, m), 1.78–1.35 (6H, m), 1.11 (3H, t). MASS (m/z) 406 (M$^+$).

Reference Example 12

1-[2-{N-Ethyl-N-(4-(1-propylmethyl)benzoyl)amino}ethyl]-2-imidazolidinylidenepropanedinitrile (Compound (XII))

Compound (XIa) (0.50 g) obtained in step 1 of Reference Example 11, 0.61 ml of n-propylamine, 0.85 ml of acetic acid, and 1.6 g of sodium triacetoxyborohydride were allowed to react in 10 ml of tetrahydrofuran as described in Example 7 to give 0.55 g (100%) of Compound (XII) as a pale yellow oily substance.

$^1$H NMR (270 MHz, CDCl$_3$) δ: 7.40 (2H, d), 7.33 (2H, d), 5.64 (1H, brs), 4.20–3.30 (12H, m), 2.61 (2H, t), 1.70–1.45 (2H, m), 1.30–1.00 (3H, m), 0.93 (3H, t). The signal which corresponds to secondary amine was not observed. MASS (m/z) 381 [(M+H)$^+$].

Reference Example 13

4-(1-Piperidinomethyl)benzaldehyde (Compound (XIII))

In 300 ml of tetrahydrofuran was dissolved 26 g of terephthalaldehyde monodiethylacetal, and 13 ml of piperidine was added thereto, followed by stirring at room temperature for 4 hours. To the reaction mixture was added 53 g of sodium triacetoxyborohydride under ice-cooling, followed by stirring at room temperature for 4 hours. An aqueous solution of sodium bicarbonate was added to the reaction mixture, and the mixture was extracted with chloroform. The solvent was removed by evaporation under reduced pressure, and to the residue were added 60 ml of a 4 mol/L ethyl acetate solution of hydrogen chloride and 100 ml of ethyl acetate under ice-cooling. The mixture was filtered, and to the resultant solid was added an aqueous solution of sodium bicarbonate and the mixture was extracted with ethyl acetate. The extract was dried over potassium carbonate, and the solvent was evaporated under reduced pressure to give 23 g (90%) of Compound (XIII) as a pale yellow oily substance.

$^1$H NMR (270 MHz, CDCl$_3$) δ: 9.99 (1H, s), 7.83 (2H, m), 7.50 (2H, m), 3.53 (2H, s), 2.56–2.20 (4H, m), 1.74–1.30 (6H, m). MASS (m/z) 203 (M$^+$).

Reference Example 14

3-(1-Piperidinomethyl)benzaldehyde (Compound (XIV))

In 30 ml of tetrahydrofuran was dissolved 3.0 g of 3-(1-piperidinomethyl)benzyl alcohol obtained by a known process (EP86-172631), and 6.0 g of manganese dioxide was added thereto. The mixture was stirred at room temperature for 20 hours, followed by filtration. The solvent was evaporated under reduced pressure, and the residue was purified by silica gel column chromatography (hexane:ethyl acetate=3:1 to 1:1) to give 1.9 g (63%) of Compound (XIV) as a pale yellow oily substance.

$^1$H NMR (270 MHz, CDCl$_3$) δ: 10.00 (1H, s), 7.88–7.40 (4H, m), 3.53 (2H, s), 2.46–2.20 (4H, m), 1.62–1.30 (6H, m).

Test Example

Preparation of CXCR3 Transfectants

Cells:

L1/2 cells were grown in RPMI medium 1640, 10% Fetal Clone (Hyclone, Inc., Logan, Utah), 50 U/ml Penicillin/Streptomycin, 1 mmol/L NaPyruvate, and $5.5 \times 10^{-5}$ mol/L β-mercaptoethanol. Media components other than serum were purchased from GibcoBRL (Gaithersburg, Md.). Two days prior to transfection, the L1/2 cells were diluted 1:5 into fresh medium. This resulted in 150 million cells in log phase growth at a concentration of about 1–3 million cells/ml.

CXCR3 DNA and Transfection

*E. coli* XL1Blue cells (Stratagene, Inc., La Jolla, Calif.) were transformed with a pCDNA3-based (Invitrogen, San Diego, Calif.) CXCR3 cDNA expression plasmid (Qin, S. et al., *J. Clin. Invest.*, 101: 746–754 (1998), Loetscher, M. et al., *J. Exp. Med.*, 184: 963–969 (1996)) according to the manufacturer's protocol. Transformants were grown at 37° C. while shaking at 250 rpm in 500 ml of LB containing 100 μg/ml Ampicillin. The culture was then collected by centrifugation at 8,000 g, and the plasmid was purified using a Maxi plasmid purification column and protocol (Qiagen, Chatsworth, Calif.). Plasmid concentration and purity were determined using a 1% agarose gel and OD260/280 ratios. Plasmid DNA was suspended in ddH2O, and stored at −20° C. until use.

ScaI endonuclease was used to linearize the CXCR3 expression plasmid. 100 μg of DNA was digested with 10 μl of ScaI for 8 hours at 37° C. following the manufacturer's protocol (GibcoBRL, Cat# 15436-017). 20 μg was used directly in stable transfection (see below). 80 μg was cleaned of proteins and salts with a phenol:chloroform:isoamyl alcohol (25:24:1) extraction, 100% ethanol precipitation (with 0.1 volume NH$_4$COOH), and a 70% ethanol wash.

Stable transfectants of murine pre-B lymphoma cell line (L1/2) were prepared essentially as described (Ponath, P. D. et al., *J. Exp. Med.*, 183: 2437–2448 (1996)). 25 million L1/2 cells in 0.8 ml of 1×PBS were electroporated with 20 μg of linearized DNA, 20 μg linearized DNA that had been cleaned (see above under Linearization of DNA), or without DNA. Before electroporation, the L1/2 cells and the DNA were incubated for 10 minutes in 50 ml conical tubes (Falcon Model 2070, Becton Dickinson LabWare, Lincoln Park, N.J.) with gentle mixing (swirling) every 2 minutes. The L1.2 cell-DNA mixture was transferred into Gene Pulser cuvettes (BioRad, Richmond, Calif.) with a 0.4 cm electrode gap. The mixture was then electroporated at 250V and 960 μF, with the duration of shock and the actual voltage being measured. After electroporation, the cuvette was left undisturbed for 10 minutes at room temperature. All of the L1.2 cells-DNA mixture was then transferred to a T-25 tissue culture flask (Costar, Cambridge, Mass.), and grown for two days in 10 ml non-selective medium.

Selection:

L1/2 cells expressing CXCR3 were then subjected to selection for neomycin resistance. After two days of growth in non-selective medium, 10 ml of 1.6 g/L G418 (GibcoBRL) was added to the culture for a final concentration of 0.8 g/L (the selective and maintenance concentration). This was then allowed to grow for 10 to 15 days, with fresh selective medium added when cells started to over-grow. Fresh selective medium consisted of RPMI-1640 supplemented with 10% bovine serum, 50 U/ml Penicillin/Streptomycin, 1 mmol/L NaPyruvate, $5.5 \times 10^{-5}$ mol/L β-mercaptoethanol and 0.8 g/L G418.

The cell surface expression of CXCR3 was assessed by chemotaxis. Ligand binding and Scatchard analysis were also used to monitor surface expression. After G418 selection, CXCR3 expressing L1/2 cells were selected based on chemotaxis ability. For each electroporation reaction culture, 30 ml (800,000 cells/ml) were collected, and suspended in 600 $\mu$l selective medium. Selective medium, 600 $\mu$l, containing 10 n mol/L IP-10, was placed into the bottom chamber of BioCoat cell culture plates from Becton Dickinson. 100 $\mu$l/well of the L1/2 cells were added to the top chamber of the BioCoat plates. The cells were then left to chemotax overnight in a $CO_2$ incubator at 37° C. The next day, the top chambers with the non-chemotaxing cells were removed. The cells which chemotaxed were collected from the bottom chamber, transferred into fresh medium and allowed to grow in a 24-well plate. They were subsequently expanded into a T-25 and then a T-75 flask from Costar.

Transfectants expressing high level of receptors were cloned by limiting dilution. CXCR3 transfected cells were diluted to between 30 cells/ml and 3 cell/ml in selection medium containing G418. Aliquots of the dilutions were added to 96-well tissue culture plates at 100 $\mu$l/well. After 14 days at 37° C. and 5% $CO_2$, wells containing single colonies were identified under an inverted microscope. 50 $\mu$l of the cells were then transferred and stained with anti-CXCR3 mAb and analyzed by flow cytometry as described (Qin, S. et al., *J. Clin. Invest.*, 101: 746–754 (1998)). The level of receptor expression correlated with mean fluorescence intensity and cells which expressed high levels of CXCR3 were selected. Once a stable cell line was established, the line was expanded for use, and is referred to herein as CXCR3.L1/2.

CXCR3/IP-10 Radioligand Binding

CXCR3.L1/2 Membrane Preparation

CXCR3.L1/2 cells were pelleted by centrifugation and stored at −80° C. The cells were lysed by thawing and resuspending at about $1.5 \times 10^7$ cells/ml in a hypotonic buffer (5 m mol/L HEPES (pH 7.2), 2 mmol/L EDTA, 10 $\mu$g/ml each leupeptin, aprotinin, and chymostatin, and 100 $\mu$g/ml PMSF (all from Sigma, St. Louis)). Nuclei and cellular debris was removed by centrifugation (500 g to 100 g, at 4° C.) for 10 min. The supernatant was transferred to chilled centrifuge tubes (Nalge, Rochester, N.Y.) and the membrane fraction was recovered by centrifugation (25,000 g at 4° C.) for 45 min. The membrane pellet was resuspended in freezing buffer (10 mM HEPES (pH 7.2), 300 mmol/L Sucrose, 5 $\mu$g/ml each of leupeptin, aprotinin, and chymostatin, and 10 $\mu$g/ml PMSF). The total protein concentration was determined using a coomassie blue staining protein concentration assay kit (BioRad). The membrane preparation was aliquoted and stored at −80° C. until time of use.

Binding Assay:

CXCR3/IP-10 binding was performed in 96-well polypropylene plates (Costar) in a final volume of 0.1 ml of HBB buffer (50 mmol/L Hepes pH 7.4, 1 mmol/L $CaCl_2$, 5 mmol/L $MgCl_2$, 0.02% sodium azide, 0.5% BSA (bovine serum albumin)) containing 1 to 5 $\mu$g of CXCR3.L1/2 transfectant cell membrane protein and 0.05 to 0.2 nmol/L $^{125}$I-labeled IP-10 (NEN, Boston, Mass.). Competition binding experiments were performed by including variable concentrations of unlabeled IP-10 or test compound. Nonspecific binding was determined following the addition of a 250 nmol/L unlabelled IP-10. Samples were incubated for 60 min at room temperature, and bound and free tracer ($^{125}$I-IP10) were separated by filtration through 96-well GF/B filterplates (Packard) presoaked in 0.3% polyethyleneimine. The filters were washed in HBB further supplemented with 0.5 mol/L NaCl, dried, and the amount of bound radioactivity determined by liquid scintillation counting. The competition is presented as the percent specific binding as calculated by $100 \times [(S-B)/(T-B)]$, where S is the radioactivity bound for each sample, B is background binding, and T is total bound in the absence of competitors. Duplicates were used throughout the experiments. The results are shown in Tables 5 and 6.

TABLE 5

| Compound Number | % inhibition at 10 $\mu$mol/L |
|---|---|
| 2 | 96 |
| 4 | 76 |
| 5 | 99 |
| 6 | 99 |
| 7 | 92 |
| 8 | 86 |
| 9 | 94 |
| 10 | 100 |
| 11 | 91 |
| 12 | 76 |
| 13 | 61 |
| 14 | 85 |
| 15 | 71 |
| 16 | 89 |
| 17 | 96 |
| 18 | 67 |
| 19 | 68 |
| 20 | 74 |
| 21 | 99 |

TABLE 6

| Compound Number | % inhibition at 10 $\mu$mol/L |
|---|---|
| 22 | 92 |
| 23 | 97 |
| 24 | 91 |
| 25 | 99 |
| 26 | 64 |
| 27 | 72 |
| 28 | 41 |
| 29 | 51 |
| 30 | 73 |

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A compound represented having the structural formula:

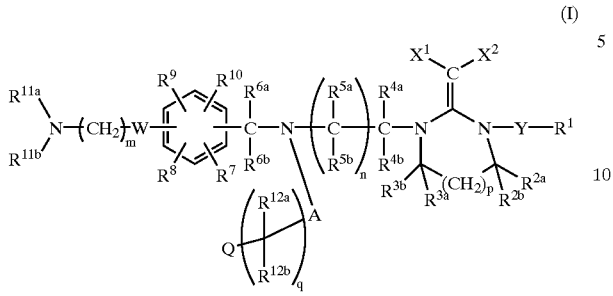

(I)

or physiologically acceptable salt thereof, wherein:

A is
    a bond,
    —C(=O)—,
    or —SO$_2$—;

Q is
    hydrogen,
    —COOH,
    substituted or unsubstituted cycloalkyl,
    substituted or unsubstituted polycycloalkyl,
    substituted or unsubstituted lower alkenyl,
    susbsituted or unsubstituted cycloalkenyl,
    substituted or unsubstituted aryl,
    substituted or unsubstituted heteroaryl, or
    Q and $R^7$ taken together form a bond;

W is
    a bond,
    —O—,
    —S—, or
    —NR$^{13}$—, wherein
    $R^{13}$ is
        hydrogen,
        substituted or unsubstituted lower alkyl,
        substituted or unsubstituted cycloalkyl,
        substituted or unsubstituted aryl,
        substituted or unsubstituted aralkyl, or
        substituted or unsubstituted heteroarylalkyl;

$X^1$ and $X^2$ are each, independently,
    hydrogen,
    —CN,
    —NO$_2$,
    —SO$_2$R$^{14a}$,
    —SO$_2$NR$^{14a}$R$^{14b}$,
    —C(=O)—R$^{14a}$,
    —C(=O)—OR$^{14a}$, or
    —C(=O)—NR$^{14a}$R$^{14b}$ wherein
    R$^{14a}$ and R$^{14b}$ are each, independently,
        hydrogen,
        substituted or unsubstituted lower alkyl,
        substituted or unsubstituted cycloalkyl,
        substituted or unsubstituted aryl, or
        substituted or unsubstituted aralkyl;

Y is
    a bond,
    —SO$_2$—,
    —(C=O)—, or
    —(CR$^{15a}$R$^{15b}$)—, wherein
    R$^{15a}$ and R$^{15b}$ are each, independently,
        hydrogen,
        substituted or unsubstituted lower alkyl,
        substituted or unsubstituted cycloalkyl,
        substituted or unsubstituted aryl, or
        substituted or unsubstituted aralkyl;

$R^1$ is
    substituted or unsubstituted lower alkyl,
    substituted or unsubstituted cycloalkyl,
    substituted or unsubstituted polycycloalkyl,
    substituted or unsubstituted lower alkenyl,
    substituted or unsubstituted cycloalkenyl,
    substituted or unsubstituted aryl,
    substituted or unsubstituted heteroaryl,
    substituted or unsubstituted aralkyl,
    substituted or unsubstituted heteroarylalkyl,
    substituted or unsubstituted lower alkoxy,
    substituted or unsubstituted lower alkanyoloxy, or
    a substituted or unsubstituted non-aromatic heterocyclic group;

$R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each, independently,
    hydrogen,
    substituted or unsubstituted lower alkyl,
    substituted or unsubstituted cycloalkyl,
    substituted or unsubstituted aryl,
    substituted or unsubstituted aralkyl,
    substituted or unsubstituted heteroarylalkyl, or
$R^{6a}$ and $R^{6b}$ taken together with the carbon atom to which they are bonded form —C(=O)—;

$R^7$, $R^8$, $R^9$, and $R^{10}$ are each, independently,
    hydrogen,
    hydroxy,
    substituted or unsubstituted lower alkyl,
    substituted or unsubstituted lower alkoxy,
    substituted or unsubstituted lower alkanoyl,
    substituted or unsubstituted lower alkanoyloxy
    substituted or unsubstituted lower alkoxycarbonyl,
    substituted or unsubstituted aryl,
    substituted or unsubstituted heteroaryl,
    halogen,
    —CN,
    —NO$_2$,
    —COOR$^{16a}$,
    —NR$^{16a}$R$^{16b}$, or
    —CONR$^{16a}$R$^{16b}$, wherein
    R$^{16a}$ and R$^{16b}$ are each, independently,
        hydrogen,
        substituted or unsubstituted lower alkyl,
        substituted or unsubstituted cycloalkyl,
        substituted or unsubstituted aryl,
        substituted or unsubstituted aralkyl, or
    R$^{16a}$ and R$^{16b}$ taken together with the nitrogen atom to which they are bonded form a substituted or unsubstituted heterocyclic group containing at least one nitrogen atom;

R$_{11a}$ and R$^{11b}$ are each, independently,
    hydrogen,
    substituted or unsubstituted lower alkyl,
    substituted or unsubstituted cycloalkyl,
    substituted or unsubstituted aryl,
    substituted or unsubstituted aralkyl,
    substituted or unsubstituted heteroarylalkyl, or
$R^{11a}$ and $R^{11b}$ taken together with the nitrogen atom to which they are bonded form a substituted or unsubstituted heterocyclic group containing at least one nitrogen atom;

$R^{12a}$ and $R^{12b}$ are each, independently,
    hydrogen,
    substituted or unsubstituted lower alkyl, substituted or unsubstituted cycloalkyl,
substituted or unsubstituted aryl,
substituted or unsubstituted aralkyl,
substituted or unsubstituted heteroarylalkyl, or $R^{12a}$ and $R^{12b}$ taken together with the carbon atom to which they are bonded form a substituted or unsubstituted cyclic group;

n is an integer from 0 to about 4;

m is an integer from 0 to about 6;

p is an integer from 0 to about 2; and q is an integer from 0 to about 8.

2. The compound according to claim 1, wherein $R^1$ is substituted or unsubstituted aryl, substituted or unsubstituted heteroaryl, substituted or unsubstituted aralkyl, substituted or unsubstituted heteroaralkyl.

3. The compound according to claim 1, wherein $X^1$ and $X^2$ are each —CN.

4. The compound according to claim 1, wherein Q is hydrogen, —COOH, substituted or unsubstituted aryl or substituted or unsubstituted heteroaryl.

5. The compound according to claim 1, wherein W is —O— or a bond.

6. The compound according to claim 1, wherein W is at the para or meta position of the benzene ring from the —$CR^{6a}R^{6b}$— group.

7. The compound according to claim 1, wherein $R^{2a}$, $R^{2b}$, $R^{3a}$, $R^{3b}$, $R^{4a}$, $R^{4b}$, $R^{5a}$, $R^{5b}$, $R^{6a}$, $R^{6b}$, $R^7$, $R^8$, $R^9$ and $R^{10}$ are each hydrogen.

8. The compound according to claim 1, wherein $R^{11a}$ and $R^{11b}$ are each, independently hydrogen or substituted or unsubstituted lower alkyl, or $R^{11a}$ and $R^{11b}$ taken together with the nitrogen atom to which they are bonded form a substituted or unsubstituted heterocyclic ring containing at least one nitrogen atom.

9. The compound according to claim 1, wherein

W is a bond or —O—;

$X^1$ and $X^2$ are each —CN;

$R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each hydrogen and n is 1.

10. The compound according to claim 9, wherein

Q is hydrogen, substituted or unsubstituted cycloalkyl, or substituted or unsubstituted lower alkenyl;

W is at the para- or meta-position of the benzene ring from the —$CR^{6a}R^{6b}$— group;

$R^7$, $R^8$, $R^9$, and $R^{10}$ are each hydrogen; and q is 0, 1, 2, 3, 4, 5, or 6.

11. The compound according to claim 10, wherein $R^1$ is substituted or unsubstituted aryl, substituted or unsubstituted heteroaryl, substituted or unsubstituted aralkyl, or substituted or unsubstituted heteroarylalkyl.

12. The compound according to claim 1, wherein Y is a bond, —C(=O)— or —$CH_2$—.

13. The compound according to claim 1, wherein $R^1$ is a substituted or unsubstituted aryl;

Y is a bond;

q is zero, one or two;

Q is hydrogen, substituted or unsubstituted aryl, or substituted or unsubstituted heteroaryl;

m is zero, one or two;

n is one or two;

$R^7$, $R^8$, $R^9$ and $R^{10}$ are hydrogen; and $R^{11a}$ and $R^{11b}$ are each, independently hydrogen, or substituted or unsubstituted lower alkyl, or $R^{11a}$ and $R^{11b}$ taken together with the nitrogen atom to which they are bonded form a substituted or unsubstituted heterocyclic ring containing at least one nitrogen atom.

14. A composition comprising the compound according to claim 1, and a physiologically acceptable carrier.

15. A method of inhibiting inflammation in an individual, comprising administering to the individual a therapeutically effective amount of a compound having the structural formula:

or physiologically acceptable salt thereof, wherein:

A is a bond,

—C(=O)—, or

—$SO_2$—;

Q is hydrogen,

—COOH substituted or unsubstituted cycloalkyl, substituted or unsubstituted polycycloalkyl, substituted or unsubstituted lower alkenyl, susbsituted or unsubstituted cycloalkenyl, substituted or unsubstituted aryl, substituted or unsubstituted heteroaryl, or Q and $R^7$ taken together form a bond;

W is a bond,

—O—,

—S—, or

—$NR^{13}$—, wherein $R^{13}$ is hydrogen, substituted or unsubstituted lower alkyl, substituted or unsubstituted cycloalkyl, substituted or unsubstituted aryl, substituted or unsubstituted aralkyl, or substituted or unsubstituted heteroarylalkyl;

$X^1$ and $X^2$ are each, independently, hydrogen,

—CN,

—$NO_2$, $SO_2NR^{14a}R^{14b}$,

—C(=O)—$R^{14a}$,

—C(=O)—$OR^{14a}$, or

—C(=O)—$NR^{14a}R^{14b}$, wherein $R^{14a}$ and $R^{14b}$ are each, independently, hydrogen, substituted or unsubstituted lower alkyl, substituted or unsubstituted cycloalkyl, substituted or unsubstituted aryl, or substituted or unsubstituted aralkyl;

Y is
  a bond,
  —SO$_2$—
  —(C=O)—, or
  —(CR$^{15a}$R$^{15b}$)—, wherein
    R$^{15a}$ and R$^{15b}$ are each, independently,
      hydrogen,
      substituted or unsubstituted lower alkyl,
      substituted or unsubstituted cycloalkyl,
      substituted or unsubstituted aryl, or
      substituted or unsubstituted aralkyl;
R$^1$ is
  substituted or unsubstituted lower alkyl,
  substituted or unsubstituted cycloalkyl,
  substituted or unsubstituted polycycloalkyl,
  substituted or unsubstituted lower alkenyl,
  substituted or unsubstituted cycloalkenyl,
  substituted or unsubstituted aryl,
  substituted or unsubstituted heteroaryl,
  substituted or unsubstituted aralkyl,
  substituted or unsubstituted heteroarylalkyl,
  substituted or unsubstituted lower alkoxy,
  substituted or unsubstituted lower alkanoyloxy, or
  a substituted or unsubstituted non-aromatic heterocyclic group;
R$^{2a}$, R$^{2b}$, R$^{3a}$, R$^{3b}$, R$^{4a}$, R$^{4b}$, R$^{5a}$, R$^{5b}$, R$^{6a}$, and R$^{6b}$ are each, independently,
  hydrogen,
  substituted or unsubstituted lower alkyl,
  substituted or unsubstituted cycloalkyl,
  substituted or unsubstituted aryl,
  substituted or unsubstituted aralkyl,
  substituted or unsubstituted heteroarylalkyl, or
R$^{6a}$ and R$^{6b}$ taken together with the carbon atom to which they are bonded form —C(=O)—;
R$^7$, R$^8$, R$^9$, and R$^{10}$ are each, independently,
  hydrogen,
  hydroxy,
  substituted or unsubstituted lower alkyl,
  substituted or unsubstituted lower alkoxy,
  substituted or unsubstituted lower alkanoyl,
  substituted or unsubstituted lower alkanoyloxy
  substituted or unsubstituted lower alkoxycarbonyl,
  substituted or unsubstituted aryl,
  substituted or unsubstituted heteroaryl,
  halogen,
  —CN,
  —NO$_2$,
  —COOR$^{16a}$,
  —NR$^{16a}$R$^{16b}$, or
  —CONR$^{16a}$R$^{16b}$, wherein
    R$^{16a}$ and R$^{16b}$ are each, independently,
      hydrogen,
      substituted or unsubstituted lower alkyl,
      substituted or unsubstituted cycloalkyl,
      substituted or unsubstituted aryl,
      substituted or unsubstituted aralkyl; or
    R$^{16a}$ and R$^{16b}$ taken together with the nitrogen atom to which they are bonded form a substituted or unsubstituted heterocyclic group containing at least one nitrogen atom;
R$^{11a}$ and R$^{11b}$ are each, independently,
  hydrogen,
  substituted or unsubstituted lower alkyl,
  substituted or unsubstituted cycloalkyl,
  substituted or unsubstituted aryl,
  substituted or unsubstituted aralkyl,
  substituted or unsubstituted heteroarylalkyl, or
  R$^{11a}$ and R$^{11b}$ taken together with the nitrogen atom to which they are bonded form a substituted or unsubstituted heterocyclic group containing at least one nitrogen atom;
R$^{12a}$ and R$^{12b}$ are each, independently,
  hydrogen,
  substituted or unsubstituted lower alkyl,
  substituted or unsubstituted cycloalkyl,
  substituted or unsubstituted aryl,
  substituted or unsubstituted aryl,
  substituted or unsubstituted aralkyl,
  substituted or unsubstituted heteroarylalkyl, or
  R$^{12a}$ and R$^{12b}$ taken together with the carbon atom to which they are bonded form a substituted or unsubstituted cyclic group;
n is an integer from 0 to about 4;
m is an integer from 0 to about 6;
p is an integer from 0 to about 2; and
q is an integer from 0 to about 8.

16. The method of claim 15, wherein said inflammation is a consequence of an autoimmune disease.

17. The method of claim 15, wherein said inflammation is a consequence of an allergic disease or condition.

18. The method of claim 15, wherein said inflammation is a consequence of infection.

19. The method of claim 18, wherein said infection is bacterial, viral, fungal or parasitic.

20. A method of treating an individual having a disease associated with pathogenic leukocyte recruitment and/or activation, comprising administering to the individual a therapeutically effective amount of a compound having the structural formula:

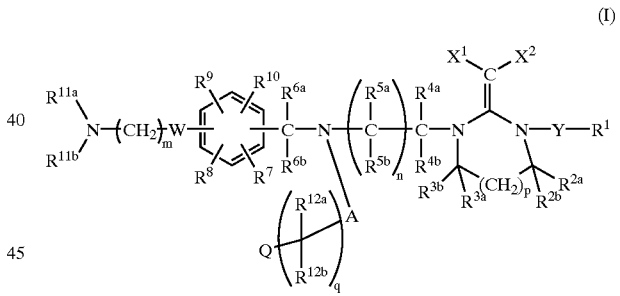

(I)

or physiologically acceptable salt thereof, wherein:
A is
  a bond,
  —C(=O)—, or
  —SO$_2$—;
Q is
  hydrogen,
  —COOH,
  substituted or unsubstituted cycloalkyl,
  substituted or unsubstituted polycycloalkyl,
  substituted or unsubstituted lower alkenyl,
  substituted or unsubstituted lower alkynyl,
  substituted or unsubstituted cycloalkenyl,
  substituted or unsubstituted aryl,
  substituted or unsubstituted heteroaryl, or
  Q and R$^7$ taken together form a bond;
W is
  a bond,
  —O—, —S—, or
—NR$^{13}$—, wherein
R$^{13}$ is
  hydrogen,
  substituted or unsubstituted lower alkyl,
  substituted or unsubstituted cycloalkyl,
  substituted or unsubstituted aryl,
  substituted or unsubstituted aralkyl, or
  substituted or unsubstituted heteroarylalkyl;
X$^1$ and X$^2$ are each, independently,
  hydrogen,
  —CN,
  —NO$_2$,
  —SO$_2$R$^{14a}$,
  —SO$_2$NR$^{14a}$R$^{14b}$,
  —C(=O)—R$^{14a}$,
  —C(=O)—OR$^{14a}$, or
  —C(=O)—NR$^{14a}$R$^{14b}$, wherein
  R$^{14a}$ and R$^{14b}$ are each, independently,
    hydrogen,
    substituted or unsubstituted lower alkyl,
    substituted or unsubstituted cycloalkyl,
    substituted or unsubstituted aryl, or
    substituted or unsubstituted aralkyl;
Y is
  a bond,
  —SO$_2$—,
  —(C=O)—, or
  —(CR$^{15a}$R$^{15b}$)—, wherein
  R$^{15a}$ and R$^{15b}$ are each, independently,
    hydrogen,
    substituted or unsubstituted lower alkyl,
    substituted or unsubstituted cycloalkyl,
    substituted or unsubstituted aryl, or
    substituted or unsubstituted aralkyl;
R$^1$ is
  substituted or unsubstituted lower alkyl,
  substituted or unsubstituted cycloalkyl,
  substituted or unsubstituted polycycloalkyl,
  substituted or unsubstituted lower alkenyl,
  substituted or unsubstituted cycloalkenyl,
  substituted or unsubstituted aryl,
  substituted or unsubstituted heteroaryl,
  substituted or unsubstituted aralkyl,
  substituted or unsubstituted heteroarylalkyl,
  substituted or unsubstituted lower alkoxy,
  substituted or unsubstituted lower alkanoyloxy,
  a substituted or unsubstituted non-aromatic heterocyclic group;
R$^{2a}$, R$^{2b}$, R$^{3a}$, R$^{3b}$, R$^{4a}$, R$^{4b}$, R$^{5a}$, R$^{5b}$, R$^{6a}$, and R$^{6b}$ are each, independently,
  hydrogen,
  substituted or unsubstituted lower alkyl,
  substituted or unsubstituted cycloalkyl,
  substituted or unsubstituted aryl,
  substituted or unsubstituted aralkyl,
  substituted or unsubstituted heteroarylalkyl, or
R$^{6a}$ and R$^{6b}$ taken together with the carbon atom to which they are bonded form —C(=O)—;

R$^7$, R$^8$, R$^9$, and R$^{10}$ are each, independently,
  hydrogen,
  hydroxy,
  substituted or unsubstituted lower alkyl,
  substituted or unsubstituted lower alkoxy,
  substituted or unsubstituted lower alkanoyl,
  substituted or unsubstituted lower alkanoyloxy
  substituted or unsubstituted lower alkoxycarbonyl,
  substituted or unsubstituted aryl,
  substituted or unsubstituted heteroaryl,
  halogen,
  —CN,
  —NO$_2$,
  —COOR$^{16a}$,
  —NR$^{16a}$R$^{16b}$, or
  —CONR$^{16a}$R$^{16b}$, wherein
  R$^{16a}$ and R$^{16b}$ are each, independently,
    hydrogen,
    substituted or unsubstituted lower alkyl,
    substituted or unsubstituted cycloalkyl,
    substituted or unsubstituted aryl,
    substituted or unsubstituted aralkyl, or
  R$^{16a}$ and R$^{16b}$ taken together with the nitrogen atom to which they are bonded form a substituted or unsubstituted heterocyclic group containing at least one nitrogen atom;
R$^{11a}$ and R$^{11b}$ are each, independently,
  hydrogen,
  substituted or unsubstituted lower alkyl,
  substituted or unsubstituted cycloalkyl,
  substituted or unsubstituted aryl,
  substituted or unsubstituted aralkyl,
  substituted or unsubstituted heteroarylalkyl, or
  R$^{11a}$ and R$^{11b}$ taken together with the nitrogen atom to which they are bonded form a substituted or unsubstituted heterocyclic group containing at least one nitrogen atom;
R$^{12a}$ and R$^{12b}$ are each, independently,
  hydrogen,
  substituted or unsubstituted lower alkyl,
  substituted or unsubstituted cycloalkyl,
  substituted or unsubstituted aryl,
  substituted or unsubstituted aralkyl,
  substituted or unsubstituted heteroarylalkyl, or
  R$^{12a}$ and R$^{12b}$ taken together with the carbon atom to which they are bonded form a substituted or unsubstituted cyclic group;
n is an integer from 0 to about 4;
m is an integer from 0 to about 6;
p is an integer from 0 to about 2; and
q is an integer from 0 to about 8.

21. The method of claim 20, wherein said disease is an autoimmune disease.

22. The method of claim 20, wherein said disease is an allergic disease or condition.

* * * * *

UNITED STATES PATENT AND TRADEMARK OFFICE
CERTIFICATE OF CORRECTION

PATENT NO.     : 6,469,002 B1
DATED          : October 22, 2002
INVENTOR(S)    : Etsuo Ohshima et al.

It is certified that error appears in the above-identified patent and that said Letters Patent is hereby corrected as shown below:

Column 46,
Line 54, delete "$R_{11a}$" and insert -- $R^{11a}$ --.

Column 48,
Line 57, after "-$NO_2$," add -- -$SO_2R^{14a}$, --.
Line 58, at beginning of line add -- - --.

Column 50,
Line 12, delete line 12 (duplicate line).

Signed and Sealed this

Eighteenth Day of March, 2003

JAMES E. ROGAN
*Director of the United States Patent and Trademark Office*